US007662561B2

(12) United States Patent
Godfrey et al.

(10) Patent No.: US 7,662,561 B2
(45) Date of Patent: Feb. 16, 2010

(54) IDENTIFICATION OF MARKERS IN ESOPHAGEAL CANCER, COLON CANCER, HEAD AND NECK CANCER, AND MELANOMA

(75) Inventors: Tony E. Godfrey, Bronxville, NY (US); Liqiang Xi, Plainsboro, NJ (US); Siva Raja, Jamaica Plain, MA (US); Steven J. Hughes, Blawnox, PA (US); William E. Gooding, Pittsburgh, PA (US)

(73) Assignee: University of Pittsburgh-Of the commonwealth System of Higher Education, Pittsburgh, PA (US)

( * ) Notice: Subject to any disclaimer, the term of this patent is extended or adjusted under 35 U.S.C. 154(b) by 159 days.

(21) Appl. No.: 11/178,134

(22) Filed: Jul. 8, 2005

(65) Prior Publication Data

US 2006/0019290 A1 Jan. 26, 2006

Related U.S. Application Data

(60) Provisional application No. 60/587,019, filed on Jul. 9, 2004, provisional application No. 60/586,599, filed on Jul. 9, 2004.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33
(58) Field of Classification Search .................. None
See application file for complete search history.

(56) References Cited

U.S. PATENT DOCUMENTS

| | | | |
|---|---|---|---|
| 5,314,809 A | 5/1994 | Erlich et al. |
| 5,814,491 A | 9/1998 | Vijg et al. |
| 5,837,442 A | 11/1998 | Tsang |
| 5,843,761 A | 12/1998 | Barnett et al. |
| 5,854,033 A | 12/1998 | Lizardi |
| 5,882,856 A | 3/1999 | Shuber |
| 5,958,349 A | 9/1999 | Petersen et al. |
| 6,040,138 A | 3/2000 | Lockhart et al. |
| 6,057,105 A | 5/2000 | Hoon et al. |
| 6,183,960 B1 | 2/2001 | Lizardi |
| 6,210,884 B1 | 4/2001 | Lizardi |
| 6,245,517 B1 | 6/2001 | Chen et al. |
| 6,251,601 B1 | 6/2001 | Bao et al. |
| 6,261,776 B1 | 7/2001 | Pirrung et al. |
| 6,306,643 B1 | 10/2001 | Gentalen et al. |
| 6,309,823 B1 | 10/2001 | Cronin et al. |
| 6,344,329 B1 | 2/2002 | Lizardi |
| 6,346,413 B1 | 2/2002 | Fodor et al. |
| 6,374,684 B1 | 4/2002 | Dority et al. |
| 6,403,037 B1 | 6/2002 | Chang et al. |
| 6,406,844 B1 | 6/2002 | Pirrung et al. |
| 6,416,952 B1 | 7/2002 | Pirrung et al. |
| 6,431,476 B1 | 8/2002 | Taylor et al. |
| 6,440,725 B1 | 8/2002 | Pourahmadi et al. |
| 7,101,663 B2 | 9/2006 | Godfrey et al. |
| 2001/0051344 A1* | 12/2001 | Shalon et al. .................. 435/6 |
| 2006/0068418 A1* | 3/2006 | Godfrey et al. .................. 435/6 |

FOREIGN PATENT DOCUMENTS

| | | |
|---|---|---|
| EP | 1050587 | 11/2000 |
| WO | WO 95/11687 | 5/1995 |
| WO | WO 98/08970 | 3/1998 |
| WO | WO 99/13104 | 3/1999 |
| WO | WO 00/44774 | 8/2000 |
| WO | WO 00/72970 | 12/2000 |
| WO | WO 00/73412 | 12/2000 |
| WO | WO 00/73413 | 12/2000 |
| WO | WO 01/01129 | 1/2001 |
| WO | WO 01/45845 | 6/2001 |
| WO | WO 01/57253 | 8/2001 |
| WO | WO 01/84463 | 11/2001 |
| WO | WO 02/18902 | 3/2002 |
| WO | WO 02/052030 | 7/2002 |
| WO | WO 02/070751 | 9/2002 |
| WO | WO 03/055973 | 7/2003 |
| WO | WO 03/072253 | 9/2003 |
| WO | WO 03/077055 | 9/2003 |
| WO | WO 2004/048931 | 6/2004 |

OTHER PUBLICATIONS

Enard W et al. 'Intra- and interspecific variation in primate gene expression patterns.' Science. Apr. 12, 2002;296(5566):340-3.*
Thisted RA (1998) 'What is a P-value?' available online at www.stat.uchicago.edu/~thisted, pp. 1-6.*
Juppner H 'Functional properties of the PTH/PTHrP receptor.' Bone. Aug.1995; 17(2 Suppl):39S-42S.*
Cheung VG et al 'Natural variation in human gene expression assessed in lymphoblastoid cells.' Nat Genet. Mar. 2003;33(3):422-5.*
HuGeneFL Array from www.affymetrix.com, p. 1.*
Details for HUGENEFL:M93036__AT, from www.affymetrix.com, pp. 1-5.*
Details for HUGENEFL:M76482__AT, from www.affymetrix.com, pp. 1-3.*
de Vos S et al 'Gene expression profile of serial samples of transformed B-cell lymphomas.' Lab Invest. Feb. 2003;83(2):271-85.*
ABI Prism 7700 Sequence Detection System User Bulletin #5, "Multiplex PCR with TaqMan VIC Probes," Applied Biosystems (1998/2001).
Baner, Johan et al. "Signal amplification of padlock probes by rolling circle replication," Nucleic Acids Research (1998), vol. 26, No. 22, pp. 5073-5078.

(Continued)

*Primary Examiner*—Stephen Kapushoc
(74) *Attorney, Agent, or Firm*—Hirshman Law, LLC; Jesse A. Hirshman

(57) ABSTRACT

Methods for identifying expression of markers indicative of the presence of esophageal, a squamous cell cancer, a squamous cell cancer of the head and neck, colon cancer and melanoma are provided. Also provided are articles of manufacture useful in such methods and compositions containing primers and probes useful in such methods.

15 Claims, 32 Drawing Sheets

OTHER PUBLICATIONS

Bercovich, Dani et al. "Quantitative Ratio of Primer Pairs and Annealing Temperature Affecting PCR Products in Duplex Amplification," BioTechniques (Oct. 1999), vol. 27, pp. 762-770.

Braun, D. et al. "Exponential DNA Repliction by Laminar Convection," Physical Review Letters, 91:158103.

Brink, A. A. T. P. et al. "Nucleic Acid Sequence-Based Amplification, a New Method for Analysis of Spliced and Unspliced [EBV] . . . " Journal of Clinical Microbiology (Nov. 1998), pp. 3164-3169.

Canter, David et al., "On-Chip Amplification of Genomic DNA with Short Tandem Repeat and Single Nucleotide Polymorphism Analysis," Nangoen, Inc., San Diego, CA.

Christian, Allen T. et al. "Detection of DNA point mutations and mRNA expression levels by rolling circle amplification in individual cells," PNAS (Dec. 2001), vol. 98, No. 25, pp. 14238-14243.

DeBaar, Michel P. et al. "Single Rapid Real-Time Monitored Isothermal RNA Amplification Assay for Quantification of [HIV] Type 1 . . . " Journal of Clinical Microbiology (Apr. 2001), pp. 1378-1384.

DeBarr, M.P. et al. "One-Tube Real-Time Isothermal Amplification Assay To Identify and Distinguish [HIV] Type 1 Subtypes . . . "Journal of Clinical Microbiology (May 2001), pp. 1895-1902.

Demidov, Vadim V., "Rolling-circle ampliction in DNA diagnostics: the power of simplicity," Future Drugs Ltd., Expert Rev. Mol. Diagn. (Nov. 2002) 2 (6):542-548.

Dessau, R. B. et al. "Coronaviruses in spinal fluid of patients with acute monosymptomatic optic neuritis," Acta Neurol Scand (1999), vol. 100, pp. 88-91.

Efron, B. and Tibshirani, R.J. An Introduction to the Bootstrap. Boca Raton: Chapman and Hall, 1993: 247-252.

Godfrey, T.E. et al. "Prognostic Value of Quantitative Reverse Transcription-Polymerase Chain Reaction . . . " Clinical Cancer Research (Dec. 2001), vol. 7, pp. 4041-4048.

Greijer, Astrid E. et al. "Multiplex real-time NASBA for monitoring expression dynamics of human cytomegalovirus encoded IE1 and pp67 RNA," Journal of Clinical Virology (2002) vol. 24, pp. 57-66.

Harris, Eva et al. "Typing of Dengue Viruses in Clinical Specimens and Mosquitoes by Single-Tube Multiplex Reverse Transcriptase PCR," Journal of Clinical Microbiology (Sep. 1998), pp. 2634-2639.

Hoshikawa, Yasushi, et al. "Hypoxia induces different genes in the lungs of rates compared with mice," Phyisical Genomics (Dec. 3, 2002). vol. 10, p. 1152.

Krishnan, Madhavi, et al. "PCR in Rayleigh-Benard Convection Cell," Science (Oct. 2002), vol. 298, p. 793.

Leone, G. et al. "Molecular beacon probes combined with amplification by NASBA enable homogeneous, real-time detection . . . " Nucleic Acids Research (1998), vol. 26, No. 9, pp. 2150-2155.

Little, Michael C. et al. "Molecular Diagnostics and Genetics," Clinical Chemistry (1999) vol. 45, No. 6, pp. 777-784.

Lockley, Andrew K. et al. "Colormetric detection of immobilized PCR products generated on a solid support," Nucleic Acids Research, (1997), vol. 25, No. 6, pp. 1313-1314.

Luketich, James D., et al. "Detection of Micrometastases in Histologically Negative Lymph Nodes in Esophageal Cancer," Ann Thorac Surg (1998); vol. 66, pp. 1715-1718.

Mitas M et al. "Quantitative real-time RT-PCR detection of breast cancer micrometastasis using a multigene marker panel." Int J Cancer 2001; 93(2):162-171.

Miyake, Y.. et al. "Quantification of Micrometastases in Lymph Nodes of Colorectal Cancer Using Real-Time Fluorescence Polymerase Chain Reaction," Int. J. Oncol (Feb. 2000), vol. 16, No. 2, pp. 289-293.

Mondesire, Roy R. et al. "Solid-phase nucleic acid extraction, amplification, and detection," IVD Technology Magazine (May 2000).

Morrison TB et al. "Quantification of low-copy transcripts by continuous SYBR Green I monitoring during amplification," Biotechniques, (Jun. 1998); vol. 24, No. 6, pp. 954-962.

Nagaraju, J. et al. "FISSR-PCR: a simple and sensitive assay for highthroughput genotyping and genetic mapping," Molecular and Cellular Proves (2002) vol. 16, pp. 67-72.

Nallur, Girish et al. "Signal amplification by rolling circle amplification on DNA microarrays," Nucleic Acids Research, (2001) vol. 29, No. 23 e118.

Nilsson, M. et al. "Making Ends Meet in Genetic Analysis Using Padlock Probes," Human Mutation (2002) 19:410-415.

Oehlenschlager, Frank et al."Detection of HIV-1 RNA by nucleic acid sequence-based amplification combined with fluorescence correlation . . . " PNAS (1996) Biochemistry vol. 93, pp. 12811-12816.

Oshima, Akihiro et al. "Cloning, sequencing, and expression of cDNA for human B-glucuronidase," Proc. Natl. Acad. Sci. USA. (Feb. 1987), vol. 84, pp. 685-689.

Raja, S., et al. "Increased Sensitivity of One-Tube, Quantitative RT-PCR," BioTechniques, (Oct. 2000) vol. 29, pp. 702-706.

Roberts CA, Beitsch PD, Litz CE, Hilton DS, Ewing GE, Clifford E et al. "Interpretive disparity among pathologists in breast sentinel lymph node evaluation," Am J Surg 2003; 186(4):324-329.

Schweitzer, Barry et al. "Immunoassays with rolling circle DNA amplification: A versatile platform for ultrasensitive antigen detection," PNAS (Aug. 2000), vol. 97, No. 18, pp. 10113-10119.

Schweitzer, B. et al. "Combining Nucleic Acid Amplification and Detection," Current Opinion in Biotechnology (2002) 12:21-27.

"TaqMan One-Step RT-PCR Master Mix Reagents Kit," Biosystems (1999).

Thomas, David C. et al. "Amplification of Padlock Probes for DNA Diagnostics by Cascade Rolling Circle Amplification or Polymerase Chain Reaction," Arch Pathol Lab Med (Dec. 1999), vol. 123.

Troutt, Anthony B. et al. "Ligation-anchored PCR: A simple amplification technique with single-sided specifity," Proc. Natl. Acad. Sci. USA (Oct. 1992) vol. 89, pp. 9823-9825.

Viehmann, S. et al. "Multiplex PCR—a rapid screening method for detection of gene rearrangements in childhood acute lymphoblastic leukemia," Annals of Hematol (1999) vol. 78, pp. 157-162.

Wu, Dan Y. et al. "The Effect of Temperature and Oligonucleotide Primer Length on the Specifity and Efficiency of Amplification by [PCR]," DNA and Cell Biology (1991) vol. 10, No. 3, 233-238.

Ylitalo, Nathalie et al. "Detection of Genital Human Papillomavirus by Single-Tube Nested PCR and Type-Specific Oligonucleotide Hybridization," Journal of Clinical Microbiology (Jul. 1995), pp. 1822-1828.

Matsuda, Jun-ichi, et al. "Significance of Metastasis Detected by Molecular Techniques in Sentinel Nodes of Patients with Gastrointestinal Cancer," Annals of Surgical Oncology, (2004) vol. 11, No. 3, p. 250S-254S.

Raja, Siva, et al., "Rapid, quantitative reverse transcriptase-polymerase chain reaction: Application to intraoperative molecular detection of occult metastases in esophageal cancer," The Journal of Thoracic and Cardiovascular Surgery, (2002), vol. 123, No. 3, pp. 475-483.

Bage, NCBI Accession NM_001187, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

BHCG, NCBI Accession NM_000737, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

BRDT, NCBI Accession NM_001726, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

CEA, NCBI Accession NM_004363, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

CK7, NCBI Accession NM_005556, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

CK14, NCBI Accession NM_000526, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

CK18 NCBI Accession NM_000224, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
CK19, NCBI Accession NM_002276, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
CK20, NCBI Accession NM_019010, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
CTAG1, NCBI Accession NM_001327, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
GAGE1, NCBI Accession NM_001468, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
HTERT, NCBI Accession NM_003219, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
ITGB4, NCBI Accession NM_000213, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
KRTHB1, NCBI Accession NM_002281, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
LDHC, NCBI Accession NM_130852, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
LUNX, NCBI Accession NM_017448, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MAGEA1, NCBI Accession NM_004988, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MAGEA2, NCBI Accession NM_005361, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MAGEA3, NCBI Accession NM_005362, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MAGEA4, NCBI Accession NM_002362, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MAGEA8, NCBI, Accession NM_005364, The NCBI, handbook [Internet]. Bethesda (MD): Natl Lib Med (US), 2002, Ch.18 The RefSeq Project. http://www.ncbi.nlm.nih.gov/entrez/query.fcgi?db=Books.
MAGEA10, NCBI Accession NM_021048, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MAGEA12, NCBI Accession NM_005367, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
c-MET, NCBI Accession NM_000245, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MGB1, NCBI Accession NM_002411, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MGB2, NCBI Accession NM_002407, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
MMP7, NCBI Accession NM_002423, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
NIS, NCBI Accession NM_000453, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
NTS, NCBI Accession NM_006183, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
PIP, NCBI Accession NM_002652, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
PTHrP, NCBI Accession NM_002820, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
PVA, NCBI Accession NM_001944, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
SCCA1, NCBI Accession NM_006919, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
SCCA2, NCBI Accession NM_002974, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
SFTPB, NCBI Accession NM_000542, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
SGY-1, NCBI Accession NM_014419, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
SSX2, NCBI Accession NM_006011, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
SSXu, NCBI Accession NM_001169, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
STX, NCBI Accession NM_019010, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
Survivin, NCBI Accession NM_001168, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
TACSTD1, NCBI Accession NM_002354, The NCBI handbook [Internet]. Bethesda (MD): Natl Lib Med (US), 2002, Ch.18 The RefSeq Project. http://www.ncbi.nlm.nih.gov/entrez/query.fcgi?db=Books.
TM4SF3, NCBI Accession NM_004616, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

TITF1, NCBI Accession NM_003317, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

TYR, NCBI Accession NM_000372, The NCBI handbook [Internet]. Bethesda (MD): Natl Lib Med (US), 2002, Ch.18 The RefSeq Project, http://www.ncbi.nlm.nih.gov/entrez/query.fcgi?db=Books.

Villin 1, NCBI Accession NM_007127, The NCBI handbook [Internet]. Bethesda (MD): Natl Lib Med (US), 2002, Ch.18 The RefSeq Project. http://www.ncbi.nlm.nih.gov/entrez/query.fcgi?db=Books.

Bostick, Peter J., et al. "Limitations of Specific Reverse-Transcriptase Polymerase Chain Reaction Markers in the Detection of Metastses in the Lymph NOdes and Blood of Breast Cancer Patients," Journal of Clinical Oncology, Aug. 1998, vol. 16, No. 8, pp. 2632-2640.

Cheung, Vivian G., et al. "Natural Variation in human gene expression assessed in lymphoblastoid cells." Nature Genetics, Mar. 2003, vol. 33, pp. 422-425.

Godfrey, Tony E., et al. "Prognostic Value of Quantitative Reverse Transcription-Polymerase Chain Reaction in Lymph Node-Negative Esophageal Cancer Patients1." Clinical Cancer Research, Dec. 2001, vol. 7, pp. 4041-4048.

Jiao, Xiaolong, MD "Clinical Significance of Micrometastasis in Lung and Esophageal Cancer: A New Paradigm in Thoracic Oncology." Elsevier Science Inc., The Society of Thoracic Surgeons, (2002), Vo. 74, pp. 278-284.

Nakanishi, Hayao, et al. "Rapid Quantitative Detection of Carcinoembryonic Antigen-Expressing Free Tumor cells in the Peritoneal Cavity of Gastric-Cancer Patients with Real-Time RT-PCR on the Lightcycler", Int. J. Cancer (Pred. Oncol.) 2000, vol. 89, pp. 411-417.

Silva, J M, et al. "Detection of epithelial tumour RNA in the plasma of colon cancer patients is associated with advanced stages and circulating tumour cells." Gut 2002; vol. 50, pp. 530-534.

* cited by examiner

CDX1 cDNA Sequence (SEQ ID NO: 1)

```
   1 aggtgagcgg ttgctcgtcg tcggggcggc cggcagcggc ggctccaggg cccagcatgc
  61 gcgggggacc ccgcggccac catgtatgtg ggctatgtgc tggacaagga ttcgcccgtg
 121 taccccggcc cagccaggcc agccagcctc ggcctgggcc cggcaaacta cggccccccg
 181 gccccgcccc cggcgccccc gcagtacccc gacttctcca gctactctca cgtggagccg
 241 gccccgcgc ccccgacggc ctgggggcg cccttccctg cgccaagga cgactgggcc
 301 gccgcctacg gcccgggccc cgcggcccct gccgccagcc cagcttcgct ggcattcggg
 361 cccctccag actttagccc ggtgccggcg ccccctgggc ccggcccggg cctcctggcg
 421 cagcccctcg ggggcccggg cacaccgtcc tcgcccggag cgcagaggcc gacgccctac
 481 gagtggatgc ggcgcagcgt ggcggccgga ggcggcggtg gcagcggtaa gactcggacc
 541 aaggacaagt accgcgtggt ctacaccgac caccaacgcc tggagctgga aaggagttt
 601 cattacagcc gttacatcac aatccggcgg aaatcagagc tggctgccaa tctggggctc
 661 actgaacggc aggtgaagat ctggttccaa aaccggcggg caaaggagcg caaagtgaac
 721 aagaagaaac agcagcagca acagccccca cagccgccga tggcccacga catcacggcc
 781 accccagccg gccatccct ggggggcctg tgtcccagca caccagcct cctggccacc
 841 tcctctccaa tgcctgtgaa agaggagttt ctgccatagc cccatgccca gcctgtgcgc
 901 cggggaccct ggggactcgg gtgctgggag tgtggctcct gtgggcccag gaggtctggt
 961 ccgagtctca gccctgacct tctgggacat ggtggacagt cacctatcca ccctctgcat
1021 ccccttggcc cattgtgtgc agtaagcctg ttggataaag accttccagc tcctgtgttc
1081 tagacctctg ggggataagg gagtccaggg tggatgatct caatctcccg tgggcatctc
1141 aagccccaaa tggttggggg aggggcctag acaaggctcc aggccccacc tcctcctcca
1201 tacgttcaga ggtgcagctg gaggcctgtg tggggaccac actgatcctg gagaaaggg
1261 atggagctga aaaagatgga atgcttgcag agcatgacct gaggagggag gaacgtggtc
1321 aactcacacc tgcctcttct gcagcctcac ctctacctgc ccccatcata agggcactga
1381 gcccttccca ggctggatac taagcacaaa gcccatagca ctgggctctg atggctgctc
1441 cactgggtta cagaatcaca gccctcatga tcattctcag tgagggctct ggattgagag
1501 ggaggccctg ggaggagaga aggggcaga tcttccctaa ccaggtttct acaccccgc
1561 caggctgccc atcagggccc agggagcccc cagaggactt tattcggacc aagcagagct
1621 cacagctgga caggtgttgt atatagagtg gaatctcttg gatgcagctt caagaataaa
1681 ttttcttct cttttcaaa
```

Fig. 1

CEA cDNA Sequence (SEQ ID NO: 2)

```
   1 ctcagggcag agggaggaag gacagcagac cagacagtca cagcagcctt gacaaaacgt
  61 tcctggaact caagctcttc tccacagagg aggacagagc agacagcaga gaccatggag
 121 tctccctcgg cccctcccca cagatggtgc atccctggc agaggctcct gctcacagcc
 181 tcacttctaa ccttctggaa cccgcccacc actgccaagc tcactattga atccacgccg
 241 ttcaatgtcg cagaggggaa ggaggtgctt ctacttgtcc acaatctgcc ccagcatctt
 301 tttggctaca gctggtacaa aggtgaaaga gtggatggca accgtcaaat tataggatat
 361 gtaataggaa ctcaacaagc tacccaggg cccgcataca gtggtcgaga gataatatac
 421 cccaatgcat ccctgctgat ccagaacatc atccagaatg acacaggatt ctacacccta
 481 cacgtcataa agtcagatct tgtgaatgaa gaagcaactg ccagttccg ggtatacccg
 541 gagctgccca gccctccat ctccagcaac aactccaaac ccgtggagga caaggatgct
 601 gtggccttca cctgtgaacc tgagactcag gacgcaacct acctgtggtg ggtaaacaat
 661 cagagcctcc cggtcagtcc caggctgcag ctgtccaatg caacaggac cctcactcta
 721 ttcaatgtca caagaaatga cacagcaagc tacaaatgtg aaacccagaa cccagtgagt
 781 gccaggcgca gtgattcagt catcctgaat gtcctctatg gccggatgc ccccaccatt
 841 tcccctctaa acacatctta cagatcaggg gaaaatctga acctctcctg ccacgcagcc
 901 tctaacccac ctgcacagta ctcttggttt gtcaatggga ctttccagca atccacccaa
 961 gagctcttta tccccaacat cactgtgaat aatagtggat cctatacgtg ccaagcccat
1021 aactcagaca ctggcctcaa taggaccaca gtcacgacga tcacagtcta tgcagagcca
1081 cccaaaccct tcatcaccag caacaactcc aacccgtgg aggatgagga tgctgtagcc
1141 ttaacctgtg aacctgagat tcagaacaca acctacctgt ggtgggtaaa taatcagagc
1201 ctcccggtca gtcccaggct gcagctgtcc aatgacaaca ggaccctcac tctactcagt
1261 gtcacaagga atgatgtagg accctatgag tgtggaatcc agaacgaatt aagtgttgac
1321 cacagcgacc cagtcatcct gaatgtcctc tatggcccag cgaccccac catttccccc
1381 tcatacacct attaccgtcc aggggtgaac ctcagcctct cctgccatgc agcctctaac
1441 ccacctgcac agtattcttg gctgattgat gggaacatcc agcaacacac acaagagctc
1501 tttatctcca acatcactga aagaacagc ggactctata cctgccaggc aataactca
1561 gccagtggcc acagcaggac tacagtcaag acaatcacag tctctgcgga gctgcccaag
1621 ccctccatct ccagcaacaa ctccaaaccc gtggaggaca aggatgctgt ggccttcacc
1681 tgtgaacctg aggctcagaa cacaacctac ctgtggtggg taaatggtca gagcctccca
1741 gtcagtccca ggctgcagct gtccaatggc aacaggaccc tcactctatt caatgtcaca
1801 agaaatgacg caagagccta tgtatgtgga atccagaact cagtgagtgc aaaccgcagt
1861 gacccagtca ccctggatgt cctctatggg ccggacaccc ccatcatttc cccccagac
```

Fig. 2/1

```
1921 tcgtcttacc tttcgggagc gaacctcaac ctctcctgcc actcggcctc taacccatcc
1981 ccgcagtatt cttggcgtat caatgggata ccgcagcaac acacacaagt tctctttatc
2041 gccaaaatca cgccaaataa taacgggacc tatgcctgtt ttgtctctaa cttggctact
2101 ggccgcaata attccatagt caagagcatc acagtctctg catctggaac ttctcctggt
2161 ctctcagctg gggccactgt cggcatcatg attggagtgc tggttggggt tgctctgata
2221 tagcagccct ggtgtagttt cttcatttca ggaagactga cagttgtttt gcttcttcct
2281 taaagcattt gcaacagcta cagtctaaaa ttgcttcttt accaaggata tttacagaaa
2341 agactctgac cagagatcga gaccatccta gccaacatcg tgaaacccca tctctactaa
2401 aaatacaaaa atgagctggg cttggtggcg cgcacctgta gtcccagtta ctcgggaggc
2461 tgaggcagga gaatcgcttg aacccgggag gtggagattg cagtgagccc agatcgcacc
2521 actgcactcc agtctggcaa cagagcaaga ctccatctca aaagaaaag aaaagaagac
2581 tctgacctgt actcttgaat acaagtttct gataccactg cactgtctga gaatttccaa
2641 aactttaatg aactaactga cagcttcatg aaactgtcca ccaagatcaa gcagagaaaa
2701 taattaattt catgggacta atgaactaa tgaggattgc tgattcttta aatgtcttgt
2761 ttcccagatt tcaggaaact ttttttcttt taagctatcc actcttacag caatttgata
2821 aaatatactt ttgtgaacaa aaattgagac atttacattt tctccctatg tggtcgctcc
2881 agacttggga aactattcat gaatatttat attgtatggt aatatagtta ttgcacaagt
2941 tcaataaaaa tctgctcttt gtataacaga aaaa
```

Fig. 2/2

CK7 cDNA Sequence (SEQ ID NO: 3)

```
   1 acggcgagtg cgcgctcctc ctcgcccgcc gctaggtcca tcccggccca gccaccatgt
  61 ccatccactt cagctccccg gtattcacct cgcgctcagc cgccttctcg ggccgcggcg
 121 cccaggtgcg cctgagctcc gctcgccccg gcggccttgg cagcagcagc ctctacggcc
 181 tcggcgcctc gcggccgcgc gtggccgtgc gctctgccta tgggggcccg gtgggcgccg
 241 gcatccgcga ggtcaccatt aaccagagcc tgctggcccc gctgcggctg gacgccgacc
 301 cctccctcca gcgggtgcgc caggaggaga gcgagcagat caaggccctc aacaacaagt
 361 ttgcctcctt catcgacaag gtgcggtttc tggagcagca gaacaagctg ctggagacca
 421 agtggacgct gctgcaggag cagaagtcgg ccaagagcag ccgcctccca gacatctttg
 481 aggcccagat tgctggcctt cggggtcagc ttgaggcact gcaggtggat ggggccgcc
 541 tggagcaggg gctgcggacg atgcaggatg tggtggagga cttcaagaat aagtacgaag
 601 atgaaattaa ccgccgcaca gctgctgaga tgagtttgt ggtcctgaag aaggatgtgg
 661 atgctgccta catgagcaag gtggagctgg aggccaaggt ggatgccctg aatgatgaga
 721 tcaacttcct caggaccctc aatgagacgg agttgacaga gctgcagtcc cagatctccg
 781 acacatctgt ggtgctgtcc atggacaaca gtcgctccct ggacctggac ggcatcatcg
 841 ctgaggtcaa ggcacagtat gaggagatgg ccaaatgcag ccgggctgag ctgaagcct
 901 ggtaccagac caagtttgag accctccagg cccaggctgg aagcatggg gacgacctcc
 961 ggaatacccg gaatgagatt tcagagatga ccgggccat ccagaggctg caggctgaga
1021 tcgacaacat caagaaccag cgtgccaagt tggaggccgc cattgccgag gctgaggagt
1081 gtggggagct ggcgctcaag gatgctcgtg ccaagcagga ggagctggaa gccgccctgc
1141 agcgggccaa gcaggatatg gcacggcagc tgcgtgagta ccaggaactc atgagcgtga
1201 agctggccct ggacatcgag atcgccacct accgcaagct gctggagggc gaggagagcc
1261 ggttggctgg agatggagtg ggagccgtga atatctctgt gatgaattcc actggtggca
1321 gtagcagtgg cggtggcatt gggctgaccc tcggggaac catgggcagc aatgccctga
1381 gcttctccag cagtgcgggt cctgggctcc tgaaggctta ttccatccgg accgcatccg
1441 ccagtcgcag gagtgcccgc gactga
```

Fig. 3

CK19 cDNA Sequence (SEQ ID NO: 4)

```
   1 cgcccctgac accattcctc ccttcccccc tccaccggcc gcgggcataa aaggcgccag
  61 gtgagggcct cgccgctcct cccgcgaatc gcagcttctg agaccagggt tgctccgtcc
 121 gtgctccgcc tcgccatgac ttcctacagc tatcgccagt cgtcggccac gtcgtccttc
 181 ggaggcctgg gcggcggctc cgtgcgtttt gggccggggg tcgcctttcg cgcgcccagc
 241 attcacgggg gctccggcgg ccgcggcgta ccgtgtcct ccgccgctt tgtgtcctcg
 301 tcctcctcgg gggcctacgg cggcggctac ggcggcgtcc tgaccgcgtc cgacgggctg
 361 ctggcgggca acgagaagct aaccatgcag aacctcaacg accgcctggc ctcctacctg
 421 gacaaggtgc gcgccctgga ggcggccaac ggcgagctag aggtgaagat ccgcgactgg
 481 taccagaagc aggggcctgg gccctcccgc gactacagcc actactacac gaccatccag
 541 gacctgcggg acaagattct ggtgccacc attgagaact ccaggattgt cctgcagatc
 601 gacaatgccc gtctggctgc agatgacttc gaaccaagt ttgagacgga acaggctctg
 661 cgcatgagcg tggaggccga catcaacggc ctgcgcaggg tgctggatga gctgaccctg
 721 gccaggaccg acctggagat gcagatcgaa ggcctgaagg aagagctggc ctacctgaag
 781 aagaaccatg aggaggaaat cagtacgctg aggggccaag tgggaggcca ggtcagtgtg
 841 gaggtggatt ccgctccggg caccgatctc gccaagatcc tgagtgacat gcgaagccaa
 901 tatgaggtca tggccgagca gaaccggaag gatgctgaag cctggttcac cagccggact
 961 gaagaattga accgggaggt cgctggccac acggagcagc tccagatgag caggtccgag
1021 gttactgacc tgcggcgcac ccttcagggt cttgagattg agctgcagtc acagctgagc
1081 atgaaagctg ccttggaaga cactggca gaaacggagg cgcgctttgg agcccagctg
1141 gcgcatatcc aggcgctgat cagcggtatt gaagcccagc tgggcgatgt gcgagctgat
1201 agtgagcggc agaatcagga gtaccagcgg ctcatggaca tcaagtcgcg gctggagcag
1261 gagattgcca cctaccgcag cctgctcgag ggacaggaag atcactacaa caatttgtct
1321 gcctccaagg tcctctgagg cagcaggctc tggggcttct gctgtccttt ggagggtgtc
1381 ttctgggtag agggatggga aggaagggac ccttacccc ggctcttctc ctgacctgcc
1441 aataaaaatt tatggtccaa gggaaaaaaa aaaaaaaaa aaaaaaaaa aaaaaaaaa
1501 aaaaaaaaaa aaa
```

Fig. 4

CK20 cDNA Sequence (SEQ ID NO: 5)

```
   1 caaccatcct gaagctacag gtgctccctc ctggaatctc caatggattt cagtcgcaga
  61 agcttccaca gaagcctgag ctcctccttg caggcccctg tagtcagtac agtgggcatg
 121 cagcgcctcg ggacgacacc cagcgtttat gggggtgctg gaggccgggg catccgcatc
 181 tccaactcca gacacacggt gaactatggg agcgatctca caggcggcgg ggacctgttt
 241 gttggcaatg agaaaatggc catgcagaac ctaaatgacc gtctagcgag ctacctagaa
 301 aaggtgcgga ccctggagca gtccaactcc aaacttgaag tgcaaatcaa gcagtggtac
 361 gaaaccaacg ccccgagggc tggtcgcgac tacagtgcat attacagaca aattgaagag
 421 ctgcgaagtc agattaagga tgctcaactg caaaatgctc ggtgtgtcct gcaaattgat
 481 aatgctaaac tggctgctga ggacttcaga ctgaagtatg agactgagag aggaatacgt
 541 ctaacagtgg aagctgatct ccaaggcctg aataaggtct tgatgaccta accctacat
 601 aaaacagatt tggagattca aattgaagaa ctgaataaag acctagctct cctcaaaaag
 661 gagcatcagg aggaagtcga tggcctacac aagcatctgg caacactgt caatgtggag
 721 gttgatgctg ctccaggcct gaaccttggc gtcatcatga tgaaatgag gcagaagtat
 781 gaagtcatgg cccagaagaa ccttcaagag gccaaagaac agtttgagag acagactgca
 841 gttctgcagc aacaggtcac agtgaatact gaagaattaa aggaactga ggttcaacta
 901 acggagctga gacgcacctc ccagagcctt gagatagaac tccagtccca tctcagcatg
 961 aaagagtctt tggagcacac tctagaggag accaaggccc gttacagcag ccagttagcc
1021 aacctccagt cgctgttgag ctctctggag gcccaactga tgcagattcg gagtaacatg
1081 gaacgccaga caacgaata ccatatcctt cttgacataa agactcgact tgaacaggaa
1141 attgctactt accgccgcct tctggaagga gaagacgtaa aaactacaga atatcagtta
1201 agcaccctgg aagagagaga tataaagaaa accaggaaga ttaagacagt cgtgcaagaa
1261 gtagtggatg caaggtcgt gtcatctgaa gtcaaagagg tggaagaaaa tatctaaata
1321 gctaccagaa ggagatgctg ctgaggtttt gaaagaaatt tggctataat cttatctttg
1381 ctccctgcaa gaaatcagcc ataagaaagc actattaata ctctgcagtg attagaaggg
1441 gtggggtggc gggaatccta tttatcagac tctgtaattg aatataaatg ttttactcag
1501 aggagctgca aattgcctgc aaaaatgaaa tccagtgagc actagaatat ttaaaacatc
1561 attactgcca tctttatcat gaagcacatc aattacaagc tgtagaccac ctaatatcaa
1621 tttgtaggta atgttcctga aaattgcaat acatttcaat tatactaaac ctcacaaagt
1681 agaggaatcc atgtaaattg caaataaacc actttctaat ttttcctgt ttctgaaaaa
1741 aaaaaaaaaa aaaaaaaaaa aaaaaaaaaa aaaaaaaaaa aaaaaaaaaa aaaaaaaaa
1801 aaaaaaaaaa aaaaaaa
```

Fig. 5

MAGEA1 cDNA Sequence (SEQ ID NO: 6)

```
   1 cgtagagttc ggccgaagga acctgaccca ggctctgtga ggaggcaagg ttttcagggg
  61 acaggccaac ccagaggaca ggattccctg gaggccacag aggagcacca aggagaagat
 121 ctgcctgtgg gtcttcattg cccagctcct gcccacactc ctgcctgctg ccctgacgag
 181 agtcatcatg tctcttgagc agaggagtct gcactgcaag cctgaggaag cccttgaggc
 241 ccaacaagag gccctgggcc tggtgtgtgt gcaggctgcc gcctcctcct cctctcctct
 301 ggtcctgggc accctggagg aggtgcccac tgctgggtca acagatcctc cccagagtcc
 361 tcagggagcc tccgcctttc ccactaccat caacttcact cgacagaggc aacccagtga
 421 gggttccagc agccgtgaag aggagggggcc aagcacctct tgtatcctgg agtccttgtt
 481 ccgagcagta atcactaaga aggtggctga tttggttggt tttctgctcc tcaaatatcg
 541 agccagggag ccagtcacaa aggcagaaat gctggagagt gtcatcaaaa attacaagca
 601 ctgtttttcct gagatcttcg gcaaagcctc tgagtccttg cagctggtct tggcattga
 661 cgtgaaggaa gcagacccca ccggccactc ctatgtcctt gtcacctgcc taggtctctc
 721 ctatgatggc ctgctgggtg ataatcagat catgcccaag acaggcttcc tgataattgt
 781 cctggtcatg attgcaatgg agggcggcca tgctcctgag gaggaaatct gggaggagct
 841 gagtgtgatg gaggtgtatg atgggaggga gcacagtgcc tatggggagc ccaggaagct
 901 gctcacccaa gatttggtgc aggaaaagta cctggagtac cggcaggtgc cggacagtga
 961 tcccgcacgc tatgagttcc tgtggggtcc aagggccctt gctgaaacca gctatgtgaa
1021 agtccttgag tatgtgatca aggtcagtgc aagagttcgc ttttttcttcc catccctgcg
1081 tgaagcagct ttgagagagg aggaagaggg agtctgagca tgagttgcag ccagggccag
1141 tgggaggggg actgggccag tgcaccttcc agggccgcgt ccagcagctt cccctgcctc
1201 gtgtgacatg aggcccattc ttcactctga agagcggt cagtgttctc agtagtaggt
1261 ttctgttcta ttgggtgact tggagattta tctttgttct cttttggaat tgttcaaatg
1321 ttttttttta agggatggtt gaatgaactt cagcatccaa gttatgaat gacagcagtc
1381 acacagttct gtgtatatag tttaaggta agagtcttgt gttttattca gattgggaaa
1441 tccattctat tttgtgaatt gggataataa cagcagtgga ataagtactt agaaatgtga
1501 aaaatgagca gtaaaataga tgagataaag aactaaagaa attaagagat agtcaattct
1561 tgctttatac ctcagtctat tctgtaaaat ttttaaagat atatgcatac ctggatttcc
1621 ttggcttctt tgagaatgta agagaaatta aatctgaata aagaattctt cctgttaaaa
1681 aaaaaaaaa aaaaaaaaa aaaaaaaaa aaaaaaaaa aa
```

Fig. 6

MAGEA3 cDNA Sequence (SEQ ID NO: 7)

```
   1 gagattctcg ccctgagcaa cgagcgacgg cctgacgtcg gcggagggaa gccggcccag
  61 gctcggtgag gaggcaaggt tctgagggga caggctgacc tggaggacca gaggccccg
 121 gaggagcact gaaggagaag atctgccagt gggtctccat tgcccagctc ctgcccacac
 181 tcccgcctgt tgccctgacc agagtcatca tgcctcttga gcagaggagt cagcactgca
 241 agcctgaaga aggccttgag gcccgaggag aggccctggg cctggtgggt gcgcaggctc
 301 ctgctactga ggagcaggag gctgcctcct cctcttctac tctagttgaa gtcaccctgg
 361 gggaggtgcc tgctgccgag tcaccagatc ctccccagag tcctcaggga gcctccagcc
 421 tccccactac catgaactac cctctctgga ccaatccta tgaggactcc agcaaccaag
 481 aagaggaggg gccaagcacc ttccctgacc tggagtccga gttccaagca gcactcagta
 541 ggaaggtggc cgagttggtt catttctgc tcctcaagta tcgagccagg agccggtca
 601 caaaggcaga atgctgggg agtgtcgtcg gaaattggca gtatttcttt cctgtgatct
 661 tcagcaaagc ttccagttcc ttgcagctgg tctttggcat cgagctgatg gaagtggacc
 721 ccatcggcca cttgtacatc tttgccacct gcctgggcct ctcctacgat ggcctgctgg
 781 gtgacaatca gatcatgccc aaggcaggcc tcctgataat cgtcctggcc ataatcgcaa
 841 gagagggcga ctgtgcccct gaggagaaaa tctgggagga gctgagtgtg ttagaggtgt
 901 ttgaggggag ggaagacagt atcttggggg atcccaagaa gctgctcacc caacatttcg
 961 tgcaggaaaa ctacctggag taccggcagg tccccggcag tgatcctgca tgttatgaat
1021 tcctgtgggg tccaagggcc ctcgttgaaa ccagctatgt gaaagtcctg caccatatgg
1081 taaagatcag tggaggacct cacatttcct acccaccct gcatgagtgg gttttgagag
1141 aggggaaga gtgagtctga gcacgagttg cagccagggc cagtgggagg gggtctgggc
1201 cagtgcacct tccggggccg catcccttag tttccactgc ctcctgtgac gtgaggccca
1261 ttcttcactc tttgaagcga gcagtcagca ttcttagtag tgggtttctg ttctgttgga
1321 tgactttgag attattcttt gtttcctgtt ggagttgttc aaatgttcct tttaacggat
1381 ggttgaatga gcgtcagcat ccaggtttat gaatgacagt agtcacacat agtgctgttt
1441 atatagttta ggagtaagag tcttgttttt tactcaaatt gggaaatcca ttccattttg
1501 tgaattgtga cataataata gcagtggtaa aagtatttgc ttaaaattgt gagcgaatta
1561 gcaataacat acatgagata actcaagaaa tcaaaagata gttgattctt gccttgtacc
1621 tcaatctatt ctgtaaaatt aaacaaatat gcaaaccagg atttccttga cttctttgag
1681 aatgcaagcg aaattaaatc tgaataaata attcttcctc ttcaaaaaaa aaaaaaaaa
1741 aaaaaaaaa aaa
```

Fig. 7

MAGEA6 cDNA Sequence (SEQ ID NO: 8)

```
   1 agcaacgagc gacggcctga cgtcggcgga gggaagccgg cccaggctcg gtgaggaggc
  61 aaggttctga ggggacaggc tgacctggag gaccagaggc ccccggagga gcactgaagg
 121 agaagatctg ccagtgggtc tccattgccc agctcctgcc cacactcccg cctgttgccc
 181 tgaccagagt catcatgcct cttgagcaga ggagtcagca ctgcaagcct gaagaaggcc
 241 ttgaggcccg aggagaggcc ctgggcctgg tgggtgcgca ggctcctgct actgaggagc
 301 aggaggctgc ctcctcctct tctactctag ttgaagtcac cctgggggag gtgcctgctg
 361 ccgagtcacc agatcctccc cagagtcctc agggagcctc cagcctcccc actaccatga
 421 actaccctct ctggagccaa tcctatgagg actccagcaa ccaagaagag gaggggccaa
 481 gcaccttccc tgacctggag tctgagttcc aagcagcact cagtaggaag gtggccaagt
 541 tggttcattt tctgctcctc aagtatcgag ccagggagcc ggtcacaaag gcagaaatgc
 601 tggggagtgt cgtcggaaat tggcagtact tctttcctgt gatcttcagc aaagcttccg
 661 attccttgca gctggtcttt ggcatcgagc tgatggaagt ggaccccatc ggccacgtgt
 721 acatctttgc cacctgcctg ggcctctcct acgatggcct gctgggtgac aatcagatca
 781 tgcccaagac aggcttcctg ataatcatcc tggccataat cgcaaaagag ggcgactgtg
 841 cccctgagga gaaaatctgg gaggagctga gtgtgttaga ggtgtttgag gggagggaag
 901 acagtatctt cggggatccc aagaagctgc tcacccaata tttcgtgcag gaaaactacc
 961 tggagtaccg gcaggtcccc ggcagtgatc ctgcatgcta tgagttcctg tggggtccaa
1021 gggccctcat tgaaaccagc tatgtgaaag tcctgcacca tatggtaaag atcagtggag
1081 gacctcgcat ttcctaccca ctcctgcatg agtgggcttt gagagagggg gaagagtgag
1141 tctgagcacg agttgcagcc agggccagtg ggaggggggtt tgggccagtg caccttccgg
1201 ggccccatcc cttagttccc actgcctcct gtgacgtgag gcccattctt cactctttga
1261 agcgagcagt cagcattctt agtagtgggt ttctgttctg ttggatgact ttgagattat
1321 tctttgtttc ctgttggagt tgttcaaatg ttcctttaa cggatggttg aatgagcgtc
1381 agcatccagg tttatgaatg acagtagtca cacatagtgc tgtttatata gtttaggagt
1441 aagagtcttg ttttttattc agattgggaa atccattcca ttttgtgaat tgtgacataa
1501 taatagcagt ggtaaaagta tttgcttaaa attgtgagcg aattagcaat aacatacatg
1561 agataactca agaaatcaaa agatagttga ttcttgcctt gtacctcaat ctattctgta
1621 aaattaaaca aatatgcaaa ccaggatttc cttgacttct ttgagaatgc aagcgaaatt
1681 aaatctgaat aaataattaa aaaaaaaaaa aaaaaaaaa aaa
```

Fig. 8

MART1 cDNA Sequence (SEQ ID NO: 9)

```
   1 agcagacaga ggactctcat taaggaaggt gtcctgtgcc ctgaccctac aagatgccaa
  61 gagaagatgc tcacttcatc tatggttacc ccaagaaggg gcacggccac tcttacacca
 121 cggctgaaga ggccgctggg atcggcatcc tgacagtgat cctgggagtc ttactgctca
 181 tcggctgttg gtattgtaga agacgaaatg gatacagagc cttgatggat aaaagtcttc
 241 atgttggcac tcaatgtgcc ttaacaagaa gatgcccaca agaagggttt gatcatcggg
 301 acagcaaagt gtctcttcaa gagaaaaact gtgaacctgt ggttcccaat gctccacctg
 361 cttatgagaa actctctgca gaacagtcac caccacctta ttcaccttaa gagccagcga
 421 gacacctgag acatgctgaa attatttctc tcacactttt gcttgaattt aatacagaca
 481 tctaatgttc tcctttggaa tggtgtagga aaaatgcaag ccatctctaa taataagtca
 541 gtgttaaaat tttagtaggt ccgctagcag tactaatcat gtgaggaaat gatgagaaat
 601 attaaattgg gaaaactcca tcaataaatg ttgcaatgca tgatactatc tgtgccagag
 661 gtaatgttag taaatccatg gtgttatttt ctgagagaca gaattcaagt gggtattctg
 721 gggccatcca atttctcttt acttgaaatt tggctaataa caaactagtc aggttttcga
 781 accttgaccg acatgaactg tacacagaat tgttccagta ctatggagtg ctcacaaagg
 841 atactttac aggttaagac aaagggttga ctggcctatt tatctgatca agaacatgtc
 901 agcaatgtct ctttgtgctc taaaattcta ttatactaca ataatatatt gtaaagatcc
 961 tatagctctt ttttttgag atggagtttc gcttttgttg cccaggctgg agtgcaatgg
1021 cgcgatcttg gctcaccata acctccgcct cccaggttca agcaattctc ctgccttagc
1081 ctcctgagta gctgggatta caggcgtgcg ccactatgcc tgactaattt tgtagtttta
1141 gtagagacgg ggtttctcca tgttggtcag gctggtctca aactcctgac ctcaggtgat
1201 ctgcccgcct cagcctccca aagtgctgga attacaggcg tgagccacca cgcctggctg
1261 gatcctatat cttaggtaag acatataacg cagtctaatt acatttcact tcaaggctca
1321 atgctattct aactaatgac aagtattttc tactaaacca gaaattggta gaaggattta
1381 aataagtaaa agctactatg tactgcctta gtgctgatgc ctgtgtactg ccttaaatgt
1441 acctatggca atttagctct cttgggttcc caaatccctc tcacaagaat gtgcagaaga
1501 aatcataaag gatcagagat tctg
```

Fig. 9

PTHrP cDNA Sequence (SEQ ID NO: 10)

```
   1 cctgcatctt tttggaagga ttctttttat aaatcagaaa gtgttcgagg ttcaaaggtt
  61 tgcctcggag cgtgtgaaca ttcctccgct cggttttcaa ctcgcctcca acctgcgccg
 121 cccggccagc atgtctcccc gcccgtgaag cggggctgcc gcctccctgc cgctccggct
 181 gccactaacg acccgccctc gccgccacct ggccctcctg atcgacgaca cacgcacttg
 241 aaacttgttc tcaggtgtgt ggaatcaac tttccggaag caaccagccc accagaggag
 301 gtcccgagcg cgagcggaga cgatgcagcg gagactggtt cagcagtgga gcgtcgcggt
 361 gttcctgctg agctacgcgg tgccctcctg cgggcgctcg gtggagggtc tcagccgccg
 421 cctcaaaaga gctgtgtctg aacatcagct cctccatgac aaggggaagt ccatccaaga
 481 tttacggcga cgattcttcc ttcaccatct gatcgcagaa atccacacag ctgaaatcag
 541 agctacctcg gaggtgtccc ctaactccaa gccctctccc aacacaaaga accacccgt
 601 ccgatttggg tctgatgatg agggcagata cctaactcag gaaactaaca aggtggagac
 661 gtacaaagag cagccgctca agacacctgg gaagaaaaag aaaggcaagc ccgggaaacg
 721 caaggagcag gaaaagaaaa aacggcgaac tcgctctgcc tggttagact ctggagtgac
 781 tgggagtggg ctagaagggg accacctgtc tgacacctcc acaacgtcgc tggagctcga
 841 ttcacggtaa caggcttctc tggcccgtag cctcagcggg gtgctctcag ctgggttttg
 901 gagcctccct tctgccttgg cttggacaaa cctagaattt tctcccttta tgtatctcta
 961 tcgattgtgt agcaattgac agagaataac tcagaatatt gtctgcctta aagcagtacc
1021 cccctaccac acacacccct gtcctccagc accatagaga ggcgctagag cccattcctc
1081 tttctccacc gtcacccaac atcaatcctt taccactcta ccaaataatt tcatattcaa
1141 gcttcagaag ctagtgacca tcttcataat ttgctggaga agtgtgtttc ttcccttac
1201 tctcacacct gggcaaactt tcttcagtgt ttttcatttc ttacgttctt tcacttcaag
1261 ggagaatata gaagcatttg atattatcta caaacactgc agaacagcat catgtcataa
1321 acgattctga gccattcaca ctttttattt aattaaatgt atttaattaa atctcaaatt
1381 tattttaatg taaagaactt aaattatgtt ttaaacacat gccttaaatt tgtttaatta
1441 aatttaactc tggtttctac cagctcatac aaaataaatg gtttctgaaa atgtttaagt
1501 attaacttac aaggatatag gttttctca tgtatctttt tgttcattgg caagatgaaa
1561 taatttttct agggtaatgc cgtaggaaaa ataaaacttc acatttatgt ggcttgttta
1621 tccttagctc acagattgag gtaataatga cactcctaga ctttgggatc aaataactta
1681 gggccaagtc ttgggtctga atttatttaa gttcacaacc tagggcaagt tactctgcct
1741 ttctaagact cacttacatc ttctgtgaaa tataattgta ccaacctcat agagtttggt
1801 gtcaactaaa tgagattata tgtggactaa atatctgtca tatagtaaac actcaataaa
1861 ttgcaacata ttaaaaaaaa a
```

Fig. 10

PVA cDNA Sequence (SEQ ID NO: 11)

```
   1 tttcttaga cattaactgc agacggctgg caggatagaa gcagcggctc acttggactt
  61 tttcaccagg gaaatcagag acaatgatgg ggctcttccc cagaactaca ggggctctgg
 121 ccatcttcgt ggtggtcata ttggttcatg gagaattgcg aatagagact aaaggtcaat
 181 atgatgaaga agagatgact atgcaacaag ctaaaagaag gcaaaaacgt gaatgggtga
 241 aatttgccaa accctgcaga gaaggagaag ataactcaaa aagaaaccca attgccaaga
 301 ttacttcaga ttaccaagca acccagaaaa tcacctaccg aatctctgga gtgggaatcg
 361 atcagccgcc ttttggaatc tttgttgttg acaaaaacac tggagatatt aacataacag
 421 ctatagtcga ccgggaggaa actccaagct tcctgatcac atgtcgggct ctaaatgccc
 481 aaggactaga tgtagagaaa ccacttatac taacggttaa aattttggat attaatgata
 541 tcctccagt attttcacaa caaattttca tgggtgaaat tgaagaaaat agtgcctcaa
 601 actcactggt gatgatacta aatgccacag atgcagatga accaaaccac ttgaattcta
 661 aaattgcctt caaaattgtc tctcaggaac cagcaggcac acccatgttc ctcctaagca
 721 gaaacactgg ggaagtccgt actttgacca attctcttga ccgagagcaa gctagcagct
 781 atcgtctggt tgtgagtggt gcagacaaag atggagaagg actatcaact caatgtgaat
 841 gtaatattaa agtgaaagat gtcaacgata acttcccaat gtttagagac tctcagtatt
 901 cagcacgtat tgaagaaaat attttaagtt ctgaattact tcgatttcaa gtaacagatt
 961 tggatgaaga gtacacagat aattggcttg cagtatattt ctttacctct gggaatgaag
1021 gaaattggtt tgaaatacaa actgatccta gaactaatga aggcatcctg aaagtggtga
1081 aggctctaga ttatgaacaa ctacaaagcg tgaaacttag tattgctgtc aaaaacaaag
1141 ctgaatttca ccaatcagtt atctctcgat accgagttca gtcaacccca gtcacaattc
1201 aggtaataaa tgtaagagaa ggaattgcat tccgtcctgc ttccaagaca tttactgtgc
1261 aaaaaggcat aagtagcaaa aaattggtgg attatatcct gggaacatat caagccatcg
1321 atgaggacac taacaaagct gcctcaaatg tcaaatatgt catgggacgt aacgatggtg
1381 gatacctaat gattgattca aaaactgctg aaatcaaatt tgtcaaaaat atgaaccgag
1441 attctacttt catagttaac aaaacaatca cagctgaggt tctggccata gatgaataca
1501 cgggtaaaac ttctacaggc acgtatatg ttagagtacc cgatttcaat gacaattgtc
1561 caacagctgt cctcgaaaaa gatgcagttt gcagttcttc accttcgtg gttgtctccg
1621 ctagaacact gaataataga tacactggcc cctatacatt tgcactggaa gatcaacctg
1681 taaagttgcc tgccgtatgg agtatcacaa ccctcaatgc tacctcggcc ctcctcagag
1741 cccaggaaca gatacctcct ggagtatacc acatctccct ggtacttaca gacagtcaga
1801 acaatcggtg tgagatgcca cgcagcttga cactggaagt ctgtcagtgt gacaacaggg
1861 gcatctgtgg aacttcttac ccaaccacaa gccctgggac caggtatggc aggccgcact
```

Fig. 11/1

```
1921 cagggaggct ggggcctgcc gccatcggcc tgctgctcct tggtctcctg ctgctgctgt
1981 tggccccect tctgctgttg acctgtgact gtggggcagg ttctactggg ggagtgacag
2041 gtggttttat cccagttcct gatggctcag aaggaacaat tcatcagtgg ggaattgaag
2101 gagcccatcc tgaagacaag gaaatcacaa atatttgtgt gcctcctgta acagccaatg
2161 gagccgattt catggaaagt tctgaagttt gtacaaatac gtatgccaga ggcacagcgg
2221 tggaaggcac ttcaggaatg gaaatgacca ctaagcttgg agcagccact gaatctggag
2281 gtgctgcagg ctttgcaaca gggacagtgt caggagctgc ttcaggattc ggagcagcca
2341 ctggagttgg catctgttcc tcagggcagt ctggaaccat gagaacaagg cattccactg
2401 gaggaaccaa taaggactac gctgatgggg cgataagcat gaattttctg gactcctact
2461 tttctcagaa agcatttgcc tgtgcggagg aagacgatgg ccaggaagca aatgactgct
2521 tgttgatcta tgataatgaa ggcgcagatg ccactggttc tcctgtgggc tccgtgggtt
2581 gttgcagttt tattgctgat gacctggatg acagcttctt ggactcactt ggacccaaat
2641 ttaaaaaact tgcagagata agccttggtg ttgatggtga aggcaaagaa gttcagccac
2701 cctctaaaga cagcggttat gggattgaat cctgtggcca tcccatagaa gtccagcaga
2761 caggatttgt taagtgccag actttgtcag gaagtcaagg agcttctgct ttgtccgcct
2821 ctgggtctgt ccagccagct gtttccatcc ctgaccctct gcagcatggt aactatttag
2881 taacggagac ttactcggct tctggttccc tcgtgcaacc ttccactgca ggctttgatc
2941 cacttctcac acaaaatgtg atagtgacag aaagggtgat ctgtcccatt tccagtgttc
3001 ctgcaacct agctggccca acgcagctac gagggtcaca tactatgctc tgtacagagg
3061 atccttgctc ccgtctaata tgaccagaat gagctggaat accacactga ccaaatctgg
3121 atctttggac taaagtattc aaaatagcat agcaaagctc actgtattgg gctaataatt
3181 tggcacttat tagcttctct cataaactga tcacgattat aaattaaatg tttgggttca
3241 taccccaaaa gcaatatgtt gtcactccta attctcaagt actattcaaa ttgtagtaaa
3301 tcttaaagtt tttcaaaacc ctaaaatcat attcgc
```

Fig. 11/2

SCCA1 cDNA Sequence (SEQ ID NO: 12)

```
   1 ctctctgccc acctctgctt cctctaggaa cacaggagtt ccagatcaca tcgagttcac
  61 catgaattca ctcagtgaag ccaacaccaa gttcatgttc gacctgttcc aacagttcag
 121 aaaatcaaaa gagaacaaca tcttctattc ccctatcagc atcacatcag cattagggat
 181 ggtcctctta ggagccaaag acaacactgc acaacagatt aagaaggttc ttcactttga
 241 tcaagtcaca gagaacacca caggaaaagc tgcaacatat catgttgata ggtcaggaaa
 301 tgttcatcac cagtttcaaa agcttctgac tgaattcaac aaatccactg atgcatatga
 361 gctgaagatc gccaacaagc tcttcggaga aaaaacgtat ctatttttac aggaatattt
 421 agatgccatc aagaaatttt accagaccag tgtggaatct gttgattttg caaatgctcc
 481 agaagaaagt cgaaagaaga ttaactcctg ggtggaaagt caaacgaatg aaaaaattaa
 541 aaacctaatt cctgaaggta atattggcag caataccaca ttggttcttg tgaacgcaat
 601 ctatttcaaa gggcagtggg agaagaaatt aataaagaa gatactaaag aggaaaaatt
 661 ttggccaaac aagaatacat acaagtccat acagatgatg aggcaataca catcttttca
 721 ttttgcctcg ctggaggatg tacaggccaa ggtcctggaa ataccataca aaggcaaaga
 781 tctaagcatg attgtgttgc tgccaaatga aatcgatggt ctccagaagc ttgaagagaa
 841 actcactgct gagaaattga tggaatggac aagtttgcag aatatgagag agacacgtgt
 901 cgatttacac ttacctcggt tcaaagtgga agagagctat gacctcaagg acacgttgag
 961 aaccatggga atggtggata tcttcaatgg ggatgcagac ctctcaggca tgaccgggag
1021 ccgcggtctc gtgctatctg agtcctaca caaggccttt gtggaggtta cagaggaggg
1081 agcagaagct gcagctgcca ccgctgtagt aggattcgga tcatcaccta cttcaactaa
1141 tgaagagttc cattgtaatc accctttcct attcttcata aggcaaaata agaccaacag
1201 catcctcttc tatggcagat tctcatcccc gtagatgcaa ttagtctgtc actccatttg
1261 gaaaatgttc acctgcagat gttctggtaa actgattgct ggcaacaaca gattctcttg
1321 gctcatattt ctttctttc tcatcttgat gatgatcgtc atcatcaaga atttaatgat
1381 taaaatagca tgcctttctc tctttctctt aataagccca catataaatg tacttttct
1441 tccagaaaaa ttctccttga ggaaaaatgt ccaaaataag atgaatcact taataccgta
1501 tcttctaaat ttgaaatata attctgtttg tgacctgttt taaatgaacc aaaccaaatc
1561 atactttttc tttgaattta gcaacctaga aacacacatt tctttgaatt taggtgatac
1621 ctaaatcctt cttatgtttc taaattttgt gattctataa aacacatcat caataaaata
1681 gtgacataaa atca
```

Fig. 12

SCCA2 cDNA Sequence (SEQ ID NO: 13)

```
   1 gggagacaca cacagcctct ctgcccacct ctgcttcctc taggaacaca ggagttccag
  61 atcacatcga gttcaccatg aattcactca gtgaagccaa caccaagttc atgttcgatc
 121 tgttccaaca gttcagaaaa tcaaaagaga acaacatctt ctattcccct atcagcatca
 181 catcagcatt agggatggtc ctcttaggag ccaaagacaa cactgcacaa caaattagca
 241 aggttcttca ctttgatcaa gtcacagaga acaccacaga aaaagctgca acatatcatg
 301 ttgataggtc aggaaatgtt catcaccagt ttcaaaagct tctgactgaa ttcaacaaat
 361 ccactgatgc atatgagctg aagatcgcca acaagctctt cggagaaaag acgtatcaat
 421 ttttacagga atatttagat gccatcaaga aattttacca gaccagtgtg gaatctactg
 481 attttgcaaa tgctccagaa gaaagtcgaa agaagattaa ctcctgggtg aaagtcaaa
 541 cgaatgaaaa aattaaaaac ctatttcctg atgggactat tggcaatgat acgacactgg
 601 ttcttgtgaa cgcaatctat ttcaaagggc agtgggagaa taaatttaaa aagaaaaaca
 661 ctaaagagga aaaattttgg ccaaacaaga atacatacaa atctgtacag atgatgaggc
 721 aatacaattc ctttaatttt gccttgctgg aggatgtaca ggccaaggtc ctggaaatac
 781 catacaaagg caaagatcta agcatgattg tgctgctgcc aaatgaaatc gatggtctgc
 841 agaagcttga agagaaactc actgctgaga attgatgga atggacaagt ttgcagaata
 901 tgagagagac atgtgtcgat ttacacttac ctcggttcaa aatggaagag agctatgacc
 961 tcaaggacac gttgagaacc atgggaatgg tgaatatctt caatggggat gcagacctct
1021 caggcatgac ctggagccac ggtctctcag tatctaaagt cctacacaag gcctttgtgg
1081 aggtcactga ggagggagtg gaagctgcag ctgccaccgc tgtagtagta gtcgaattat
1141 catctccttc aactaatgaa gagttctgtt gtaatcaccc tttcctattc ttcataaggc
1201 aaaataagac caacagcatc ctcttctatg gcagattctc atccccatag atgcaattag
1261 tctgtcactc catttagaaa atgttcacct agaggtgttc tggtaaactg attgctggca
1321 acaacagatt ctcttggctc atatttcttt tctatctcat cttgatgatg atagtcatca
1381 tcaagaattt aatgattaaa atagcatgcc tttctctctt tctcttaata agcccacata
1441 taaatgtact tttccttcca gaaaaatttc ccttgaggaa aaatgtccaa gataagatga
1501 atcatttaat accgtgtctt ctaaatttga aatataattc tgtttctgac ctgttttaaa
1561 tgaaccaaac caaatcatac tttctcttca aatttagcaa cctagaaaca cacatttctt
1621 tgaatttagg tgatacctaa atccttctta tgtttctaaa ttttgtgatt ctataaaaca
1681 catcatcaat aaaataatga ctaaaaaaaa aaaaaaaaaa aaaaaaaaaa aaaaaaaaa
1741 aaaaaaaaaa aacccaaaaa aaaaaaaaaa aaaaaaaaaa aa
```

Fig. 13

TACSTD1 cDNA Sequence (SEQ ID NO: 14)

```
   1 cggcgagcga gcaccttcga cgcggtccgg ggaccccctc gtcgctgtcc tcccgacgcg
  61 gacccgcgtg ccccaggcct cgcgctgccc ggccggctcc tcgtgtccca ctcccggcgc
 121 acgccctccc gcgagtcccg ggcccctccc gcgcccctct tctcggcgcg cgcgcagcat
 181 ggcgccccg caggtcctcg cgttcgggct tctgcttgcc gcggcgacgg cgactttgc
 241 cgcagctcag gaagaatgtg tctgtgaaaa ctacaagctg ccgtaaact gctttgtgaa
 301 taataatcgt caatgccagt gtacttcagt tggtgcacaa aatactgtca tttgctcaaa
 361 gctggctgcc aaatgtttgg tgatgaaggc agaaatgaat ggctcaaaac ttgggagaag
 421 agcaaaacct gaaggggccc tccagaacaa tgatgggctt tatgatcctg actgcgatga
 481 gagcgggctc tttaaggcca agcagtgcaa cggcacctcc acgtgctggt gtgtgaacac
 541 tgctggggtc agaagaacag acaaggacac tgaaataacc tgctctgagc gagtgagaac
 601 ctactggatc atcattgaac taaaacacaa agcaagagaa aaaccttatg atagtaaaag
 661 tttgcggact gcacttcaga aggagatcac aacgcgttat caactggatc aaaaatttat
 721 cacgagtatt ttgtatgaga ataatgttat cactattgat ctggttcaaa attcttctca
 781 aaaaactcag aatgatgtgg acatagctga tgtggcttat tatttgaaa aagatgttaa
 841 aggtgaatcc ttgtttcatt ctaagaaaat ggacctgaca gtaaatgggg aacaactgga
 901 tctggatcct ggtcaaactt aatttatta tgttgatgaa aaagcacctg aattctcaat
 961 gcagggtcta aaagctggtg ttattgctgt tattgtggtt gtggtgatag cagttgttgc
1021 tggaattgtt gtgctggtta tttccagaaa gaagagaatg gcaaagtatg agaaggctga
1081 gataaaggag atgggtgaga tgcatagga actcaatgca taactatata atttgaagat
1141 tatagaagaa gggaaatagc aaatggacac aaattacaaa tgtgtgtgcg tgggacgaag
1201 acatctttga aggtcatgag tttgttagtt taacatcata tatttgtaat agtgaaacct
1261 gtactcaaaa tataagcagc ttgaaactgg ctttaccaat cttgaaattt gaccacaagt
1321 gtcttatata tgcagatcta atgtaaaatc cagaacttgg actccatcgt taaaattatt
1381 tatgtgtaac attcaaatgt gtgcattaaa tatgcttcca cagtaaaatc tgaaaaactg
1441 atttgtgatt gaaagctgcc tttctattta cttgagtctt gtacatacat acttttttat
1501 gagctatgaa ataaaacatt ttaaactg
```

Fig. 14

TYR cDNA Sequence (SEQ ID NO: 15)

```
   1 tattgagttc ttcaaacatt gtagcctctt tatggtctct gagaaataac taccttaaac
  61 ccataatctt taatacttcc taaactttct taataagaga agctctattc ctgacactac
 121 ctctcatttg caaggtcaaa tcatcattag ttttgtagtc tattaactgg gtttgcttag
 181 gtcaggcatt attattacta accttattgt taatattcta accataagaa ttaaactatt
 241 aatggtgaat agagttttc actttaacat aggcctatcc cactggtggg atacgagcca
 301 attcgaaaga aaagtcagtc atgtgctttt cagaggatga agcttaaga taaagactaa
 361 aagtgtttga tgctggaggt gggagtggta ttatataggt ctcagccaag acatgtgata
 421 atcactgtag tagtagctgg aaagagaaat ctgtgactcc aattagccag ttcctgcaga
 481 ccttgtgagg actagaggaa gaatgctcct ggctgttttg tactgcctgc tgtggagttt
 541 ccagacctcc gctggccatt tccctagagc ctgtgtctcc tctaagaacc tgatggagaa
 601 ggaatgctgt ccaccgtgga gcggggacag gagtccctgt ggccagcttt caggcagagg
 661 ttcctgtcag aatatccttc tgtccaatgc accacttggg cctcaatttc ccttcacagg
 721 ggtggatgac cgggagtcgt ggccttccgt cttttataat aggacctgcc agtgctctgg
 781 caacttcatg ggattcaact gtggaaactg caagtttggc ttttggggac caaactgcac
 841 agagagacga ctcttggtga agaaacat cttcgatttg agtgcccag agaaggacaa
 901 attttttgcc tacctcactt tagcaaagca taccatcagc tcagactatg tcatccccat
 961 agggacctat ggccaaatga aaaatggatc aacacccatg tttaacgaca tcaatattta
1021 tgacctcttt gtctggatgc attattatgt gtcaatggat gcactgcttg ggggatctga
1081 aatctggaga gacattgatt ttgcccatga agcaccagct tttctgcctt ggcatagact
1141 cttcttgttg cggtgggaac aagaaatcca aagctgaca ggagatgaaa acttcactat
1201 tccatattgg gactggcggg atgcagaaaa gtgtgacatt tgcacagatg agtacatggg
1261 aggtcagcac cccacaaatc ctaacttact cagcccagca tcattcttct cctcttggca
1321 gattgtctgt agccgattgg aggagtacaa cagccatcag tctttatgca atggaacgcc
1381 cgagggacct ttacggcgta atcctggaaa ccatgacaaa tccagaaccc caaggctccc
1441 ctcttcagct gatgtagaat tttgcctgag tttgacccaa tatgaatctg gttccatgga
1501 taaagctgcc aatttcagct ttagaaatac actggaagga tttgctagtc cacttactgg
1561 gatagcggat gcctctcaaa gcagcatgca caatgccttg cacatctata tgaatggaac
1621 aatgtcccag gtacagggat ctgccaacga tcctatcttc cttcttcacc atgcatttgt
1681 tgacagtatt tttgagcagt ggctccgaag gcaccgtcct cttcaagaag tttatccaga
1741 agccaatgca cccattggac ataaccggga atcctacatg gttccttta taccactgta
1801 cagaaatggt gatttcttta tttcatccaa agatctgggc tatgactata gctatctaca
1861 agattcagac ccagactctt ttcaagacta cattaagtcc tatttggaac aagcgagtcg
```

Fig. 15/1

```
1921 gatctggtca tggctccttg gggcggcgat ggtaggggcc gtcctcactg ccctgctggc
1981 agggcttgtg agcttgctgt gtcgtcacaa gagaaagcag cttcctgaag aaaagcagcc
2041 actcctcatg gagaaagagg attaccacag cttgtatcag agccatttat aaaaggctta
2101 ggcaatagag tagggccaaa aagcctgacc tcactctaac tcaaagtaat gtccaggttc
2161 ccagagaata tctgctggta ttttctgta aagaccattt gcaaaattgt aacctaatac
2221 aaagtgtagc cttcttccaa ctcaggtaga acacacctgt ctttgtcttg ctgttttcac
2281 tcagcccttt taacattttc ccctaagccc atatgtctaa ggaaaggatg ctatttggta
2341 atgaggaact gttatttgta tgtgaattaa agtgctctta tttt
```

Fig. 15/2

VIL1 cDNA Sequence (SEQ ID NO: 16)

```
   1 cattctcccc caggctcact caccatgacc aagctgagcg cccaagtcaa aggctctctc
  61 aacatcacca ccccgggggct gcagatatgg aggatcgagg ccatgcagat ggtgcctgtt
 121 ccttccagca cctttggaag cttcttcgat ggtgactgct acatcatcct ggctatccac
 181 aagacagcca gcagcctgtc ctatgacatc cactactgga ttggccagga ctcatccctg
 241 gatgagcagg gggcagctgc catctacacc acacagatgg atgacttcct gaagggccgg
 301 gctgtgcagc accgcgaggt ccagggcaac gagagcgagg ccttccgagg ctacttcaag
 361 caaggccttg tgatccggaa aggggggcgtg gcttctggca tgaagcacgt ggagaccaac
 421 tcctatgacg tccagaggct gctgcatgtc aagggcaaga ggaacgtggt agctggagag
 481 gtagagatgt cctggaagag tttcaaccga ggggatgttt cctcctgga ccttgggaag
 541 cttatcatcc agtggaatgg accggaaagc acccgtatgg agagactcag gggcatgact
 601 ctggccaagg agatccgaga ccaggagcgg ggagggcgca cctatgtagg cgtggtggac
 661 ggagagaatg aattggcatc cccgaagctg atggaggtga tgaaccacgt gctgggcaag
 721 cgcagggagc tgaaggcggc cgtgcccgac acggtggtgg agccggcact caaggctgca
 781 ctcaaactgt accatgtgtc tgactccgag gggaatctgg tggtgaggga agtcgccaca
 841 cggccactga cacaggacct gctcagtcac gaggactgtt acatcctgga ccaggggggc
 901 ctgaagatct acgtgtggaa aggaagaaa gccaatgagc aggagaagaa gggagccatg
 961 agccatgcgc tgaacttcat caaagccaag cagtacccac caagcacaca ggtggaggtg
1021 cagaatgatg gggctgagtc ggccgtcttt cagcagctct tccagaagtg gacagcgtcc
1081 aaccggacct caggcctagg caaaacccac actgtgggct ccgtggccaa agtggaacag
1141 gtgaagttcg atgccacatc catgcatgtc aagcctcagg tggctgccca gcagaagatg
1201 gtagatgatg gagtggggga agtgcaggtg tggcgcattg agaacctaga gctggtacct
1261 gtggattcca agtggctagg ccacttctat ggggcgact gctacctgct gctctacacc
1321 tacctcatcg gcgagaagca gcattacctg ctctacgttt ggcagggcag ccaggccagc
1381 caagatgaaa ttacagcatc agcttatcaa gccgtcatcc tggaccagaa gtacaatggt
1441 gaaccagtcc agatccgggt cccaatgggc aaggagccac ctcatcttat gtccatcttc
1501 aagggacgca tggtggtcta ccagggaggc acctcccgaa ctaacaactt ggagaccggg
1561 ccctccacac ggctgttcca ggtccaggga actggcgcca acaacaccaa ggcctttgag
1621 gtcccagcgc gggccaattt cctcaattcc aatgatgtct tgtcctcaa gacccagtct
1681 tgctgctatc tatggtgtgg gaagggttgt agcggggacg agcgggagat ggccaagatg
1741 gttgctgaca ccatctcccg gacggagaag caagtggtgg tggaagggca ggagccagcc
1801 aacttctgga tggccctggg tgggaaggcc ccctatgcca acaccaagag actacaggaa
```

Fig. 16/1

```
1861 gaaaacctgg tcatcacccc ccggctcttt gagtgttcca acaagactgg gcgcttcctg
1921 gccacagaga tccctgactt caatcaggat gacttggaag aggatgatgt gttcctacta
1981 gatgtctggg accaggtctt cttctggatt gggaaacatg ccaacgagga ggagaagaag
2041 gccgcagcaa ccactgcaca ggaataccct caagacccatc ccagcgggcg tgaccctgag
2101 accccatca ttgtggtgaa gcagggacac gagccccca ccttcacagg ctggttcctg
2161 gcttgggatc ccttcaagtg gagtaacacc aaatcctatg aggacctgaa ggcggagtct
2221 ggcaacctta gggactggag ccagatcact gctgaggtca caagccccaa agtggacgtg
2281 ttcaatgcta acagcaacct cagttctggg cctctgccca tcttcccct ggagcagcta
2341 gtgaacaagc tgtagagga gctccccgag ggtgtggacc ccagcaggaa ggaggaacac
2401 ctgtccattg aagatttcac tcaggccttt gggatgactc cagctgcctt ctctgctctg
2461 cctcgatgga agcaacaaaa cctcaagaaa gaaaaggac tattttgaga agagtagctg
2521 tggttgtaaa gcagtaccct accctgattg tagggtctca ttttctcacc gatattagtc
2581 ctacaccaat tgaagtgaaa ttttgcagat gtgcctatga gcacaaactt ctgtggcaaa
2641 tgccagtttt gtttaataat gtacctattc cttcagaaag atgataccc aaaaaaaaaa
2701 aa
```

Fig. 16/2

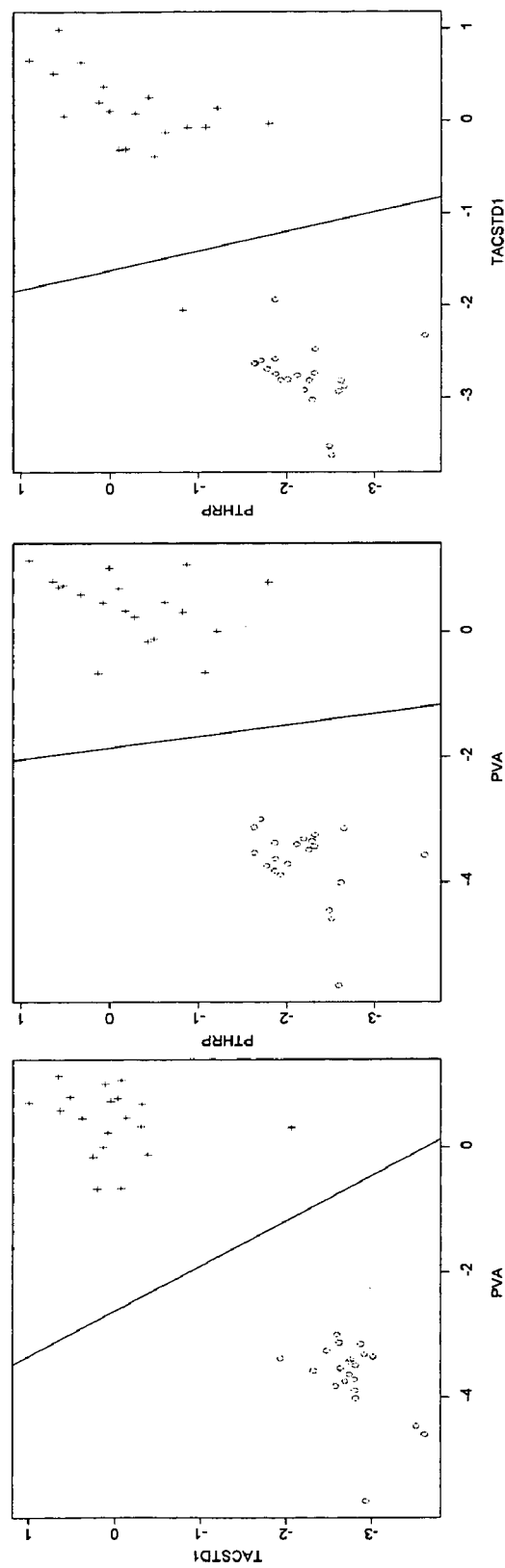

IDENTIFICATION OF MARKERS IN ESOPHAGEAL CANCER, COLON CANCER, HEAD AND NECK CANCER, AND MELANOMA

CROSS REFERENCE TO RELATED APPLICATIONS

This application claims the benefit under 35 U.S.C. §119 (e) to priority U.S. Provisional Patent Application Nos. 60/586,599 and 60/587,019, both filed on Jul. 9, 2004, each of which is incorporated herein by reference in its entirety.

BACKGROUND

1. Field of the Invention

Provided are improved cancer diagnostic methods, along with compositions and apparatus useful in conducting those methods.

2. Description of the Related Art

Early detection of cancer typically leads to increased survival rates. Metastatic lesions commonly are detected by histological techniques, including immunohistochemical techniques. Metastasized cells typically infiltrate the lymph nodes, and, thus in most instances, certain sentinel lymph nodes, lymph nodes where metastasized cells typically first infiltrate, are recognized for each cancer type and are analyzed for the presence of lesions, including micrometastases. Trained histologists often can detect metastatic lesions visually after tissue from a sentinel lymph node is sectioned and stained. Highly trained histologists often can visualize micrometasteses, but the ability to visualize such lesions varies from histologist-to-histologist.

In many surgical procedures to remove tumors, biopsies of sentinel lymph nodes are taken. The surgical procedure is then halted and the excised lymphatic tissue is then analyzed. Once it is determined that the tumor has metastasized, a second, more radical surgical procedure is performed, removing regional lymphatics. A rapid method for identifying tumors is therefore warranted, not only because more assays can be performed in a given time period, thereby increasing laboratory turnaround, but permitting accurate, intraoperative decisions to be made, rather than conducting a second surgical procedure. It is therefore desirable to identify useful diagnostics for malignancies, especially that permit rapid and/or intraoperative detection of lymphatic micrometastases.

SUMMARY

The present invention relates to a diagnostic method for detecting the presence of cancer cells in a patient by identifying the expression of certain markers indicative of the presence of cancer cell.

In one embodiment, the present invention relates to a method of identifying the expression of markers indicative of the presence of esophageal cancer cells in a lymph node of a patient. The method comprises determining if an mRNA species specific to one or more of CEA, CK7, CK19, CK20, VIL1, TACSTD1, and PVA is overabundant in an RNA sample prepared from the lymph node. The overabundance of the mRNA species is indicative of the presence of displaced cells of the esophagus in the lymph node.

In another embodiment, the present invention relates to a method of identifying the expression of markers indicative of the presence of cells of squamous cell carcinoma of the head and neck in a lymph node of a patient. The method comprises determining if an mRNA species specific to one or more of CEA, CK19, PTHrP, PVA, TACSTD1 and SCCA1.2 (SCCA1+SCCA2) is overabundant in an RNA sample prepared from the lymph node. The overabundance of the mRNA species is indicative of the presence of displaced cells of a squamous cell carcinoma of the head and neck in the lymph node.

In still another embodiment, the present invention relates to a method for identifying the expression or markers indicative of the presence of cells of a squamous cell carcinoma in a lymph node of a patient. The method comprises determining if an mRNA species specific to PVA is overabundant in an RNA sample prepared from the lymph node. The overabundance of the mRNA species is indicative of the presence of displaced cells of a squamous cell carcinoma in the lymph node.

In yet another embodiment, the present invention relates to a method for identifying the expression of markers indicative of the presence of colon cancer cells in a lymph node of a patient. The method comprises determining if an mRNA species specific to one or more of CDX1, TACSTD1 and VIL1 is overabundant in an RNA sample prepared from the lymph node. The overabundance of the mRNA species is indicative of the presence of displaced colon cells in the lymph node.

In still another embodiment, the present invention relates to a method for identifying the expression of markers indicative of the presence of melanoma cells in a lymph node of a patient. The method comprises determining if an mRNA species specific to one or more of MAGEA136-plex, MART1, and TYR is overabundant in an RNA sample prepared from the lymph node. The overabundance of the mRNA species is indicative of the presence of melanoma cells in the lymph node.

In yet a further embodiment, the present invention relates to an article of manufacture comprising packaging material and one or more nucleic acids specific to one or more of CEA, CK7, CK19, CK20, VIL1, TACSTD1, and PVA. The packaging material comprises an indicia, for example and without limitation, a writing, illustration, label, tag, book, booklet and/or package insert, indicating that the one or more nucleic acids can be used in a method of identifying expression of markers indicative of the presence of esophageal cancer cells in a lymph node of a patient.

In a still further embodiment, the present invention relates to an article of manufacture comprising packaging material and one or more nucleic acids specific to one or more of CEA, CK19, PTHrP, PVA, TACSTD1 and SCCA1.2. The packaging material comprises an indicia indicating that the one or more nucleic acids can be used in a method of identifying expression of markers indicative of the presence of cells of a squamous cell carcinoma of the head and neck in a lymph node of a patient.

In another embodiment, the present invention relates to an article of manufacture comprising packaging material and one or more nucleic acids specific to one or more of CDX1, TACSTD1 and VIL1. The packaging material comprises an indicia indicating that the one or more nucleic acids can be used in a method of identifying expression of markers indicative of the presence of colon cancer cells in a lymph node of a patient.

In still another embodiment, the present invention relates to an article of manufacture comprising packaging material and one or more nucleic acids specific to one or more of MAGEA136-plex, MART1 and TYR. The packaging material comprises an indicia indicating that the one or more nucleic acids can be used in a method of identifying expression of markers indicative of the presence of melanoma cells in a lymph node of a patient.

In still another embodiment, the present invention relates to an article of manufacture comprising packaging material and one or more nucleic acids specific to PVA. The packaging material comprises an indicia indicating that the one or more nucleic acids can be used in a method of identifying expression of markers indicative of the presence of cells of a squamous cell carcinoma in a lymph node of a patient.

In yet another embodiment, the present invention relates to a composition comprising one or more primers or probes specific to one or more of CEA, CK7, CK19, CK20, VIL1, TACSTD1, and PVA and RNA extracted from the lymph node of a patient diagnosed with or suspected of having esophageal cancer, or a nucleic acid, or analog thereof, derived from the RNA.

In a further embodiment, the present invention relates to a composition comprising one or more primers or probes specific to one or more of CEA, CK19, PThRP, PVA, TACSTD1 and SCCA1.2 and RNA extracted from the lymph node of a patient diagnosed with or suspected of having squamous cell carcinoma of the head and neck, or a nucleic acid, or analog thereof, derived from the RNA.

In still a further embodiment, the present invention relates to a composition comprising one or more primers or probes specific to one or more of CDX1, TACSTD1 and VIL1 and RNA extracted from the lymph node of a patient diagnosed with or suspected of having colon cancer, or a nucleic acid, or an analog thereof, derived from the RNA.

In yet a further embodiment, the present invention relates to a composition comprising one or more primers or probes specific to one or more of MAGEA136-plex, MART1 and TYR and RNA extracted from a lymph node of a patient diagnosed with or suspected of having melanoma, or a nucleic acid, or analog thereof, derived from the RNA.

In another embodiment, the present invention relates to a composition comprising one or more primers or probes specific to PVA and RNA extracted from a sentinel lymph node of a patient diagnosed with or suspected of having a squamous cell carcinoma, or a nucleic acid, or analog thereof, derived from the RNA.

BRIEF DESCRIPTION OF THE DRAWINGS

FIG. 1 is a listing of a cDNA sequence of the caudal-type homeo box transcription factor 1 (CDX1) marker (SEQ ID NO: 1).

FIG. 2 is a listing of a cDNA sequence for the carcinoembryonic antigen-related cell adhesion molecule 5 (CEA) marker (SEQ ID NO: 2).

FIG. 3 is a listing of a cDNA sequence for the cytokeratin 7 (CK7) marker (SEQ ID NO: 3).

FIG. 4 is a listing of a cDNA sequence for the cytokeratin 19 (CK19) marker (SEQ ID NO: 4).

FIG. 5 is a listing of a cDNA sequence for the cytokeratin 20 (CK20) marker (SEQ ID NO: 5).

FIG. 6 is a listing of a cDNA sequence for the melanoma antigen gene family A1 (MAGEA1) marker (SEQ ID NO: 6).

FIG. 7 is a listing of a cDNA sequence for the melanoma antigen gene family A3 (MAGEA3) marker (SEQ ID NO: 7).

FIG. 8 is a listing of a cDNA sequence for the melanoma antigen gene family A6 (MAGEA6) marker (SEQ ID NO: 8).

FIG. 9 is a listing of a cDNA sequence for the melanoma antigen recognized by T cells 1 (MART1) marker (SEQ ID NO: 9).

FIG. 10 is a listing of a cDNA sequence for the parathyroid hormone-related protein (PTHrP) marker (SEQ ID NO: 10).

FIG. 11 is a listing of a cDNA sequence for the pemphigu vulgatis antigen (PVA) marker (SEQ ID NO: 11).

FIG. 12 is a listing of a cDNA sequence for the squamous cell carcinoma antigen 1 (SCCA1) marker (SEQ ID NO: 12).

FIG. 13 is a listing of a cDNA sequence for the squamous cell carcinoma antigen 2 (SCCA2) marker (SEQ ID NO: 13).

FIG. 14 is a listing of a cDNA sequence for the tumor-associated calcium signal transducer 1 (TACSTD1) marker (SEQ ID NO: 14).

FIG. 15 is a listing of a cDNA sequence for the tyrosinase (TYR) marker (SEQ ID NO: 15).

FIG. 16 is a listing of a cDNA sequence for the villin 1 (VIL1) marker (SEQ ID NO: 16).

FIG. 20A-F provides scatter plots illustrating the ability of two-marker systems to distinguish between benign and malignant cells in a lymph node of a head & neck cancer patient (negative—circle; positive—"+").

DETAILED DESCRIPTION

Figure 17:
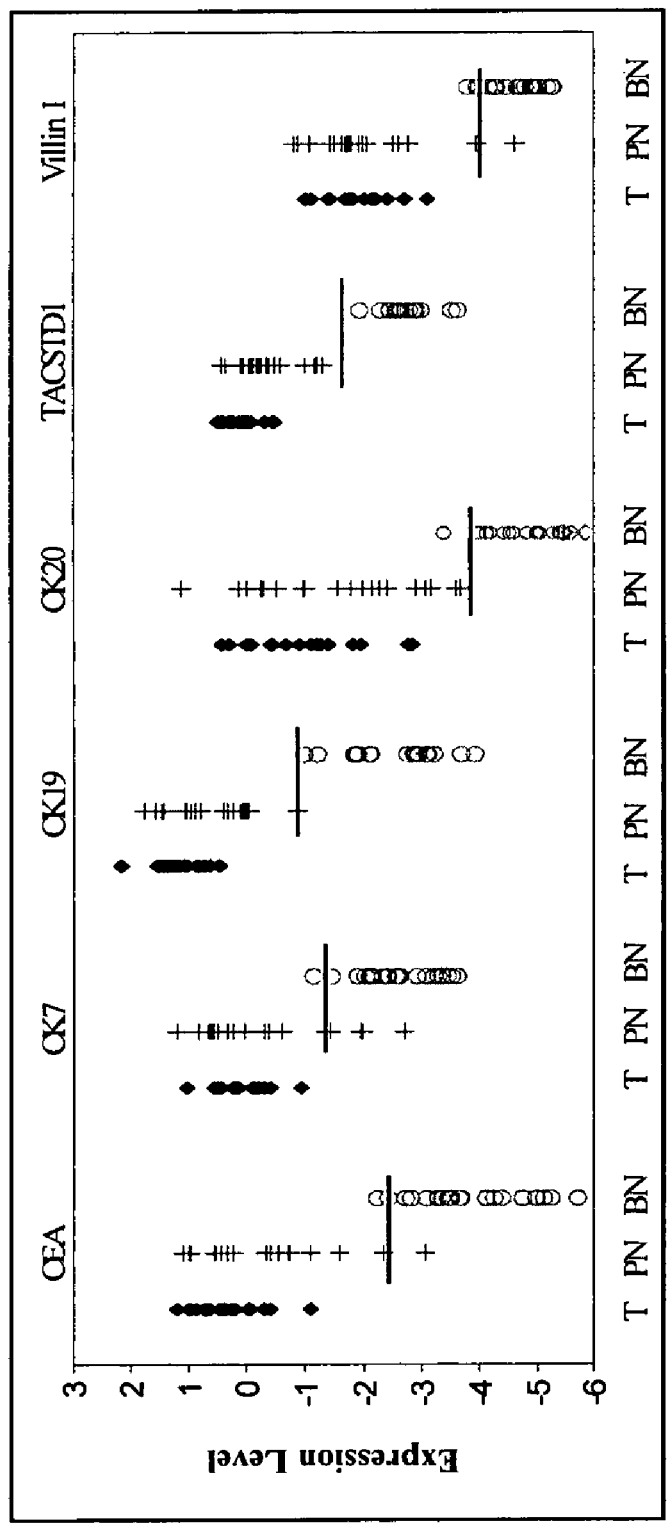
FIG. 17 is a scatter plot showing the expression levels of CEA, CK7, SCCA1.2, CK20, TACSTD1, VIL and CK19 in primary tumor, tumor-positive lymph nodes and benign lymph nodes of an esophageal cancer patient.

Provided are methods and compositions useful in identifying esophageal cancer, colon cancer, head and neck cancer and melanoma cells, including micrometastases, in lymph nodes. Early detection of metastases typically is related to patient survival. Very small metastases often go undetected in histological study of lymph node biopsies, resulting in false negative results that result in decreased chances of patient survival. The nucleic acid detection assays described herein are much more discriminating than are histological studies in most instances (a few, excellent histologists are capable of identifying micrometastases in lymph node sections), and are robust and repeatable in the hands of any minimally-trained technician. Although the methods and compositions described herein are necessarily presented comprising expression of specific mRNA markers, this should be understood that it shall not be deemed to exclude methods and compositions comprising combinations of the specific markers and other markers known in the art.

To this end, a number of molecular markers are identified, that are expressed in certain cancer types, including esophageal cancer, colon cancer, head and neck cancer and melanoma. These markers are markers specific to the tissue from which the particular cancer type arises and typically are not expressed, at least to the same levels, in lymphoid tissue. The presence and/or elevated expression of one or more of these markers in sentinel lymph node tissue is indicative of displaced cells in the lymphoid tissue, which correlates strongly with a cancer diagnosis. As used herein a "squamous cell carcinoma" is a cancer arising, at least in part, from a squamous cell population and/or containing, at least in part, a squamous cell population including, without limitation, cancers of the cervix; penis; head and neck, including, without limitation cancers of the oral cavity, salivary glands, paranasal sinuses and nasal cavity, pharynx and larynx; lung; esophageal; skin other than melanoma; vulva and bladder.

As used herein, the terms "expression" and "expressed" mean production of a gene-specific mRNA by a cell. In the context of the present disclosure, a "marker" is a gene that is expressed abnormally in a lymphatic biopsy. In one embodiment, the markers described herein are mRNA species that are expressed in cells of a specific tumor source at a significantly higher level as compared to expression in lymphoid cells.

Expression levels of mRNA can be quantified by a number of methods. Traditional methods include Northern blot analysis. More recently, nucleic acid detection methods have been devised that facilitate quantification of transcripts. Examples of PCR methods are described in U.S. patent application Ser. No. 10/090,326, incorporated herein by reference in its entirety. Other methods for determining expression levels of a given mRNA include isothermic amplification or detection assays and array technologies, as are known in the art, such as, without limitation, those described below.

The improved PCR methods described herein as well as in U.S. Ser. No. 10/090,326, and other nucleic acid detection and amplification methods described herein and as are known in the art permit rapid detection of cancer cells in lymph node tissue. These rapid methods can be used intraoperatively, and also are useful in detecting rare nucleic acid species, even in multiplexed PCR reactions that concurrently detect a more prevalent control nucleic acid.

A typical PCR reaction includes multiple amplification steps, or cycles that selectively amplify a target nucleic acid species. Because detection of transcripts is necessary, the PCR reaction is coupled with a reverse transcription step (reverse transcription PCR, or RT-PCR). A typical PCR reaction includes three steps: a denaturing step in which a target nucleic acid is denatured; an annealing step in which a set of PCR primers (forward and backward primers) anneal to complementary DNA strands; and an elongation step in which a thermostable DNA polymerase elongates the primers. By repeating this step multiple times, a DNA fragment is amplified to produce an amplicon, corresponding to the target DNA sequence. Typical PCR reactions include 30 or more cycles of denaturation, annealing and elongation. In many cases, the annealing and elongation steps can be performed concurrently, that is at the same temperature, in which case the cycle contains only two steps.

The lengths of the denaturation, annealing and elongation stages may be any desirable length of time. However, in attempting to shorten the PCR amplification reaction to a time suitable for intraoperative diagnosis, the lengths of these steps can be in the seconds range, rather than the minutes range. The denaturation step may be conducted for times of one second or less. The annealing and elongation steps optimally are less than 10 seconds each, and when conducted at the same temperature, the combination annealing/elongation step may be less than 10 seconds. Use of recently developed amplification techniques, such as conducting the PCR reaction in a Rayleigh-Bénard convection cell, also can dramatically shorten the PCR reaction time beyond these time limits (see, Krishnan, My et al., "PCR in a Rayleigh-Bénard convection cell." *Science* 298:793 (2002), and Braun, D. et al., "Exponential DNA Replication by Lominar Convection," *Physical Review Letters*, 91:158103).

As described in U.S. Ser. No. 10/090,326, each cycle may be shortened considerably without substantial deterioration of production of amplicons. Use of high concentrations of primers is helpful in shortening the PCR cycle time. High concentrations typically are greater than about 400 nM, and often greater than about 800 nM, though the optimal concentration of primers will vary somewhat from assay-to-assay. Sensitivity of RT-PCR assays may be enhanced by the use of a sensitive reverse transcriptase enzyme (described below) and/or high concentrations of reverse transcriptase primer to produce the initial target PCR template.

The specificity of any given PCR reaction relies heavily, but not exclusively, on the identity of the primer sets. The primer sets are pairs of forward and reverse oligonucleotide primers that anneal to a target DNA sequence to permit amplification of the target sequence, thereby producing a target sequence-specific amplicon. PCR primer sets can include two primers internal to the target sequence, or one primer internal to the target sequence and one specific to a target sequence that is ligated to the DNA or cDNA target, using a technique known as "ligation-anchored PCR" (Troutt, A. B., et al. (1992), "Ligation-anchored PCR: A Simple Amplification Technique with Single-sided Specificity," *Proc. Natl. Acad. Sci. USA*, 89:9823-9825).

As used herein, a "derivative" of a specified oligonucleotide is an oligonucleotide that binds to the same target sequence as the specified oligonucleotide and amplifies the same target sequence to produce essentially the same amplicon as the specified oligonucleotide but for differences between the specified oligonucleotide and its derivative. The derivative may differ from the specified oligonucleotide by insertion, deletion and/or substitution of any residue of the specified sequence so long as the derivative substantially retains the characteristics of the specified sequence in its use for the same purpose as the specified sequence.

As used herein, "reagents" for any assay or reaction, such as a reverse transcription and PCR, are any compound or composition that is added to the reaction mixture including, without limitation, enzyme(s), nucleotides or analogs thereof, primers and primer sets, probes, antibodies or other binding reagents, detectable labels or tags, buffers, salts and co-factors. As used herein, unless expressed otherwise, a "reaction mixture" for a given assay or reaction includes all necessary compounds and/or compositions necessary to perform that assay or reaction, even if those compounds or compositions are not expressly indicated. Reagents for many common assays or reactions, such as enzymatic reaction, are known in the art and typically are provided and/or suggested when the assay or reaction kit is sold.

As also described in U.S. Ser. No. 10/090,326, multiplexed PCR assays may be optimized, or balanced, by time-shifting the production of amplicons, rather than by manipulating primer concentrations. This may be achieved by using two primer sets, each primer set having a different Tm so that a two-stage PCR assay can be performed, with different annealing and/or elongation temperatures for each stage to favor the production of one amplicon over another. This time and temperature shifting method permits optimal balancing of the multiplex reaction without the difficulties faced when manipulation of primer concentrations is used to balance the reaction. This technique is especially useful in a multiplex reaction where it is desirable to amplify a rare cDNA along with a control cDNA.

A quantitative reverse transcriptase polymerase chain reaction (QRT-PCR) for rapidly and accurately detecting low abundance RNA species in a population of RNA molecules (for example, and without limitation, total RNA or mRNA), includes the steps of: a) incubating an RNA sample with a reverse transcriptase and a high concentration of a target sequence-specific reverse transcriptase primer under conditions suitable to generate cDNA; b) subsequently adding suitable polymerase chain reaction (PCR) reagents to the reverse transcriptase reaction, including a high concentration of a PCR primer set specific to the cDNA and a thermostable DNA polymerase to the reverse transcriptase reaction, and c) cycling the PCR reaction for a desired number of cycles and under suitable conditions to generate PCR product ("amplicons") specific to the cDNA. By temporally separating the reverse transcriptase and the PCR reactions, and by using reverse transcriptase-optimized and PCR-optimized primers, excellent specificity is obtained. The reaction may be conducted in a single tube (all tubes, containers, vials, cells and the like in which a reaction is performed may be referred to herein, from time to time, generically, as a "reaction vessel"), removing a source of contamination typically found in two-tube reactions. These reaction conditions permit very rapid QRT-PCR reactions, typically on the order of 20 minutes from the beginning of the reverse transcriptase reaction to the end of a 40 cycle PCR reaction.

The reaction c) may be performed in the same tube as the reverse transcriptase reaction by adding sufficient reagents to the reverse transcriptase (RT) reaction to create good, or even optimal conditions for the PCR reaction to proceed. A single tube may be loaded, prior to the running of the reverse transcriptase reaction, with: 1) the reverse transcriptase reaction mixture, and 2) the PCR reaction mixture to be mixed with the cDNA mixture after the reverse transcriptase reaction is completed. The reverse transcriptase reaction mixture and the PCR reaction mixture may be physically separated by a solid, or semi-solid (including amorphous, glassy substances and waxy) barrier of a composition that melts at a temperature greater than the incubation temperature of the reverse transcriptase reaction, but below the denaturing temperature of the PCR reaction. The barrier composition may be hydrophobic in nature and forms a second phase with the RT and PCR reaction mixtures when in liquid form. One example of such a barrier composition is wax beads, commonly used in PCR reactions, such as the AMPLIWAX PCR GEM products commercially available from Applied Biosystems of Foster City, Calif.

Alternatively, the separation of the reverse transcriptase and the PCR reactions may be achieved by adding the PCR reagents, including the PCR primer set and thermostable DNA polymerase, after the reverse transcriptase reaction is completed. Preferably the PCR reagents, are added mechanically by a robotic or fluidic means to make sample contamination less likely and to remove human error.

The products of the QRT-PCR process may be compared after a fixed number of PCR cycles to determine the relative quantity of the RNA species as compared to a given reporter gene. One method of comparing the relative quantities of the products of the QRT-PCR process is by gel electrophoresis, for instance, by running the samples on a gel and detecting those samples by one of a number of known methods including, without limitation, Southern blotting and subsequent detection with a labeled probe, staining with ethidium bromide and incorporating fluorescent or radioactive tags in the amplicons.

However, the progress of the quantitative PCR reactions typically is monitored by determining the relative rates of amplicon production for each PCR primer set. Monitoring amplicon production may be achieved by a number of processes, including without limitation, fluorescent primers, fluorogenic probes and fluorescent dyes that bind double-stranded DNA. A common method is the fluorescent 5' nuclease assay. This method exploits the 5' nuclease activity of certain thermostable DNA polymerases (such as Taq or Tfl DNA polymerases) to cleave an oligomeric probe during the PCR process. The oligomer is selected to anneal to the amplified target sequence under elongation conditions. The probe typically has a fluorescent reporter on its 5' end and a fluorescent quencher of the reporter at the 3' end. So long as the oligomer is intact, the fluorescent signal from the reporter is quenched. However, when the oligomer is digested during the elongation process, the fluorescent reporter no longer is in proximity to the quencher. The relative accumulation of free fluorescent reporter for a given amplicon may be compared to the accumulation of the same amplicons for a control sample and/or to that of a control gene, such as $\beta$-actin or 18S rRNA to determine the relative abundance of a given cDNA product of a given RNA in a RNA population. Products and reagents for the fluorescent 5' nuclease assay are readily available commercially, for instance from Applied Biosystems.

Equipment and software also are readily available for monitoring amplicon accumulation in PCR and QRT-PCR according to the fluorescent 5' nuclease assay and other QPCR/QRT-PCR procedures, including the Smart Cycler, commercially available from Cepheid of Sunnyvale, Calif., the ABI Prism 7700 Sequence Detection System (TaqMan), commercially available from Applied Biosystems. A cartridge-based sample preparation system (GenXpert) combines a thermal cycler and fluorescent detection device having the capabilities of the Smart Cycler product with fluid circuits and processing elements capable of automatically extracting specific nucleic acids from a tissue sample and performing QPCR or QRT-PCR on the nucleic acid. The system uses disposable cartridges that can be configured and pre-loaded with a broad variety of reagents. Such a system can be configured to disrupt tissue and extract total RNA or mRNA from the sample. The reverse transcriptase reaction components can be added automatically to the RNA and the QPCR reaction components can be added automatically upon completion of the reverse transcriptase reaction.

Further, the PCR reaction may be monitored of production (or loss) of a particular fluorochrome from the reaction. When the fluorochrome levels reach (or fall to) a desired level, the automated system will automatically alter the PCR conditions. In one example, this is particularly useful in the multiplexed embodiment described above, where a more-abundant (control) target species is amplified by the first, lower Tm, primer set at a lower temperature than the less abundant species amplified by the second, higher Tm, primer set. In the first stage of the PCR amplification, the annealing temperature is lower than the effective Tm of the first primer set. The annealing temperature then is automatically raised above the effective Tm of the first primer set when production of the first amplicon by the first primer set is detected. In a system that automatically dispenses multiple reagents from a cartridge, such as the GeneXpert system, a first PCR reaction may be conducted at the first Tm and, when the first PCR reaction proceeds past a threshold level, a second primer with a different Tm is added, resulting in a sequential multiplexed reaction.

In the above-described reactions, the amounts of certain reverse transcriptase and the PCR reaction components typically are atypical in order to take advantage of the faster ramp times of some thermal cyclers. Specifically, the primer concentrations are very high. Typical gene-specific primer concentrations for reverse transcriptase reactions are less than about 20 nM. To achieve a rapid reverse transcriptase reaction on the order of one to two minutes, the reverse transcriptase primer concentration was raised to greater than 20 nM, preferably at least about 50 nM, and typically about 100 nM. Standard PCR primer concentrations range from 100 nM to 300 nM. Higher concentrations may be used in standard PCR reactions to compensate for Tm variations. However, the referenced primer concentrations are for circumstances where no Tm compensation is needed. Proportionately higher concentrations of primers may be empirically determined and used if Tm compensation is necessary or desired. To achieve rapid PCR reactions, the PCR primer concentrations typically are greater than 200 nM, preferably greater than about 500 nM and typically about 800 nM. Typically, the ratio of reverse transcriptase primer to PCR primer is about 1 to 8 or more. The increase in primer concentrations permitted PCR experiments of 40 cycles to be conducted in less than 20 minutes.

A sensitive reverse transcriptase may be preferred in certain circumstances where either low amounts of RNA are present or a target RNA is a low abundance RNA. By the term "sensitive reverse transcriptase," it is meant a reverse transcriptase capable of producing suitable PCR templates from low copy number transcripts for use as PCR templates. The sensitivity of the sensitive reverse transcriptase may derive from the physical nature of the enzyme, or from specific reaction conditions of the reverse transcriptase reaction mixture that produces the enhanced sensitivity. One example of a sensitive reverse transcriptase is SensiScript RT reverse transcriptase, commercially available from Qiagen, Inc. of Valencia, Calif. This reverse transcriptase is optimized for the production of cDNA from RNA samples of <50 ng, but also has the ability to produce PCR templates from low copy number transcripts. In practice, in the assays described herein, adequate results were obtained for samples of up to, and even in excess of, about 400 ng RNA. Other sensitive reverse transcriptases having substantially similar ability to reverse transcribe low copy number transcripts would be equivalent sensitive reverse transcriptase for the purposes described herein. Notwithstanding the above, the ability of the sensitive reverse transcriptase to produce cDNA from low quantities of RNA is secondary to the ability of the enzyme, or enzyme reaction system to produce PCR templates from low copy number sequences.

As discussed above, the procedures described herein also may be used in multiplex QRT-PCR processes. In its broadest sense, a multiplex PCR process involves production of two or more amplicons in the same reaction vessel. Multiplex amplicons may be analyzed by gel electrophoresis and detection of the amplicons by one of a variety of methods, such as, without limitation ethidium bromide staining, Southern blotting and hybridization to probes, or by incorporating fluorescent or radioactive moieties into the amplicons and subsequently viewing the product on a gel. However, real-time monitoring of the production of two or more amplicons is preferred. The fluorescent 5' nuclease assay is the most common monitoring method. Equipment is now available (for example, the above-described Smart Cycler and TaqMan products) that permits the real-time monitoring of accumulation of two or more fluorescent reporters in the same tube. For multiplex monitoring of the fluorescent 5' nuclease assay, oligomers are provided corresponding to each amplicon species to be detected. The oligomer probe for each amplicon species has a fluorescent reporter with a different peak emission wavelength than the oligomer probe(s) for each other amplicons species. The accumulation of each unquenched fluorescent reporter can be monitored to determine the relative amounts of the target sequence corresponding to each amplicon.

In traditional multiplex QPCR and QRT-PCR procedures, the selection of PCR primer sets having similar annealing and elongation kinetics and similar sized amplicons are desirable. The design and selection of appropriate PCR primer sets is a process that is well known to a person skilled in the art. The process for identifying optimal PCR primer sets, and respective ratios thereof to achieve a balanced multiplex reaction also is known. By "balanced," it is meant that certain amplicon(s) do not out-compete the other amplicon(s) for resources, such as dNTPs or enzyme. For instance, by limiting the abundance of the PCR primers for the more abundant RNA species in an RT-PCR experiment will allow the detection of less abundant species. Equalization of the Tm (melting temperature) for all PCR primer sets also is encouraged. See, for instance, ABI PRISM 7700 Sequence Detection System User Bulletin #5, "Multiplex PCR with TaqMan VIC Probes", Applied Biosystems (1998/2001).

Despite the above, for very low copy number transcripts, it is difficult to design accurate multiplex PCR experiments, even by limiting the PCR primer sets for the more abundant control species. One solution to this problem is to run the PCR reaction for the low abundance RNA in a separate tube than the PCR reaction for the more abundant species. However, that strategy does not take advantage of the benefits of running a multiplex PCR experiment. A two-tube process has several drawbacks, including cost, the addition of more room for experimental error and the increased chance of sample contamination, which is critical in PCR assays.

A method has been described in WO 02/070751 for performing a multiplex PCR process, including QRT-PCR and QPCR, capable of detecting low copy number nucleic acid species along with one or more higher copy number species. The difference between low copy number and high copy number nucleic acid species is relative, but is referred to herein as a difference in the prevalence of a low (lower) copy number species and a high (higher) copy number species of at least about 30-fold, but more typically at least about 100-fold. For purposes herein, the relative prevalence of two nucleic acid species to be amplified is more salient than the relative prevalence of the two nucleic acid species in relation to other nucleic acid species in a given nucleic acid sample because other nucleic acid species in the nucleic acid sample do not directly compete with the species to be amplified for PCR resources.

As used herein, the prevalence of any given nucleic acid species in a given nucleic acid sample, prior to testing, is unknown. Thus, the "expected" number of copies of a given nucleic acid species in an nucleic acid sample often is used herein and is based on historical data on the prevalence of that species in nucleic acid samples. For any given pair of nucleic acid species, one would expect, based on previous determinations of the relative prevalence of the two species in a sample, the prevalence of each species to fall within a range. By determining these ranges one would determine the difference in the expected number of target sequences for each species. An mRNA species is identified as "overabundant" if it is present in statistically significant amounts over normal prevalence of the mRNA species in a sample from a normal patient or lymph node. As is abundantly illustrated in the examples and plots provided herein, a person of skill in the art would be able to ascertain statistically significant ranges or cutoffs for determining the precise definition of "overabundance" for any one or more mRNA species.

The multiplex method involves performing a two-(or more) stage PCR amplification, permitting modulation of the relative rate of production of a first amplicon by a first primer set and a second amplicon by a second primer set during the respective amplification stages. By this method, PCR amplifications to produce amplicons directed to a lower abundance nucleic acid species are effectively "balanced" with PCR amplifications to produce amplicons directed to a higher abundance nucleic acid species. Separating the reaction into two or more temporal stages may be achieved by omitting the PCR primer set for any amplicons that are not to be produced in the first amplification stage. This is best achieved through use of automated processes, such as the GenXpert prototype system described above. Two or more separate amplification stages may be used to tailor and balance multiplex assays, along with, or to the exclusion of tailoring the concentration of the respective primer sets.

A second method for temporally separating the PCR amplification process into two or more stages is to select PCR primer sets with variation in their respective Tm. In one example, primers for a lower copy number nucleic acid species would have a higher Tm ($Tm_1$) than primers for a higher abundance species ($Tm_2$). In this process, the first stage of PCR amplification is conducted for a predetermined number of cycles at a temperature sufficiently higher than $Tm_2$ so that there is substantially no amplification of the higher abundance species. After the first stage of amplification, the annealing and elongation steps of the PCR reaction are conducted at a lower temperature, typically about $Tm_2$, so that both the lower abundance and the higher abundance amplimers are amplified. It should be noted that Tm, as used herein and unless otherwise noted, refers to "effective Tm," which is the Tm for any given primer in a given reaction mix, which depends on factors, including, without limitation, the nucleic acid sequence of the primer and the primer concentration in the reaction mixture.

It should be noted that PCR amplification is a dynamic process. When using temperature to modulate the respective PCR reactions in a multiplex PCR reaction, the higher temperature annealing stage may be carried out at any temperature typically ranging from just above the lower Tm to just below the higher Tm, so long as the reaction favors production of the amplicon by the higher Tm primer set. Similarly, the annealing for the lower temperature reaction typically is at any temperature below the Tm of the low temperature primer set.

In the example provided above, in the higher temperature stage the amplicon for the low abundance RNA is amplified at a rate faster than that the amplicon for the higher abundance RNA (and preferably to the substantial exclusion of production of the second amplicon), so that, prior to the second amplification stage, where it is desirable that amplification of all amplicons proceeds in a substantially balanced manner, the amplicon for the lower abundance RNA is of sufficient abundance that the amplification of the higher abundance RNA does not interfere with the amplification of the amplicon for the lower abundance RNA. In the first stage of amplification, when the amplicon for the low abundance nucleic acid is preferentially amplified, the annealing and elongation steps may be performed above $Tm_1$ to gain specificity over efficiency (during the second stage of the amplification, since there is a relatively large number of low abundance nucleic acid amplicons, selectivity no longer is a significant issue, and efficiency of amplicon production is preferred). It, therefore, should be noted that although favorable in many instances, the temperature variations may not necessarily result in the complete shutdown of one amplification reaction over another.

In another variation of the above-described amplification reaction, a first primer set with a first Tm may target a more-abundant template sequence (for instance, the control template sequence) and a second primer set with a higher Tm may target a less-abundant template sequence. In this case, the more-abundant template and the less-abundant template may both be amplified in a first stage at a temperature below the (lower) Tm of the first primer set. When a threshold amount of amplicon corresponding to the more abundant template is reached, the annealing and/or elongation temperature of the reaction is raised above the Tm of the first primer set, but below the higher Tm of the second primer set to effectively shut down amplification of the more abundant template.

Selection of three or more sets of PCR primer sets having three or more different Tms (for instance, $Tm_1>Tm_2>Tm_3$) can be used to amplify sequences of varying abundance in a stepwise manner, so long as the differences in the Tms are sufficiently large to permit preferential amplification of desired sequences to the substantial exclusion of undesired sequences for a desired number of cycles. In that process, the lowest abundance sequences are amplified in a first stage for a predetermined number of cycles. Next, the lowest abundance and the lesser abundance sequences are amplified in a second stage for a predetermined number of cycles. Lastly, all sequences are amplified in a third stage. As with the two-stage reaction described above, the minimum temperature for each stage may vary, depending on the relative efficiencies of each single amplification reaction of the multiplex reaction. It should be recognized that two or more amplimers may have substantially the same Tm, to permit amplification of more than one species of similar abundance at any stage of the amplification process. As with the two-stage reaction, the three-stage reaction may also proceed stepwise from amplification of the most abundant nucleic acid species at the lowest annealing temperature to amplification of the least abundant species at the highest annealing temperature.

By this sequential amplification method, an additional tool is provided for the "balancing" of multiplex PCR reactions besides the matching of Tms and using limiting amounts of one or more PCR primer sets. The exploitation of PCR primer sets with different Tms as a method for sequentially amplifying different amplicons may be preferred in certain circumstances to the sequential addition of additional primer sets. However, the use of temperature-dependent sequencing of multiplex PCR reactions may be coupled with the sequential physical addition of primer sets to a single reaction mixture.

An internal positive control that confirms the operation of a particular amplification reaction for a negative result also may be used. The internal positive controls (IPC) are DNA oligonucleotides that have the same primer sequences as the target gene (CEA or tyrosinase) but have a different internal probe sequence. Selected sites in the IPC's optionally may be synthesized with uracil instead of thymine so that contamination with the highly concentrated mimic could be controlled using uracil DNA glycosylase, if required. The IPCs maybe added to any PCR reaction mastermix in amounts that are determined empirically to give Ct values typically greater than the Ct values of the endogenous target of the primer set. The PCR assays are then performed according to standard protocols, and even when there is no endogenous target for the primer set, the IPC would be amplified, thereby verifying that the failure to amplify the target endogenous DNA is not a failure of the PCR reagents in the mastermix. In this embodiment, the IPC probe fluoresces differently than the probe for the endogenous sequences. A variation of this for use in RT-PCR reactions is where the IPC is an RNA and the RNA includes an RT primer sequence. In this embodiment, the IPC verifies function of both the RT and PCR reactions. Both RNA and DNA IPCs (with different corresponding probes) may also be employed to differentiate difficulties in the RT and PCR reactions.

The rapid QRT-PCR protocols described herein may be run in about 20 minutes. This short time period permits the assay to be run intraoperatively so that a surgeon can decide on a surgical course during a single operation (typically the patient will remain anesthetized and/or otherwise sedated in a single "operation", though there may be a waiting period between when the sample to be tested is obtained and the time the interoperative assay is complete), rather than requiring a second operation, or requiring the surgeon to perform unneeded or overly broad prophylactic procedures. For instance, in the surgical evaluation of certain cancers, including breast cancer, melanoma, lung cancer, esophageal cancer and colon cancer, tumors and sentinel lymph nodes are removed in a first operation. The sentinel nodes are later evaluated for micrometastases, and, when micrometastases are detected in a patient's sentinel lymph node, the patient will need a second operation, thereby increasing the patient's surgical risks and patient discomfort associated with multiple operations. With the ability to determine the expression levels of certain tumor-specific markers described herein in less than 30 minutes with increased accuracy, a physician can make an immediate decision on how to proceed without requiring the patient to leave the operating room or associated facilities. The rapid test also is applicable to needle biopsies taken in a physician's office. A patient need not wait for days to get the results of a biopsy (such as a needle biopsy of a tumor or lymph node), but can now get more accurate results in a very short time.

As used herein, in the context of gene expression analysis, a probe is "specific to" a gene or transcript if under reaction conditions it can hybrizide specifically to transcripts of that gene within a sample, or sequences complementary thereto, and not to other transcripts. Thus, in a diagnostic assay, a probe is specific to a gene if it can bind to a specific transcript or desired family of transcripts in mRNA extracted from a specimen, to the practical exclusion (does not interfere substantially with the detection assay) of other transcripts. In a PCR assay, primers are specific to a gene if they specifically amplify a sequence of that gene, to the practical exclusion of other sequences in a sample.

Table B provides primer and probe sequences for the mRNA quantification assays described and depicted in the Examples and Figures. FIGS. 1-16 provide non-limiting examples of cDNA sequences of the various mRNA species detected in the Examples. Although the sequences provided in Table B were found effective in the assays described in the examples, other primers and probes would likely be equally suited for use in the QRT-PCR and other mRNA detection and quantification assays, either described herein or as are known in the art. Design of alternate primer and probe sets for PCR assays, as well as for other mRNA detection assays is well within the abilities of one of average skill in the art. For example and without limitation, a number of computer software programs will generate primers and primer sets for PCR assays from cDNA sequences according to specified parameters. Non limiting examples of such software include, NetPrimer and Primer Premier 5, commercially available from PREMIER Biosoft International of Palo Alto, Calif., which also provides primer and probe design software for molecular beacon and array assays. Primers and/or probes for two or more different mRNAs can be identified, for example and without limitation, by aligning the two or more target sequences according to standard methods, determining common sequences between the two or more mRNAs and entering the common sequences into a suitable primer design computer program.

As used herein, a "primer or probe" for detecting a specific mRNA species is any primer, primer set and/or probe that can be utilized to detect and/or quantify the specific mRNA species. An "mRNA species" can be a single mRNA species, corresponding to a single mRNA expression product of a single gene, or can be multiple mRNAs that are detected by a single common primer and/or probe combination, such as the SCCA1.2 and MAGEA136-plex pecies described below.

In the commercialization of the methods described herein, certain kits for detection of specific nucleic acids will be particularly useful. A kit typically comprises one or more reagents, such as, without limitation, nucleic acid primers or probes, packaged in a container, such as, without limitation, a vial, tube or bottle, in a package suitable for commercial distribution, such as, without limitation, a box, a sealed pouch, a blister pack and a carton. The package typically contains an indicia, for example and without limitation, a writing, illustration, label, book, booklet, tag and/or packaging insert, indicating that the packaged reagents can be used in a method for identifying expression of markers indicative of the presence of cancer cells in a lymph node of a patient. As used herein, "packaging materials" includes any article used in the packaging, for distribution of reagents in a kit, including, without limitation, containers, vials, tubes, bottles, pouches, blister packaging, labels, tags, instruction sheets, and package inserts.

One example of such a kit would include reagents necessary for the one-tube QRT-PCR process described above. In one example, the kit would include the above-described reagents, including reverse transcriptase, a reverse transcriptase primer, a corresponding PCR primer set, a thermostable DNA polymerase, such as Taq polymerase, and a suitable fluorescent reporter, such as, without limitation, a probe for a fluorescent 5' nuclease assay, a molecular beacon probe, a single dye primer or a fluorescent dye specific to double-stranded DNA, such as ethidium bromide. The primers may be present in quantities that would yield the high concentrations described above. Thermostable DNA polymerases are commonly and commercially available from a variety of manufacturers. Additional materials in the kit may include: suitable reaction tubes or vials, a barrier composition, typically a wax bead, optionally including magnesium; reaction mixtures (typically 10×) for the reverse transcriptase and the PCR stages, including necessary buffers and reagents such as dNTPs; nuclease- or RNase-free water; RNase inhibitor; control nucleic acid(s) and/or any additional buffers, compounds, co-factors, ionic constituents, proteins and enzymes, polymers, and the like that may be used in reverse transcriptase and/or PCR stages of QRT-PCR reactions.

Components of a kit are packaged in any manner that is commercially practicable. For example, PCR primers and reverse transcriptase may be packaged individually to facilitate flexibility in configuring the assay, or together to increase ease of use and to reduce contamination. Similarly, buffers, salts and co-factors can be packaged separately or together.

The kits also may include reagents and mechanical components suitable for the manual or automated extraction of nucleic acid from a tissue sample. These reagents are known to those skilled in the art and typically are a matter of design choice. For instance, in one embodiment of an automated process, tissue is disrupted ultrasonically in a suitable lysis solution provided in the kit. The resultant lysate solution is then filtered and RNA is bound to RNA-binding magnetic beads also provided in the kit or cartridge. The bead-bound RNA is washed, and the RNA is eluted from the beads and placed into a suitable reverse transcriptase reaction mixture prior to the reverse transcriptase reaction. In automated processes, the choice of reagents and their mode of packaging (for instance in disposable single-use cartridges) typically are dictated by the physical configuration of the robotics and fluidics of the specific RNA extraction system, for example and without limitation, the GenXpert system. International Patent Publication Nos. WO 04/48931, WO 03/77055, WO 03/72253, WO 03/55973, WO 02/52030, WO 02/18902, WO 01/84463, WO 01/57253, WO 01/45845, WO 00/73413, WO 00/73412 and WO 00/72970 provide non-limiting examples of cartridge-based systems and related technology useful in the methods described herein.

The constituents of the kits may be packaged together or separately, and each constituent may be presented in one or more tubes or vials, or in cartridge form, as is appropriate. The constituents, independently or together, may be packaged in any useful state, including without limitation, in a dehydrated, a lyophilized, a glassified or an aqueous state. The kits may take the physical form of a cartridge for use in automated processes, having two or more compartments including the above-described reagents. Suitable cartridges are disclosed for example in U.S. Pat. Nos. 6,440,725, 6,431,476, 6,403,037 and 6,374,684.

Array technologies also can facilitate determining the expression level of two or more genes by facilitating performance of the desired reactions and their analysis by running multiple parallel reactions at the same time. One example of an array is the GeneChip® gene expression array, commercially available from Affymetrix, Inc. of Santa Clara, Calif. Patents illustrating array technology and uses therefor include, without limitation, U.S. Pat. Nos. 6,040,138, 6,245,517, 6,251,601, 6,261,776, 6,306,643, 6,309,823, 6,346,413, 6,406,844 and 6,416,952. A plethora of other "array" patents exist, illustrating the multitude of physical forms a useful array can take. An "array", such as a "microarray" can be a substrate containing one or more binding reagents, typically in discrete physical locations, permitting high throughput analysis of the binding of a sample to the array. In the context of the methods described herein, an array contains probes specific to transcripts of one or more of the genes described herein affixed to a substrate. The probes can be nucleic acids or analogs thereof, as are known in the art. An array also can refer to a plurality of discrete reaction chambers, permitting multiple parallel reactions and detection events on a miniaturized scale.

As mentioned above, PCR-based technologies may be used to quantify mRNA levels in a given tissue sample. Other sequence-specific nucleic acid quantification methods may be more or less suited. In one embodiment, the nucleic acid quantification method is a rolling circle amplification method. Non-limiting examples of rolling circle amplification methods are described in U.S. Pat. Nos. 5,854,003; 6,183,960; 6,344,329; and 6,210,884, each of which are incorporated herein by reference to the extent they teach methods for detecting and quantifying RNA species. In one embodiment, a padlock probe is employed to facilitate the rolling circle amplification process. (See Nilsson, M. et al. (2002), "Making Ends Meet in Genetic Analysis Using Padlock Probes," *Human Mutation* 19:410-415 and Schweitzer, B. et al (2001), "Combining Nucleic Acid Amplification and Detection," *Current Opinion in Biotechnology*, 12:21-27). A padlock probe is a linear oligonucleotide or polynucleotide designed to include one target-complementary sequence at each end, and which is designed such that the two ends are brought immediately next to each other upon hybridization to the target sequence. The probe also includes a spacer between the target-complementary sequences that includes a polymerase primer site and a site for binding to a probe, such as a molecular beacon probe, for detecting the padlock probe spacer sequence. If properly hybridized to an RNA template, the probe ends can then be joined by enzymatic DNA ligation to form a circular template that can be amplified by polymerase extension of a complementary primer. Thousands of concatemerized copies of the template can be generated by each primer, permitting detection and quantification of the original RNA template. Quantification can be automated by use, for example and without limitation, of a molecular beacon probe or other probe capable of detecting accumulation of a target sequence. By using padlock probes with different spacers to bind different molecular beacons that fluoresce a different color on binding to the amplified spacer, this automated reaction can be multiplexed. Padlock probe sequences target unique portions of the target RNA in order to ensure specific binding with limited or no cross-reactivity. RCA is an isothermic method in that the amplification is performed at one temperature.

Another isothermic method, for example and without limitation, is nucleic acid sequence-based amplification (NASBA). A typical NASBA reaction is initiated by the annealing of a first oligonucleotide primer to an RNA target in an RNA sample. The 3' end of the first primer is complementary to the target analyte; the 5' end encodes the T7 RNA polymerase promoter. After annealing, the primer is extended by reverse transcription (AMV-RT, for example) to produce a cDNA. The RNA is digested with RNase H, permitting a second primer (sense) to anneal to the cDNA strand, permitting the DNA polymerase activity of the reverse transcriptase to be engaged, producing a double-stranded cDNA copy of the original RNA template, with a functional T7 RNA polymerase promoter at one end. T7 polymerase is then used to produce an additional RNA template, which is further amplified, though in reverse order, according to the same procedure. A variety of other nucleic acid detection and/or amplification methods are known to those of skill in the art, including variations on the isothermic strand displacement, PCR and RCA methods described herein.

Example 1

General Materials and Methods

Identification of Potential Markers. An extensive literature and public database survey was conducted to identify any potential markers. Resources for this survey included PubMed, OMIM, UniGene, GeneCards, and CGAP. Survey criteria were somewhat flexible but the goal was to identify genes with moderate to high expression in tumors and low expression in normal lymph nodes. In addition, genes reported to be upregulated in tumors and genes with restricted tissue distribution were considered potentially useful. Finally, genes reported to be cancer-specific, such as the cancer testis antigens and hTERT, were evaluated.

Tissues and Pathological Evaluation. Tissue specimens were obtained from tissue banks at the University of Pittsburgh Medical Center through IRB approved protocols. All specimens were snap frozen in liquid nitrogen and later embedded in OCT for frozen sectioning. Twenty 5-micron sections were cut from each tissue for RNA isolation. In addition, sections were cut and placed on slides for H&E and IHC analysis at the beginning, middle (between the tenth and eleventh sections for RNA), and end of the sections for RNA isolation. All three H&E slides from each specimen underwent pathological review to confirm presence of tumor, percentage of tumor, and to identify the presence of any contaminating tissues. All of the unstained slides were stored at −20° C. Immunohistochemistry evaluation was performed using the AE1/AE3 antibody cocktail (DAKO, Carpinteria, Calif.), and Vector Elite ABC kit and Vector AEC Chromagen (Vecta Laboratories, Burlingame, Calif.). IHC was used as needed as needed to confirm the H&E histology.

Screening Approach. The screening was conducted in two phases. All potential markers entered the primary screening phase and expression was analyzed in 6 primary tumors and 10 benign lymph nodes obtained from patients without cancer (5 RNA pools with 2 lymph node RNA's per pool). Markers that showed good characteristics for lymph node metastasis detection passed into the secondary screening phase. The secondary screen consisted of expression analysis on 20-25 primary tumors, 20-25 histologically positive lymph nodes and 21 benign lymph nodes without cancer.

RNA Isolation and cDNA Synthesis. RNA was isolated using the RNeasy minikit (Qiagen, Valencia, Calif.) essentially as described by the manufacturer. The only modification was that we doubled the volume of lysis reagent and loaded the column in two steps. This was found to provide better RNA yield and purity, probably as a result of diluting out the OCT in the tissue sections. Reverse transcription was performed in 100-µl reaction volumes either with random hexamer priming or sequence-specific priming using a probe indicated in Table C and Superscript II (Invitrogen, Carlsbad, Calif.) reverse transcriptase. For the primary screen, three reverse transcription reactions were performed, each with 500 ng of RNA. The cDNA's were combined and QPCR was performed using the equivalent of 20 ng RNA per reaction. For the secondary screen, the RNA input for primary tumors and positive nodes was also 500 ng. For benign nodes however, the RNA input was 2000 ng resulting in the equivalent of 80 ng RNA per QPCR reaction.

Quantitative PCR. All quantitative PCR was performed on the ABI Prism 7700 Sequence Detection Instrument (Applied Biosystems, Foster City, Calif.). Relative expression of the marker genes was calculated using the delta-CT methods previously described and with β-glucuronidase as the endogenous control gene. All assays were designed for use with 5' nuclease hybridization probes although the primary screening was performed using SYBR Green quantification in order to save cost. Assays were designed using the ABI Primer Express Version 2.0 software and where possible, amplicons spanned exon junctions in order to provide cDNA specificity. All primer pairs were tested for amplification specificity (generation of a single band on gels) at 60, 62 and 64° C. annealing temperature. In addition, PCR efficiency was estimated using SYBR green quantification prior to use in the primary screen. Further optimization and more precise estimates of efficiency were performed with 5' nuclease probes for all assays used in the secondary screen.

A mixture of the Universal Human Reference RNA (Stratagene, La Jolla, Calif.) and RNAs from human placenta, thyroid, heart, colon, PCI13 cell line and SKBR3 cell line served as a universal positive expression control for all the genes in the marker screening process.

Quantification with SYBR Green (Primary Screen). For SYBR Green I-based QPCR, each 50µl reaction contained 1×TaqMan buffer A (Applied Biosystems), 300 nM each dNTP, 3.5 mM $MgCl_2$, 0.06 units/µl Amplitaq Gold (Applied Biosystems), 0.25×SYBR Green I (Molecular Probes, Eugene, Oreg.) and 200 nM each primer. The amplification program comprised 2-stages with an initial 95° C. Taq activation stage for 12 mm followed by 40 cycles of 95° C. denaturation for 15 s, 60 or 62 or 64° C. anneal/extend for 60 s and a 10 second data collection step at a temperature 2-4° C. below the $T_m$ of the specific PCR product being amplified (Tom B. Morrison, et al, 1998). After amplification, a melting curve analysis was performed by collecting fluorescence data while increasing the temperature from 60° C.-95° C. over 20 minutes.

Quantification with 5' Nuclease Probes (Secondary Screen). Probe-based QPCR was performed as described previously (Godfrey et al., *Clinical Cancer Res.* 2001 Dec., 7(12):4041-8). Briefly, reactions were performed with a probe concentration of 200 nM and a 60 second anneal/extend phase at 60° C., or 62° C., or 64° C. The sequences of primers and probes (purchased from IDT, Coralville, Iowa) for genes evaluated in the secondary screen are listed in Table B, below.

Data Analysis. In the primary screen, data from the melt curve was analyzed using the ABI Prism 7700 Dissociation Curve Analysis 1.0 software (Applied Biosystems). The first derivative of the melting cure was used to determine the product $T_m$ as well as to establish the presence of the specific product in each sample. In general, samples were analyzed in duplicate PCR reactions and the average $C_t$ value was used in the expression analysis. However, in the secondary screen triplicate reactions were performed for each individual benign node and the lowest $C_t$ value was used in the calculation of relative expression in order to obtain the highest value of background expression for the sample.

Cancer tissue-specific studies have been conducted, as described in the Examples below, in which a variety of molecular markers were identified as correlating with pathological states in cancers including esophageal cancer, colon cancer, head and neck cancer and in melanoma. Table A identifies genes used in the following studies. Table B provides PCR primer and TAQMAN probe sequences used in the quantitative PCR and RT-PCR amplifications described herein. Table C provides RT primer sequences as used instead of random hexamer primers. All PCR and RT-PCR reactions were conducted using standard methods. For all figures, T=primary tumor; PN=tumor-positive lymph nodes (by histological screening, that is, by review of H&E stained tissue and, when needed, by IHC, as described above); and BN=benign lymph nodes (by histological screening)

TABLE A

| Marker | Accession No./ OMIN No.* | Official Gene Symbol | Official Gene Name | Alternative Gene Symbol | Alias |
| --- | --- | --- | --- | --- | --- |
| CDX1 | NM_001804/ 600746 | CDX1 | caudal type homeo box transcription factor 1 | NA | NA |
| CEA | NM_004363/ 114890 | CEACAM5 | carcinoembryonic antigen-related cell adhesion molecule 5 | CEA, CD66e | NA |

TABLE A-continued

| Marker | Accession No./ OMIN No.* | Official Gene Symbol | Official Gene Name | Alternative Gene Symbol | Alias |
|---|---|---|---|---|---|
| CK19 | NM_002276/ 148020 | KRT19 | keratin 19 | K19, CK19, K1CS, MGC15366 | cytokeratin 19; keratin, type I, 40-kd; keratin, type I cytoskeletal 19; 40-kDa keratin intermediate filament precursor gene |
| CK20 | NM_019010/ 608218 | KRT20 | keratin 20 | K20, CK20, MGC35423 | cytokeratin 20; keratin, type I; cytoskeletal 20 |
| TACSTD1 | NM_002354/ 185535 | TACSTD1 | tumor-associated calcium signal transducer 1 | EGP, KSA, M4S1, MK-1, KS1/4, EGP40, MIC18, TROP1, Ep-CAM, CO17-1A, GA733-2 | MK-1 antigen; antigen identified by monoclonal antibody AUA1; membrane component, chromosome 4, surface marker (35 kD glycoprotein) |
| VIL1 | NM_007127/ 193040 | VIL1 | villin 1 | VIL, D2S1471 | villin-1 |
| CK7 | NM_005556/ 148059 | KRT7 | keratin 7 | K7, CK7, SCL, K2C7, MGC3625 | Sarcolectin; cytokeratin 7; type II mesothelial keratin K7; keratin, type II cytoskeletal 7; keratin, 55 K type II cytoskeletal; keratin, simple epithelial type I, K7 |
| SCCA1 | NM_006919/ 600517 | SERPINB3 | serine (or cysteine) proteinase inhibitor, clade B (ovalbumin), member 3carcinoma antigen 1 & 2 | SCC, T4-A, SCCA1, SCCA-PD | squamous cell carcinoma antigen 1 |
| SCCA2 | NM_002974/ 600518 | SERPINB4 | serine (or cysteine) proteinase inhibitor, clade B (ovalbumin), member 4 | PI11, SCCA2, LEUPIN | leupin; squamous cell carcinoma antigen 2; protease inhibitor (leucine-serpin) |
| PTHrP | NM_002820/ 168470 | PTHLH | parathyroid hormone-like hormone | PTHRP, PTHR, HHM, | parathyroid hormone-related protein; pth-related protein; formerly humoral hypercalcemia of malignancy, included; |
| PVA | NM_001944/ 169615 | DSG3 | desmoglein 3 (pemphigus vulgaris antigen) | PVA, CDHF6 | pemphigus vulgaris antigen; 130-kD pemphigus vulgaris antigen |
| MAGEA1 | NM_004988/ 300016 | MAGEA1 | melanoma antigen, family A, 1 (directs expression of antigen MZ2-E) | MAGE1, MGC9326 | melanoma antigen MAGE-1; melanoma-associated antigen 1; melanoma-associated antigen MZ2-E |
| MAGEA3 | NM_005362/ 300174 | MAGEA3 | melanoma antigen, family A, 3 | HIP8, HYPD, MAGE3, MGC14613 | antigen MZ2-D; MAGE-3 antigen; melanoma-associated antigen 3 |
| MAGEA6 | NM_005363/ 300176 | MAGEA6 | melanoma antigen, family A, 6 | MAGE6, MAGE3B, MAGE-3b, MGC52297 | MAGE-6 antigen; melanoma-associated antigen 6 |
| MART1 | NM_005511/ 605513 | MLANA | melan-A | MART1, MART-1 | melanoma antigen recognized by t cells 1 |
| TYR | NM_000372/ 606933 | TYR | tyrosinase (oculocutaneous albinism IA) | OCA1A, OCAIA | Tyrosinase |

*Online Mendelian Inheritance in Man.

TABLE B

| Gene | Oligonucleotide | Sequence (5'→3') | Sequence Listing Reference |
|---|---|---|---|
| CDX1 | Forward primer | CGGTGGCAGCGGTAAGAC | SEQ ID NO: 1, bases 516 to 533 |
|  | Reverse primer | GATTGTGATGTAACGGCTGTAATG | SEQ ID NO: 17 |
|  | Probe | ACCAAGGACAAGTACCGCGTGGTCTACA | SEQ ID NO: 1, bases 538 to 565 |

TABLE B-continued

| Gene | Oligonucleotide | Sequence (5'→3') | Sequence Listing Reference |
|---|---|---|---|
| CEA | Forward primer | AGACAATCACAGTCTCTGCGGA | SEQ ID NO: 2, bases 1589 to 1610 |
| | Reverse primer | ATCCTTGTCCTCCACGGGTT | SEQ ID NO: 18 |
| | Probe | CAAGCCCTCCATCTCCAGCAACAACT | SEQ ID NO: 2, bases 1617 to 1642 |
| CK19 | Forward primer | AGATCGACAACGCCCGT | SEQ ID NO: 19 |
| | Reverse primer | AGAGCCTGTTCCGTCTCAAA | SEQ ID NO: 20 |
| | Probe | TGGCTGCAGATGACTTCCGAACCA | SEQ ID NO: 4, bases 614 to 637 |
| CK20 | Forward primer | CACCTCCCAGAGCCTTGAGAT | SEQ ID NO: 5, bases 915 to 935 |
| | Reverse primer | GGGCCTTGGTCTCCTCTAGAG | SEQ ID NO: 21 |
| | Probe | CCATCTCAGCATGAAAGAGTCTTTGGAGCA | SEQ ID NO: 5, bases 948 to 977 |
| CK7 | Forward primer | CCCTCAATGAGACGGAGTTGA | SEQ ID NO: 3, bases 807 to 827 |
| | Reverse primer | CCAGGGAGCGACTGTTGTC | SEQ ID NO: 22 |
| | Probe | AGCTGCAGTCCCAGATCTCCGACACATC | SEQ ID NO: 3, bases 831 to 858 |
| MAGEA136_plex[A] | Forward primer | GTGAGGAGGCAAGGTTYTSAG | SEQ ID NO: 23 |
| | Reverse primer | AGACCCACWGGCAGATCTTCTC | SEQ ID NO: 24 |
| | Probe1 | AGGATTCCCTGGAGGCCACAGAGG | SEQ ID NO: 6, bases 80 to 103 |
| | Probe2 | ACAGGCTGACCTGGAGGACCAGAGG | SEQ ID NO: 7, bases 90 to 104 |
| MART1 | Forward primer | GATGCTCACTTCATCTATGGTTACC | SEQ ID NO: 9, bases 66 to 90 |
| | Reverse primer | ACTGTCAGGATGCCGATCC | SEQ ID NO: 25 |
| | Probe | AGCGGCCTCTTCAGCGGTGGTGT | SEQ ID NO: 26 |
| PTHrP | Forward primer | GCGGTGTTCCTGCTGAGCTA | SEQ ID NO: 10, bases 356 to 375 |
| | Reverse primer | TCATGGAGGAGCTGATGTTCAGA | SEQ ID NO: 27 |
| | Probe | TCTCAGCCGCCGCCTCAAAAGA | SEQ ID NO: 10, bases 409 to 430 |
| PVA | Forward primer | AAAGAAACCCAATTGCCAAGATTAC | SEQ ID NO: 11, bases 280 to 304 |
| | Reverse primer | CAAAAGGCGGCTGATCGAT | SEQ ID NO: 28 |
| | Probe | CCAAGCAACCCAGAAAATCACCTACCG | SEQ ID NO: 11, bases 314 to 340 |
| SCCA1.2[B] | Forward primer | AAGCTGCAACATATCATGTTGATAGG | SEQ ID NO: 12, bases 267 to 292 |
| | Reverse primer | GGCGATCTTCAGCTCATATGC | SEQ ID NO: 29 |
| | Probe | TGTTCATCACCAGTTTCAAAAGCTTCTGACT | SEQ ID NO: 12, bases 301 to 331 |
| TACSTD1 | Forward primer | TCATTTGCTCAAAGCTGGCTG | SEQ ID NO: 14, bases 348 to 368 |
| | Reverse primer | GGTTTTGCTCTTCTCCCAAGTTT | SEQ ID NO: 30 |
| | Probe | AAATGTTTGGTGATGAAGGCAGAAATGAATGG | SEQ ID NO: 14, bases 371 to 402 |
| TYR | Forward primer | ACTTACTCAGCCCAGCATCATTC | SEQ ID NO: 15, bases 1284 to 1306 |
| | Reverse primer | ACTGATGGCTGTTGTACTCCTCC | SEQ ID NO: 31 |
| | Probe | TCTCCTCTTGGCAGATTGTCTGTAGCCGA | SEQ ID NO: 15, bases 1308 to 1336 |
| Villin1 | Forward primer | TGGTTCCTGGCTTGGGATC | SEQ ID NO: 16, bases 2152 to 2170 |
| | Reverse primer | TTGCCAGACTCCGCCTTC | SEQ ID NO: 32 |
| | Probe | TCAAGTGGAGTAACACCCAAATCCTATGAGGACC | SEQ ID NO: 16, bases 2174 to 2206 |

[A]A universal primer set designed to recognize transcripts of MAGEA1, MAGEA3 and MAGEA6.
[B]A universal primer set designed to recognize transcripts of both SCCA1 AND SCCA2.

TABLE C

| Gene Marker | RT Specific Primer (5'→3') | Sequence Listing Reference |
|---|---|---|
| CEA | GTGAAGGCCACAGCAT | SEQ ID NO: 33 |
| CK20 | AACTGGCTGCTGTAACG | SEQ ID NO: 34 |
| MART1 | GCCGATGAGCAGTAAGACT | SEQ ID NO: 35 |
| PVA | TGTCAACAACAAAGATTCCA | SEQ ID NO: 36 |
| SCCA1.2 | TCTCCGAAGAGCTTGTTG | SEQ ID NO: 37 |
| TACSTD1 | AGCCCATCATTGTTCTG | SEQ ID NO: 38 |
| TYR | CGTTCCATTGCATAAAG | SEQ ID NO: 40 |
| VIL1 | GCTCCAGTCCCTAAGG | SEQ ID NO: 41 |

Example 2

Esophageal Cancer

Figure 18C:
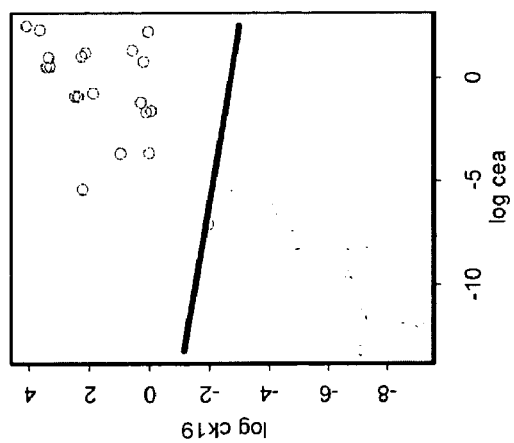
FIG. 18A-O provide scatter plots illustrating the ability of two-marker systems to distinguish between benign and malignant cells in a lymph node of an esophageal cancer patient (negative—gray circle; positive—black circle).
Figure 18B:
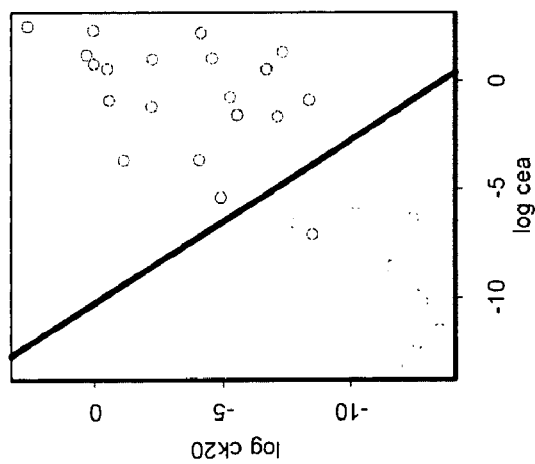
Figure 18A:
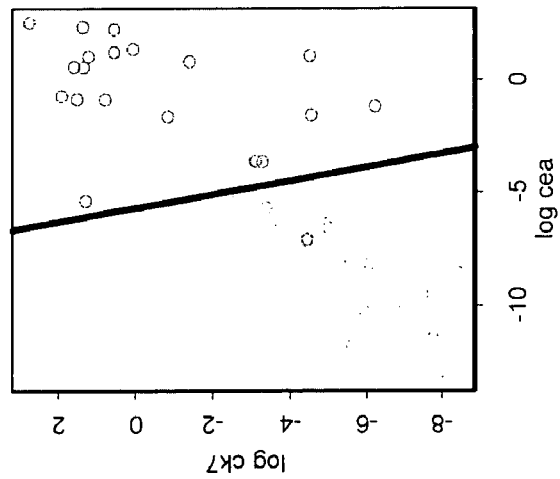
Figure 18F:
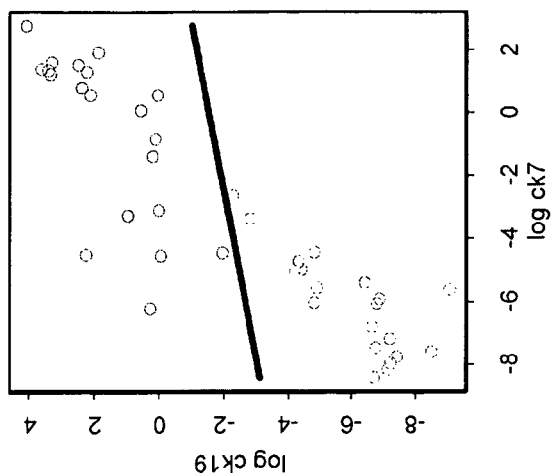
Figure 18E:
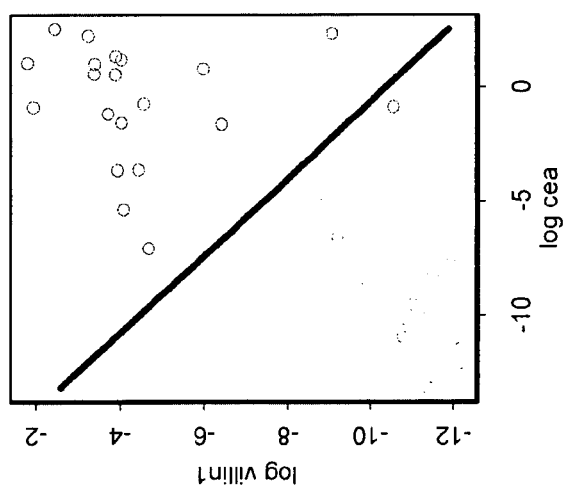
Figure 18D:
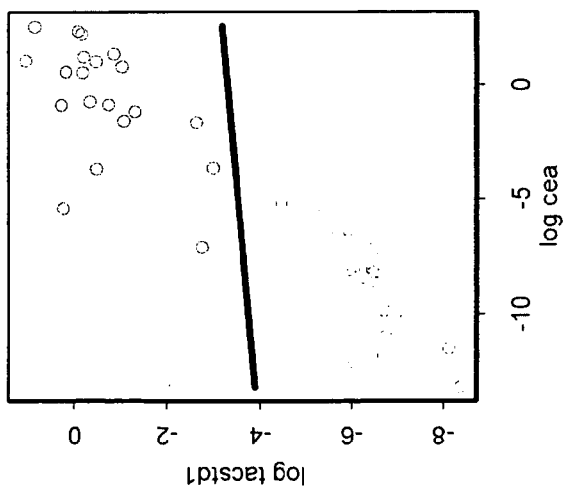
Figure 18I:
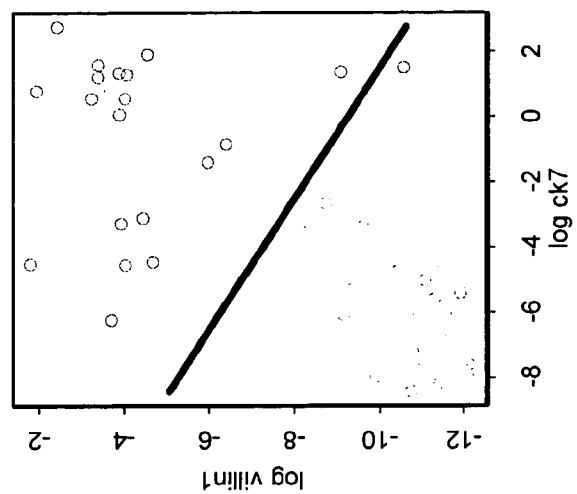
Figure 18H:
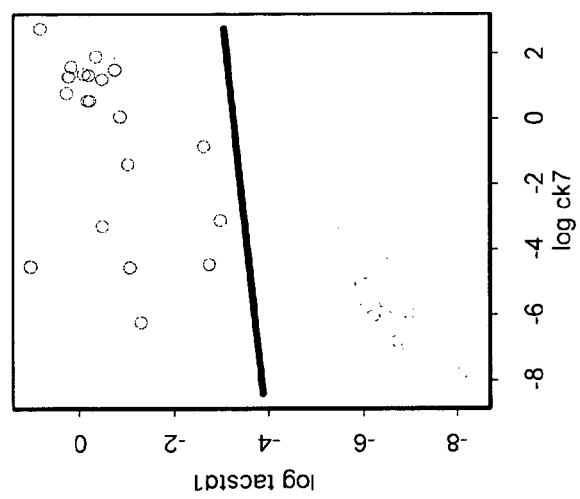
Figure 18G:
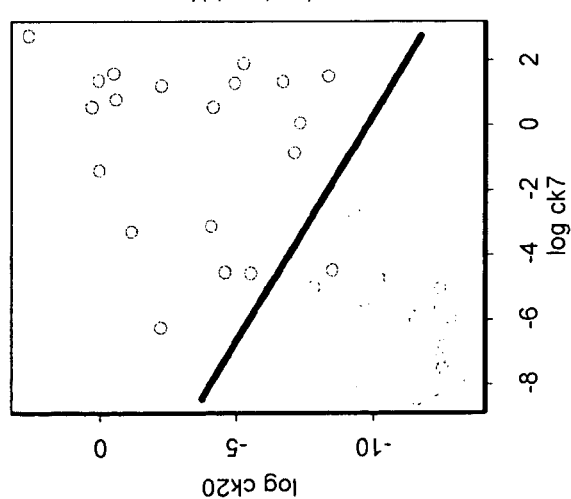
Figure 18L:
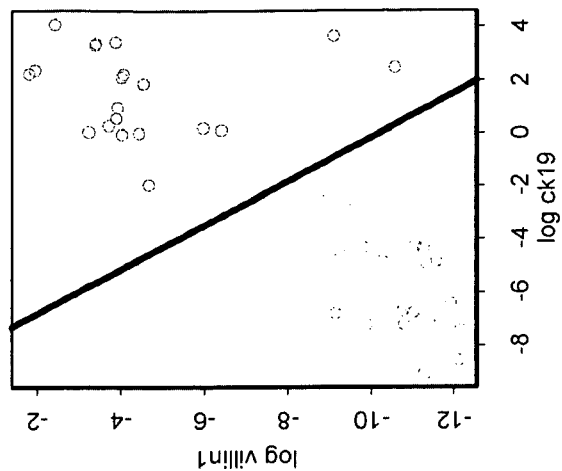
Figure 18K:
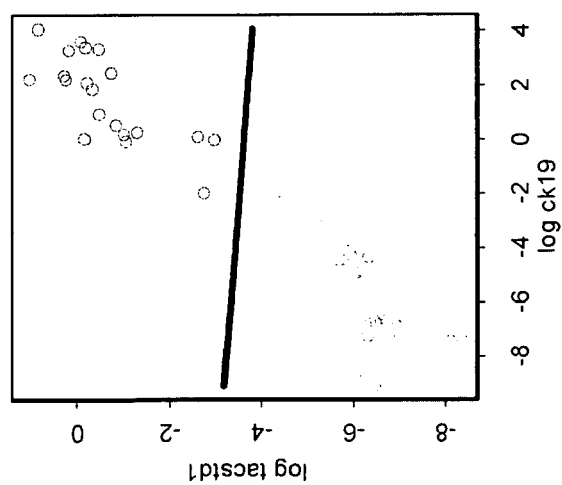
Figure 18J:
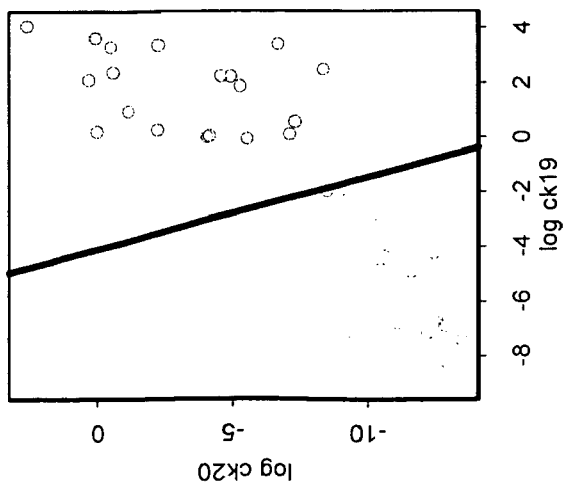
Figure 18O:
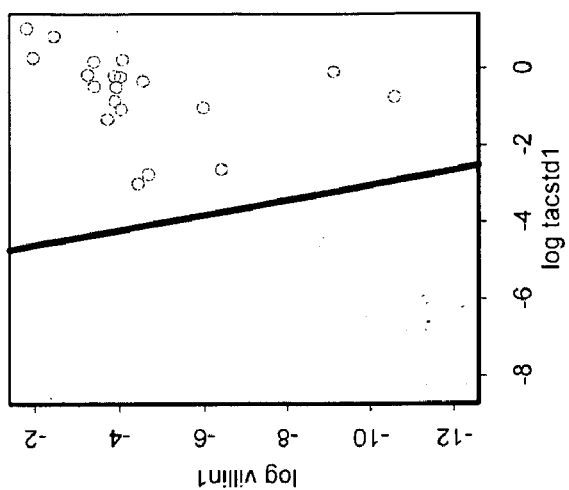
Figure 18N:
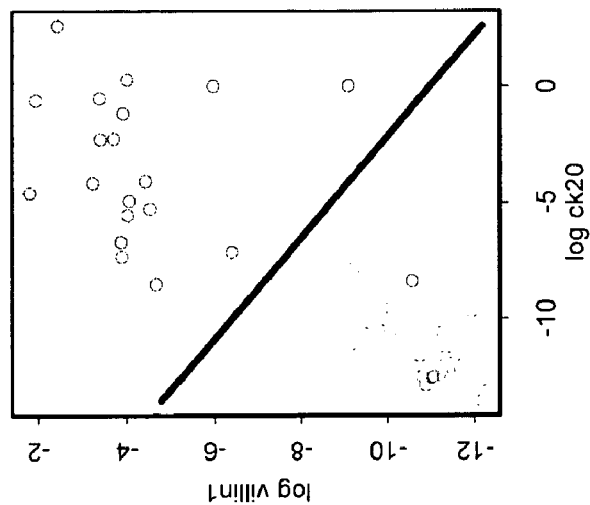
Figure 18M:
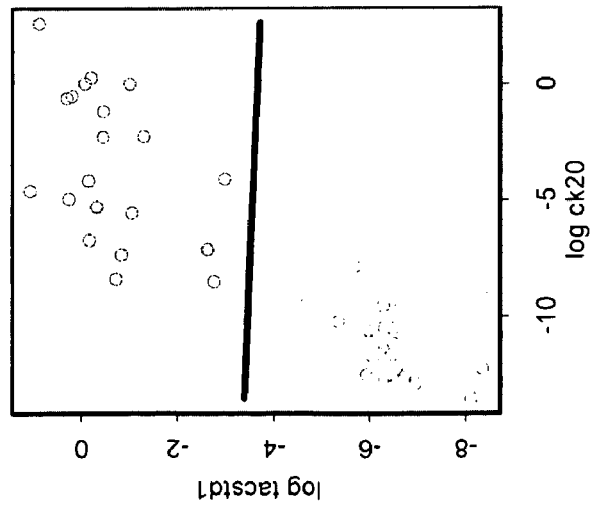

Expression levels of CEA, CK7, CK19, CK20, TACSTD1 and VIL1 were determined by the methods described in Example 1. FIG. 17 is a scatter plot showing the expression levels of CEA, CK7, CK19, CK20, TACSTD1 and VIL1 in primary tumor, tumor-positive lymph nodes and benign lymph nodes. FIGS. 18A-O provide scatter plots illustrating the ability of two-marker systems to distinguish between benign and malignant cells in a lymph node. Tables D and E provide the raw data from which the graphs of FIGS. 17 and 18A-O were generated. This data illustrates the strong correlation of expression of CEA, CK7, CK19, CK20, TACSTD1 and VIL1 markers, alone or in combination, in sentinel lymph nodes with the presence of malignant cells arising from an esophageal cancer in the sentinel lymph nodes.

TABLE D

Single Marker Prediction Characteristics for Esophageal Cancer

| | Observed Data | | | | Parametric Bootstrap Estimates* | | |
|---|---|---|---|---|---|---|---|
| | Sensitivity | Specificity | AUC | Classification Accuracy | Sensitivity | Specificity | Classification Accuracy |
| CEA | .95 | .95 | .98 | .95 | .93 | .93 | .93 |
| CK7 | .95 | .86 | .94 | .90 | .82 | .89 | .85 |
| CK19 | 1.0 | 1.0 | 1.0 | 1.0 | .99 | .94 | 97 |
| CK20 | 1.0 | .95 | .995 | .98 | .98 | .92 | .95 |
| TACSTD1 | 1.0 | 1.0 | 1.0 | 1.0 | .96 | .99 | .98 |
| Villin1 | .95 | .95 | .98 | .95 | .92 | .93 | .92 | optimism = .02-.05

1000 parametric bootstrap samples of lymph node expression levels were generated and a new decision rule based on the most accurate cutoff was formulated each time (total of 1000 decision rules). The bootstrap estimates are the average prediction properties from classifying the original 41 lymph nodes 1000 times.

TABLE E

Two Marker Prediction Characteristics for Esophageal Cancer

| | Observed Data | | | Parametric Bootstrap Estimates* | | |
|---|---|---|---|---|---|---|
| | Sensitivity | Specificity | Classification Accuracy | Sensitivity | Specificity | Classification Accuracy |
| CEA + CK7 | .95 | 1.0 | .98 | .93 | .99 | .96 |
| CEA + CK19 | .95 | 1.0 | .98 | .97 | .99 | .98 |
| CEA + CK20 | .95 | 1.0 | .98 | .97 | .99 | .97 |
| CEA + TACSTD1 | 1.0 | 1.0 | 1.0 | .99 | 1.0 | .99 |
| CEA + Villin1 | .95 | 1.0 | .98 | .95 | 1.0 | .98 |
| CK7 + CK19 | 1.0 | 1.0 | 1.0 | .99 | .99 | .99 |
| CK7 + CK20 | .95 | 1.0 | .98 | .93 | .99 | .97 |
| CK7 + TACSTD1 | 1.0 | 1.0 | 1.0 | .99 | 1.0. | .99 |
| CK7 + Villin1 | .95 | 1.0 | .98 | .95 | .99 | .98 |
| CK19 + CK20 | .95 | 1.0 | .98 | .97 | .99 | .98 |
| CK19 + TACSTD1 | 1.0 | 1.0 | 1.0 | .99 | 1.0 | .99 |
| CK19 + Villin1 | 1.0 | 1.0 | 1.0 | .99 | .99 | .99 |
| CK20 + TACSTD1 | 1.0 | 1.0 | 1.0 | .99 | 1.0 | .99 |
| CK20 + Villin1 | .95 | 1.0 | .98 | .94 | 1.0 | .97 |
| TACSTD1 + Villin1 | 1.0 | 1.0 | 1.0 | .99 | 1.0 | .99 |

1000 parametric bootstrap samples of 41 lymph node marker pair expression levels were generated. For each new sample a new decision rule was devised to split the region into 2 zones equal prediction probability (see methods) (total of 1000 decision rules). The bootstrap estimates are the average prediction properties from classifying the original 41 lymph nodes 1000 times.

Example 3

Head and Neck Cancer

Figure 19:
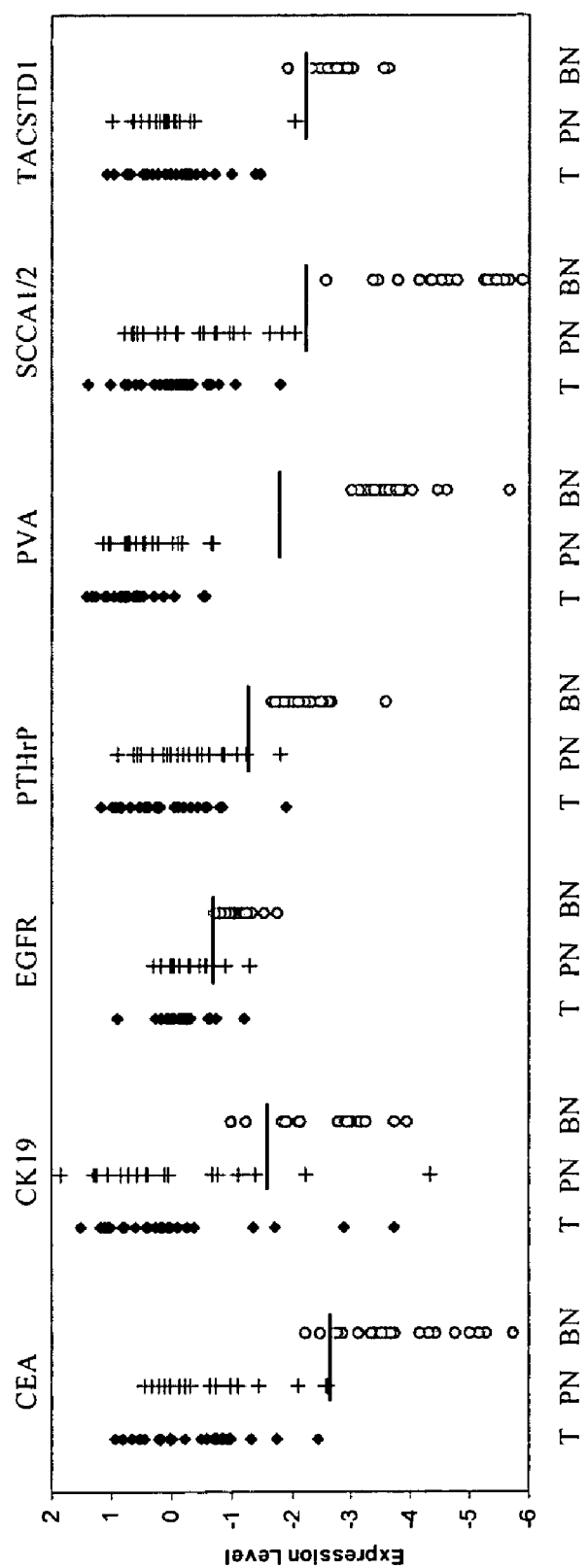
FIG. 19 is a scatter plot showing the expression levels of CEA, CK19, PThRP, PVA, SCCA1.2 and TACSTD1 in primary tumor, tumor-positive lymph nodes and benign lymph nodes of a head & neck cancer patient.
Figures 20D, 20E, 20F:
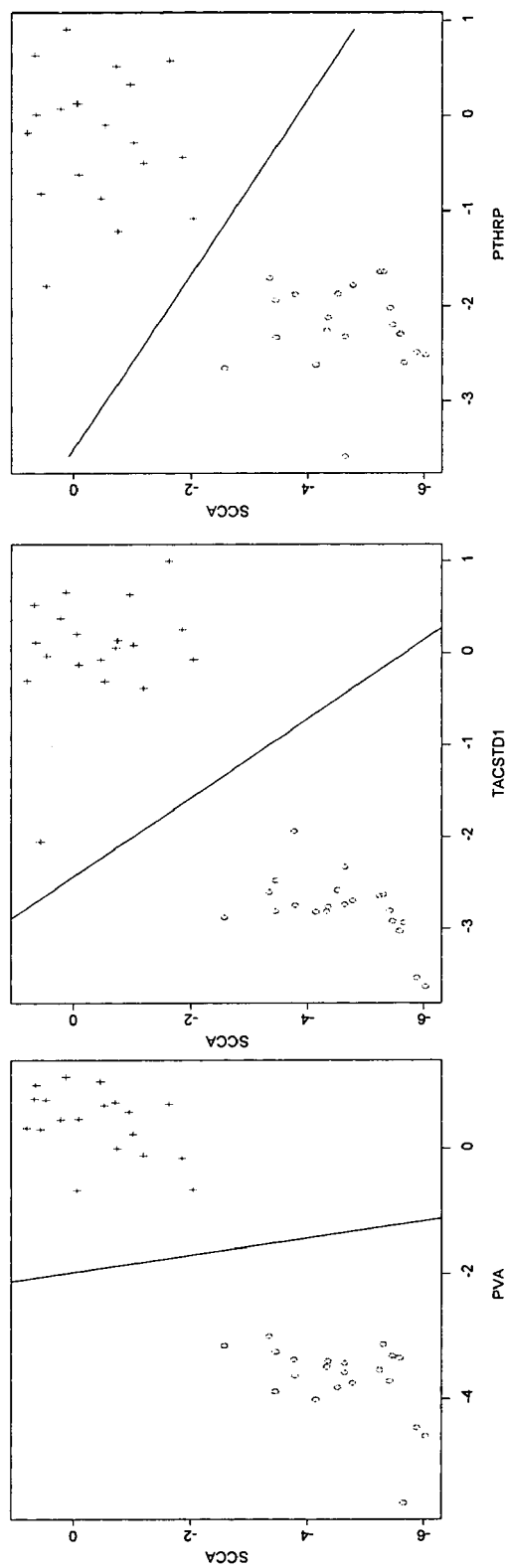

FIG. 19 is a scatter plot showing the expression levels of CEA, CK19, PTHrP, PVA, SCCA1.2 and TACSTD1 in primary tumor, tumor-positive lymph nodes and benign lymph nodes. FIGS. 20A-F provides scatter plots illustrating the ability of two-marker systems to distinguish between benign and malignant cells in a lymph node. Tables F and G provide the raw data from which the graphs of FIGS. 19 and 20A-F were generated. This data illustrates the strong correlation between expression of CEA, CK19, PTHrP, PVA, SCCA1.2 and TACSTD1 markers, alone or in combination, in sentinel lymph nodes and the presence of malignant cells arising from a squamous cell carcinoma of the head and neck in the sentinel lymph nodes.

TABLE F

Single Marker Prediction Characteristics-Head and Neck Cancer

| | Observed Data | | | | Non Parametric Bootstrap Estimates* | | | |
|---|---|---|---|---|---|---|---|---|
| | Sensitivity | Specificity | AUC | Classification Accuracy | Sensitivity | Specificity | Classification Accuracy | bias** |
| CEA | 1.0 | .905 | .990 | .950 | .974 | .880 | .872 | .078 |
| CK19 | .895 | .905 | .917 | .900 | .867 | .880 | .872 | .028 |
| EGFR | .895 | 1.0 | .945 | .947 | .873 | .979 | .925 | .022 |
| PTHrP | .947 | 1.0 | .990 | .975 | .938 | .988 | .963 | .012 |
| PVA | 1.0 | 1.0 | 1.0 | 1.0 | 1.0 | 1.0 | 1.0 | .000 |
| SCCA1.2 | 1.0 | 1.0 | 1.0 | 1.0 | .998 | .985 | .991 | .009 |
| TACSTD1 | 1.0 | .952 | .997 | .975 | .983 | .944 | .962 | .013 |

*500 bootstrap samples of lymph node expression levels were generated and a new decision rule based on the most accurate cutoff was formulated each time (total of 500 decision rules). 500 bootstrap samples of lymph node expression levels were generated and a new decision rule based on the most accurate cutoff was formulated each time (total of 500 decision rules).The optimism in for each bootstrap sample is calculated as the difference between the classification statistic applied to the original data and applied to the bootstrap data. The average over all bootstrap samples is computed and reported as the bias in the values derived from the observed data (Efron's enhanced bootstrap prediction error estimate, see Efron and Tibshirani, An Introduction to the Bootstrap, Chapman and Hall/CRC Press Boca Raton, 1993).
**bias = enhanced bootstrap estimate of optimism, or the amount that classification accuracy is overestimated when tested on the original data.

TABLE G

Two Marker Prediction Characteristics for Head & Neck Cancer

| | Observed Data | | | Non Parametric Bootstrap Estimates | | | |
|---|---|---|---|---|---|---|---|
| | Sensitivity | Specificity | Classification Accuracy | Sensitivity | Specificity | Classification Accuracy | Bias** |
| PVA + TACSTD1 | 1.0 | 1.0 | 1.0 | .993 | 1.0 | .997 | .003 |
| PVA + PTHrP | 1.0 | 1.0 | 1.0 | 1.0 | 1.0 | 1.0 | .000 |
| PVA + SCCA1.2 | 1.0 | 1.0 | 1.0 | 1.0 | 1.0 | 1.0 | .000 |
| TACSTD1 + PTHrP | .947 | 1.0 | .975 | .944 | 1.0 | .974 | .001 |
| TACSTD1 + SCCA1.2 | 1.0 | 1.0 | 1.0 | .984 | 1.0 | .992 | .008 |
| PTHrP + SCCA1.2 | 1.0 | 1.0 | 1.0 | 1.0 | 1.0 | 1.0 | .000 |

*500 bootstrap samples of lymph node expression levels were generated and a new decision rule based on the most accurate cutoff was formulated each time (total of 500 decision rules). 500 bootstrap samples of lymph node expression levels were generated and a new decision rule based on the most accurate cutoff was formulated each time (total of 500 decision rules). The optimism in for each bootstrap sample is calculated as the difference between the classification statistic applied to the original data and applied to the bootstrap data. The average over all bootstrap samples is computed and reported as the bias in the values derived from the observed data (Efron's enhanced bootstrap prediction error estimate, see Efron and Tibshirani, An Introduction to the Bootstrap, Chapman and Hall/CRC Press Boca Raton, 1993).
**bias = enhanced bootstrap estimate of optimism, or the amount that classification accuracy is overestimated when tested on the original data.

Example 4

Melanoma

Figure 21:
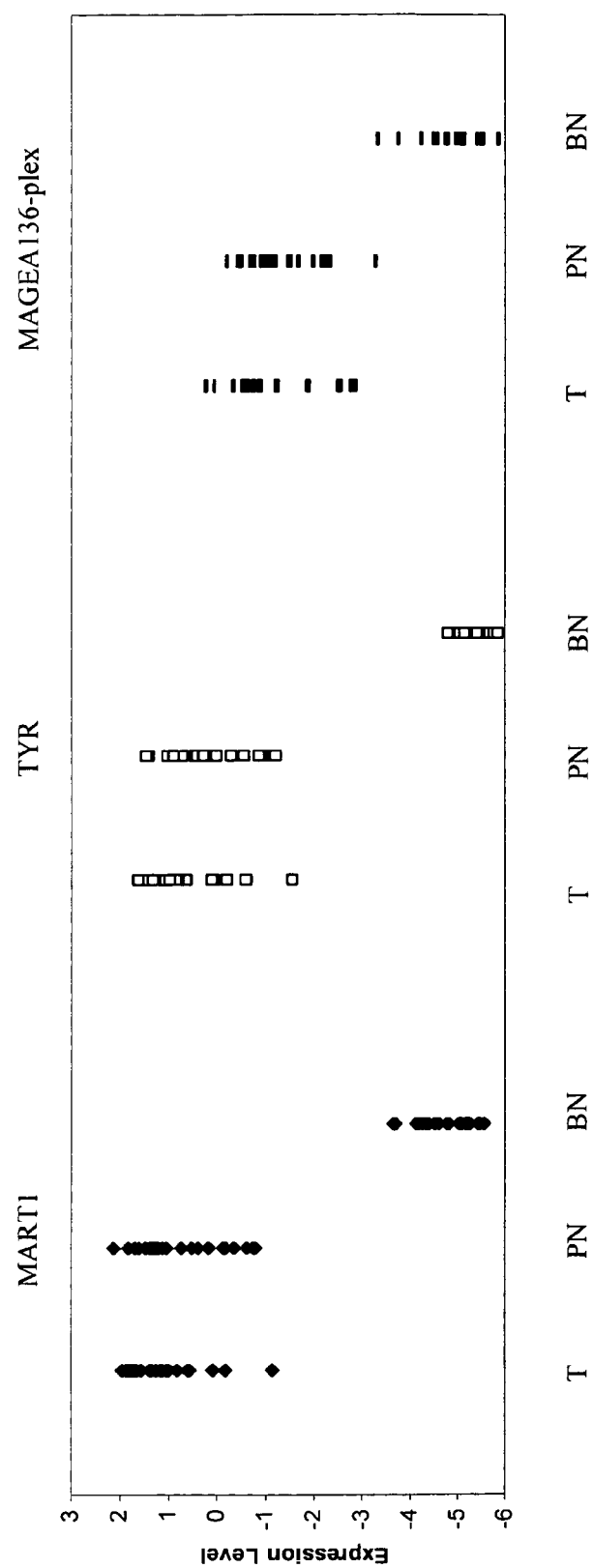
FIG. 21 is a scatter plot showing the expression levels of MART1, TYR and MAGEA136-plex in primary tumor, tumor-positive lymph nodes and benign lymph nodes of a melanoma patient.
Figure 22A:
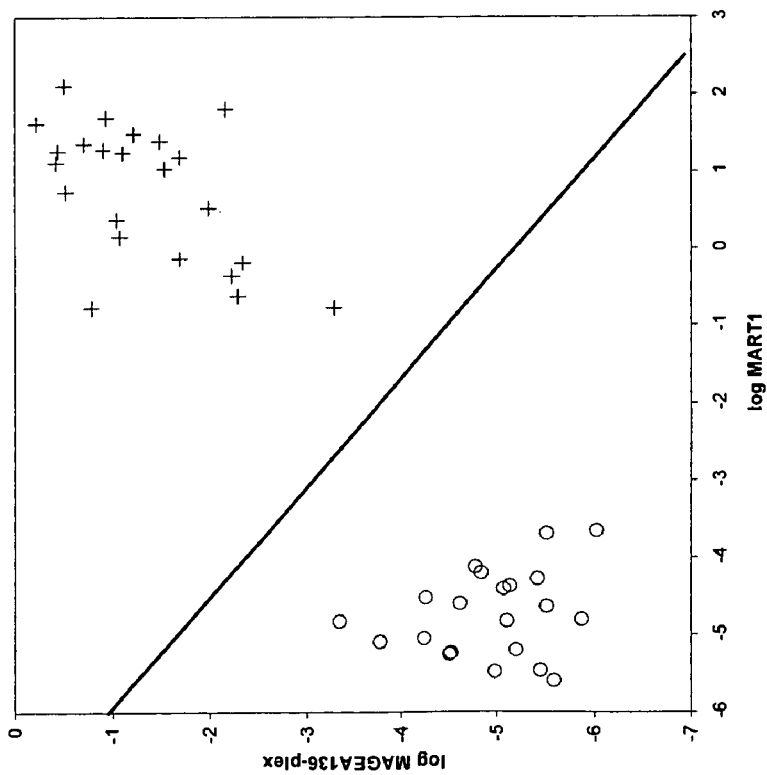
FIGS. 22A and 22B provide scatter plots illustrating the ability of two-marker systems to distinguish between benign and malignant cells in a lymph node of a melanoma patient (negative—circle; positive—"+").
Figure 22B:
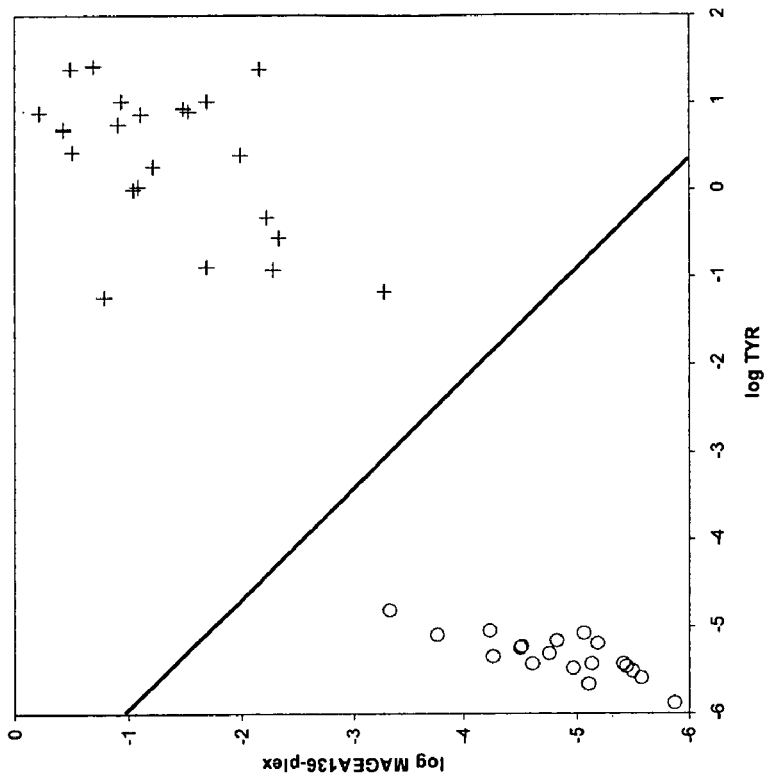

FIG. 21 is a scatter plot showing the expression levels of MART1, TYR and MAGEA136-plex in primary tumor, tumor-positive lymph nodes and benign lymph nodes. FIGS. 22A and 22B provide scatter plots illustrating the ability of two-marker systems to distinguish between benign and malignant cells in a lymph node. This data illustrates the strong correlation between expression of MART1, TYR and MAGEA136-plex markers, alone or in combination, in sentinel lymph nodes and the presence of malignant cells arising from melanoma in the sentinel lymph nodes.

Example 5

Colon Cancer

Figure 23:
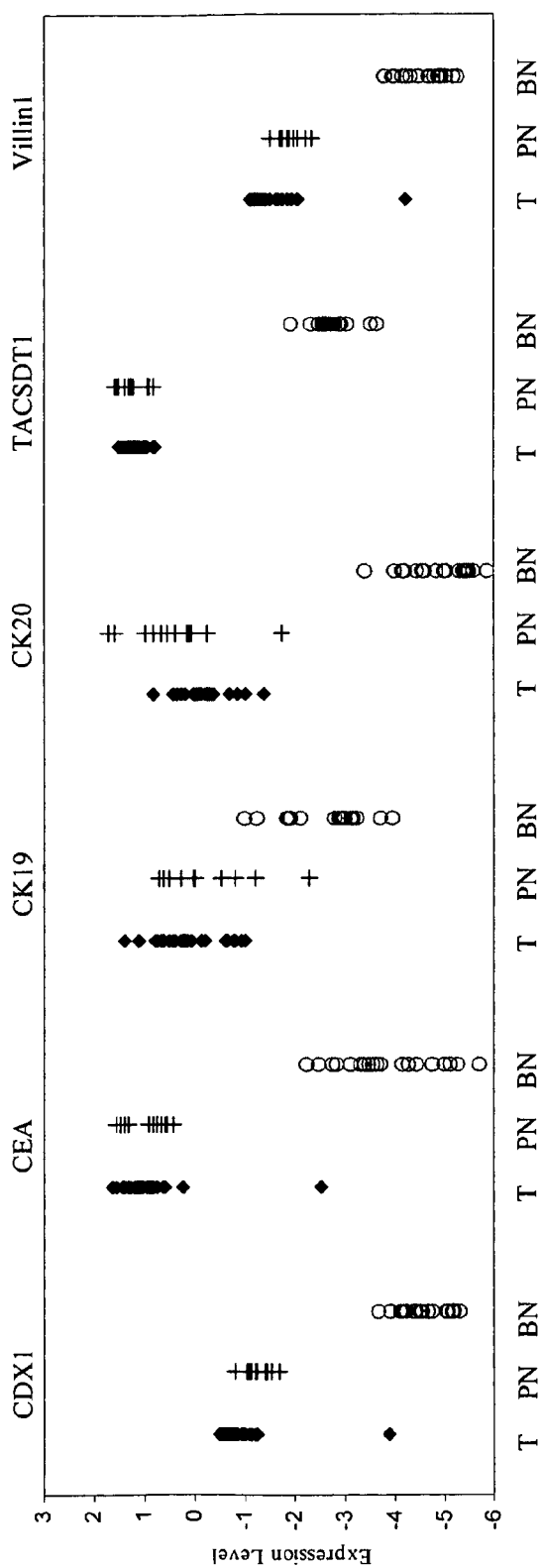
FIG. 23 is a scatter plot showing the expression levels of CDX1, CEA, CK19, CK20, TACSTD1 and VIL1 in primary tumor, tumor-positive lymph nodes and benign lymph nodes of a colon cancer patient.

FIG. 23 is a scatter plot showing the expression levels of CDX1, CEA, CK19, CK20, TACSTD1 and VIL1 in primary tumor, tumor-positive lymph nodes and benign lymph nodes. This data illustrates the strong correlation between expression of CDX1, CEA, CK19, CK20, TACSTD1 and VIL1 markers, in sentinel lymph nodes and the presence of malignant cells arising from colon cancer in the sentinel lymph nodes.

We claim:

1. A method of identifying expression of markers indicative of the presence of displaced cells of a squamous cell carcinoma of the head & neck in a lymph node of a human patient suspected of having a squamous cell carcinoma of the head & neck, comprising detecting a quantity of pemphigus vulgaris antigen mRNA in an RNA sample prepared from the lymph node of the patient and determining if pemphigus vulgaris antigen mRNA is overabundant in the RNA sample as compared to a level of pemphigus vulgaris antigen mRNA in benign lymph nodes, wherein the overabundance pemphigus vulgaris antigen mRNA is statistically significant and indicates the presence of displaced cells of squamous cell carcinoma of the head & neck in the lymph node, and wherein the overabundance of the pemphigus vulgaris mRNA identifies the expression of RNA indicative of the presence of displaced cells of a squamous cell carcinoma of the head & neck in the lymph node of the patient.

2. The method of claim 1, comprising determining if pemphigus vulgaris antigen mRNA is overabundant in an RNA sample prepared from the lymph node of the patient as compared to the level of pemphigus vulgaris antigen mRNA in benign lymph nodes, wherein the overabundance of the pemphigus vulgaris antigen mRNA indicative of the presence of displaced cells of a squamous cell carcinoma of the head & neck is at least 100-fold as compared to a level of pemphigus vulgaris antigen mRNA in benign lymph nodes.

3. The method of claim 1, further comprising determining if tumor-associated calcium signal transducer 1 mRNA is overabundant in an RNA sample prepared from the lymph node of the patient as compared to the level of tumor-associated calcium signal transducer mRNA in benign lymph nodes.

4. The method of claim 1, in which the level of pemphigus vulgaris antigen mRNA in one or more benign lymph nodes is determined by quantifying pemphigus vulgaris antigen mRNA levels in benign lymph nodes as determined by pathology.

5. The method of claim 1, wherein a nucleic acid amplification assay is used to quantify levels of the pemphigus vulgaris antigen mRNA in the RNA sample.

6. The method of claim 5, wherein the nucleic acid amplification assay is one of a PCR assay and an isothermic amplification assay.

7. The method of claim 6, wherein the nucleic acid amplification assay is an assay selected from the group consisting of RT-PCR, QRT-PCR, rolling circle amplification and nucleic acid sequenced-based amplification assays.

8. The method of claim 7, wherein the assay is a rolling circle amplification assay in which a padlock primer is used.

9. The method of claim 5, wherein the assay is a multiplex assay.

10. The method of claim 5, wherein the assay is an RT-PCR assay.

11. The method of claim 10, wherein the RT-PCR assay uses one or more primer pairs for amplification of pemphigus vulgaris antigen mRNA.

12. The method of claim 11, wherein the primer pairs consist essentially of at least ten contiguous nucleotides of one or both of SEQ ID NO: 28 and positions 208-304 of SEQ ID NO: 11.

13. A method of identifying expression of markers indicative of the presence of displaced cells of a squamous cell carcinoma of the head & neck in a lymph node of a human patient suspected of having a squamous cell carcinoma of the head & neck comprising:
   a. detecting a quantity of pemphigus vulgaris antigen mRNA or the combination of a pemphigus vulgaris antigen mRNA and a tumor-associated calcium signal transducer 1 mRNA from a lymph node of the human patient; and
   b. determining if the quantity of the pemphigus vulgaris antigen mRNA, or the combination of the pemphigus vulgaris antigen mRNA and the tumor-associated calcium signal transducer 1 mRNA in the RNA sample is overabundant as compared to an amount of the pemphigus vulgaris antigen mRNA, or the combination of the pemphigus vulgaris antigen mRNA and the tumor-associated calcium signal transducer 1 mRNA, found in RNA samples prepared from benign lymph nodes,
   wherein the overabundance of the pemphigus vulgaris antigen mRNA, or the combination of the pemphigus vulgaris antigen mRNA and the tumor-associated calcium signal transducer 1 mRNA, is statistically significant and indicates the presence of displaced cells of squamous cell carcinoma of the head & neck in the lymph node of the patient.

14. The method of claim 13, comprising quantifying a level of the pemphigus vulgaris antigen mRNA in an RNA sample prepared from the lymph node of the human patient and determining if the quantity of the pemphigus vulgaris antigen mRNA in the RNA sample is overabundant as compared to an amount of the pemphigus vulgaris antigen mRNA in RNA samples prepared from benign lymph nodes, and wherein the overabundance of the pemphigus vulgaris antigen mRNA that is sufficiently large to identify the presence of displaced cells of squamous cell carcinoma of the head & neck in the lymph node is at least 100-fold higher than the amount of the pemphigus vulgaris antigen mRNA in RNA samples prepared from benign lymph nodes.

15. The method of claim 13, comprising quantifying the combination of a pemphigus vulgaris antigen mRNA and a tumor-associated calcium signal transducer 1 mRNA in an RNA sample prepared from the lymph node of the human patient and determining if the quantity of the combination of the pemphigus vulgaris antigen mRNA and the tumor-associated calcium signal transducer 1 mRNA in the RNA sample is overabundant as compared to an amount of the combination of the pemphigus vulgaris antigen mRNA and the tumor-associated calcium signal transducer 1 mRNA in RNA samples prepared from benign lymph nodes.

* * * * *

```
SEQUENCE LISTING

<160> NUMBER OF SEQ ID NOS: 40

<210> SEQ ID NO 1
<211> LENGTH: 1699
<212> TYPE: DNA
<213> ORGANISM: Homo sapiens

<400> SEQUENCE: 1
aggtgagcgg ttgctcgtcg tcggggcggc cggcagcggc ggctccaggg cccagcatgc      60 gcggggacc  ccgcggccac catgtatgtg ggctatgtgc tggacaagga ttcgcccgtg     120
taccccggcc cagccaggcc agccagcctc ggcctgggcc cggcaaacta cggcccccg     180 gccccgcccc cggcgccccc gcagtacccc gacttctcca gctactctca cgtggagccg     240 gccccgcgc  ccccgacggc ctgggggggcg cccttccctg cgcccaagga cgactgggcc    300
gccgcctacg gcccgggccc cgcggcccct gccgccagcc cagcttcgct ggcattcggg     360 cccctccag  actttagccc ggtgccggcg cccctgggc  ccggcccggg cctcctggcg     420
cagcccctcg ggggcccggg cacaccgtcc tcgcccgag cgcagaggcc gacgccctac      480
gagtggatgc ggcgcagcgt ggcggccgga ggcggcggtg gcagcggtaa gactcggacc     540
aaggacaagt accgcgtggt ctacaccgac caccaacgcc tggagctgga gaaggagttt     600
cattacagcc gttacatcac aatccggcgg aaatcagagc tggctgccaa tctggggctc     660
actgaacggc aggtgaagat ctggttccaa aaccggcggg caaaggagcg caaagtgaac     720
aagaagaaac agcagcagca acagccccca cagccgccga tggcccacga catcacggcc     780
accccagccg ggccatccct gggggggcctg tgtcccagca acaccagcct cctggccacc     840
tcctctccaa tgcctgtgaa agaggagttt ctgccatagc cccatgccca gcctgtgcgc     900
cgggggacct gggggactcgg gtgctgggag tgtggctcct gtgggcccag gaggtctggt     960
ccgagtctca gccctgacct tctgggacat ggtggacagt cacctatcca ccctctgcat    1020
ccccttggcc cattgtgtgc agtaagcctg ttggataaag accttccagc tcctgtgttc    1080
tagacctctg ggggataagg gagtccaggg tggatgatct caatctcccg tgggcatctc    1140
aagccccaaa tggttggggg aggggcctag acaaggctcc aggcccacc  tcctcctcca    1200
```

-continued

```
tacgttcaga ggtgcagctg gaggcctgtg tggggaccac actgatcctg gagaaaaggg    1260
atggagctga aaaagatgga atgcttgcag agcatgacct gaggagggag gaacgtggtc    1320
aactcacacc tgcctcttct gcagcctcac ctctacctgc cccatcata agggcactga    1380 gcccttccca ggctggatac taagcacaaa gcccatagca ctgggtctg atggctgctc     1440 cactgggtta cagaatcaca gccctcatga tcattctcag tgagggctct ggattgagag    1500
ggaggccctg ggaggagaga aggggcaga gtcttcccta ccaggtttct acaccccgc      1560 caggctgccc atcagggccc agggagcccc cagaggactt tattcggacc aagcagagct    1620
cacagctgga caggtgttgt atatagagtg gaatctcttg gatgcagctt caagaataaa    1680
tttttcttct cttttcaaa                                                 1699
```

<210> SEQ ID NO 2
<211> LENGTH: 2974
<212> TYPE: DNA
<213> ORGANISM: Homo sapiens

<400> SEQUENCE: 2

```
ctcagggcag agggaggaag gacagcagac cagacagtca cagcagcctt gacaaaacgt      60
tcctggaact caagctcttc tccacagagg aggacagagc agacagcaga gaccatggag    120 tctcccctcgg cccctcccca cagatggtgc atccctggc agaggctcct gctcacagcc    180
tcacttctaa ccttctggaa cccgcccacc actgccaagc tcactattga atccacgccg    240
ttcaatgtcg cagagggaa ggaggtgctt ctacttgtcc acaatctgcc ccagcatctt     300
tttggctaca gctggtacaa aggtgaaaga gtggatggca accgtcaaat tataggatat    360
gtaataggaa ctcaacaagc taccccaggg cccgcataca gtggtcgaga gataatatac    420
cccaatgcat ccctgctgat ccagaacatc atccagaatg acacaggatt ctacacccta    480
cacgtcataa agtcagatct tgtgaatgaa gaagcaactg ccagttccg ggtatacccg     540 gagctgccca agccctccat ctccagcaac aactccaaac ccgtggagga caaggatgct    600
gtggccttca cctgtgaacc tgagactcag gacgcaacct acctgtggtg ggtaaacaat    660
cagagcctcc cggtcagtcc caggctgcag ctgtccaatg gcaacaggac cctcactcta    720
ttcaatgtca caagaaatga cacagcaagc tacaaatgtg aaacccagaa cccagtgagt    780
gccaggcgca gtgattcagt catcctgaat gtcctctatg gcccggatgc ccccaccatt    840 tccccctctaa acacatctta cagatcaggg gaaaatctga acctctcctg ccacgcagcc    900
tctaacccac ctgcacagta ctcttggttt gtcaatggga ctttccagca atccacccaa    960 gagctctta tccccaacat cactgtgaat aatagtggat cctatacgtg ccaagcccat   1020
aactcagaca ctggcctcaa taggaccaca gtcacgacga tcacagtcta tgcagagcca   1080 cccaaacccct tcatcaccag caacaactcc aaccccgtgg aggatgagga tgctgtagcc   1140
ttaacctgtg aacctgagat tcagaacaca acctacctgt ggtgggtaaa taatcagagc   1200
ctcccggtca gtcccaggct gcagctgtcc aatgacaaca ggaccctcac tctactcagt   1260
gtcacaagga tgatgtagg accctatgag tgtggaatcc agaacgaatt aagtgttgac   1320
cacagcgacc cagtcatcct gaatgtcctc tatggcccag acgacccac catttccccc   1380 tcatacacct attaccgtcc aggggtgaac ctcagcctct cctgccatgc agcctctaac   1440
ccacctgcac agtattcttg gctgattgat gggaacatcc agcaacacac acaagagctc   1500
tttatctcca acatcactga gaagaacagc ggactctata cctgccaggc caataactca   1560
gccagtggcc acagcaggac tacagtcaag acaatcacag tctctgcgga gctgcccaag   1620
```

```
ccctccatct ccagcaacaa ctccaaaccc gtggaggaca aggatgctgt ggccttcacc      1680
tgtgaacctg aggctcagaa cacaacctac ctgtggtggg taaatggtca gagcctccca      1740
gtcagtccca ggctgcagct gtccaatggc aacaggaccc tcactctatt caatgtcaca      1800
agaaatgacg caagagccta tgtatgtgga atccagaact cagtgagtgc aaaccgcagt      1860
gacccagtca ccctggatgt cctctatggg ccggacaccc ccatcatttc cccccagac      1920 tcgtcttacc tttcgggagc gaacctcaac ctctcctgcc actcggcctc taacccatcc      1980
ccgcagtatt cttggcgtat caatgggata ccgcagcaac acacacaagt tctctttatc      2040
gccaaaatca cgccaaataa taacgggacc tatgcctgtt ttgtctctaa cttggctact      2100
ggccgcaata attccatagt caagagcatc acagtctctg catctggaac ttctcctggt      2160
ctctcagctg gggccactgt cggcatcatg attggagtgc tggttggggt tgctctgata      2220
tagcagccct ggtgtagttt cttcatttca ggaagactga cagttgtttt gcttcttcct      2280
taaagcattt gcaacagcta cagtctaaaa ttgcttcttt accaaggata tttacagaaa      2340
agactctgac cagagatcga gaccatccta gccaacatcg tgaaacccca tctctactaa      2400
aaatacaaaa atgagctggg cttggtggcg cgcacctgta gtcccagtta ctcgggaggc      2460
tgaggcagga gaatcgcttg aacccgggag gtggagattg cagtgagccc agatcgcacc      2520
actgcactcc agtctggcaa cagagcaaga ctccatctca aaagaaaag aaaagaagac      2580 tctgacctgt actcttgaat acaagtttct gataccactg cactgtctga aatttccaa      2640 aactttaatg aactaactga cagcttcatg aaactgtcca ccaagatcaa gcagagaaaa      2700
taattaattt catgggacta aatgaactaa tgaggattgc tgattcttta aatgtcttgt      2760
ttcccagatt tcaggaaact tttttctttt taagctatcc actcttacag caatttgata      2820
aaatatactt ttgtgaacaa aaattgagac atttacattt tctccctatg tggtcgctcc      2880
agacttggga aactattcat gaatatttat attgtatggt aatatagtta ttgcacaagt      2940
tcaataaaaa tctgctcttt gtataacaga aaaa                                 2974
```

<210> SEQ ID NO 3  
<211> LENGTH: 1753  
<212> TYPE: DNA  
<213> ORGANISM: Homo sapiens

<400> SEQUENCE: 3

```
cagccccgcc cctacctgtg gaagcccagc cgcccgctcc cgcggataaa aggtgcggag        60
tgtccccgag gtcagcgagt gcgcgctcct cctcgcccgc cgctaggtcc atcccggccc       120
agccaccatg tccatccact tcagctcccc ggtattcacc tcgcgctcag ccgccttctc       180
gggccgcggc gcccaggtgc gcctgagctc cgctcgcccc ggcggccttg gcagcagcag       240
cctctacggc ctcggcgcct cgcggccgcg cgtggccgtg cgctctgcct atggggccc        300 ggtgggcgcc ggcatccgcg aggtcaccat taaccagagc ctgctggccc cgctgcggct       360
ggacgccgac ccctcctcc agcgggtgcg ccaggaggag agcgagcaga tcaagaccct       420
caacaacaag tttgcctcct tcatcgacaa ggtgcggttt ctggagcagc agaacaagct       480
gctggagacc aagtggacgc tgctgcagga gcagaagtcg gccaagagca gccgcctccc       540
agacatcttt gaggcccaga ttgctggcct tcggggtcag cttgaggcac tgcaggtgga       600
tgggggccgc ctggaggcgg agctgcggag catgcaggat gtggtggagg acttcaagaa       660
taagtacgaa gatgaaatta accgccgcac agctgctgag aatgagtttg tggtgctgaa       720
```

-continued

| | |
|---|---:|
| gaaggatgtg gatgctgcct acatgagcaa ggtggagctg gaggccaagg tggatgccct | 780 |
| gaatgatgag atcaacttcc tcaggaccct caatgagacg gagttgacag agctgcagtc | 840 |
| ccagatctcc gacacatctg tggtgctgtc catggacaac agtcgctccc tggacctgga | 900 |
| cggcatcatc gctgaggtca aggcacagta tgaggagatg gccaaatgca gccgggctga | 960 |
| ggctgaagcc tggtaccaga ccaagtttga gaccctccag gcccaggctg gaagcatgg | 1020 |
| ggacgacctc cggaataccc ggaatgagat ttcagagatg aaccgggcca tccagaggct | 1080 |
| gcaggctgag atcgacaaca tcaagaacca gcgtgccaag ttggaggccg ccattgccga | 1140 |
| ggctgaggag cgtggggagc tggcgctcaa ggatgctcgt gccaagcagg aggagctgga | 1200 |
| agccgccctg cagcgggcca agcaggatat ggcacggcag ctgcgtgagt accaggaact | 1260 |
| catgagcgtg aagctggccc tggacatcga gatcgccacc taccgcaagc tgctggaggg | 1320 |
| cgaggagagc cggttggctg agatggagt gggagccgtg aatatctctg tgatgaattc | 1380 |
| cactggtggc agtagcagtg gcggtggcat tgggctgacc ctcgggggaa ccatgggcag | 1440 |
| caatgccctg agcttctcca gcagtgcggg tcctgggctc ctgaaggctt attccatccg | 1500 |
| gaccgcatcc gccagtcgca ggagtgcccg cgactgagcc gcctcccacc actccactcc | 1560 |
| tccagccacc acccacaatc acaagaagat tcccacccct gcctcccatg cctggtccca | 1620 |
| agacagtgag acagtctgga aagtgatgtc agaatagctt ccaataaagc agcctcattc | 1680 |
| tgaggcctga gtgatccacg tgaaaaaaaa aaaaaaaaaa aaaaaaaaaa aaaaaaaaaa | 1740 |
| aaaaaaaaaa aaa | 1753 |

<210> SEQ ID NO 4
<211> LENGTH: 1440
<212> TYPE: DNA
<213> ORGANISM: Homo sapiens

<400> SEQUENCE: 4

| | |
|---|---:|
| cgcccctgac accattcctc ccttccccc tccaccggcc gcgggcataa aaggcgccag | 60 |
| gtgagggcct cgccgctcct cccgcgaatc gcagcttctg agaccagggt tgctccgtcc | 120 |
| gtgctccgcc tcgccatgac ttcctacagc tatcgccagt cgtcggccac gtcgtccttc | 180 |
| ggaggcctgg gcggcggctc cgtgcgtttt gggccggggg tcgcctttcg cgcgcccagc | 240 |
| attcacgggg gctccggcgg ccgcggcgta tccgtgtcct ccgcccgctt tgtgtcctcg | 300 |
| tcctcctcgg gggcctacgg cggcggctac ggcggcgtcc tgaccgcgtc cgacgggctg | 360 |
| ctggcgggca acgagaagct aaccatgcag aacctcaacg accgcctggc ctcctacctg | 420 |
| gacaaggtgc gcgccctgga ggcggccaac ggcgagctag aggtgaagat ccgcgactgg | 480 |
| taccagaagc aggggcctgg gccctcccgc gactacagcc actactacac gaccatccag | 540 |
| gacctgcggg acaagattct tggtgccacc attgagaact ccaggattgt cctgcagatc | 600 |
| gacaatgccg tctggctgc agatgacttc gaaccaagt tgagacgga acaggctctg | 660 |
| cgcatgagcg tggaggccga catcaacggc ctgcgcaggg tgctggatga gctgaccctg | 720 |
| gccaggaccg acctggagat gcagatcgaa ggcctgaagg aagagctggc ctacctgaag | 780 |
| aagaaccatg aggaggaaat cagtacgctg aggggccaag tgggaggcca ggtcagtgtg | 840 |
| gaggtggatt ccgctccggg caccgatctc gccaagatcc tgagtgacat gcgaagccaa | 900 |
| tatgaggtca tggccgagca gaaccggaag gatgctgaag cctggttcac cagccggact | 960 |
| gaagaattga accgggaggt cgctggccac acggagcagc tccagatgag caggtccgag | 1020 |
| gttactgacc tgcggcgcac ccttcagggt cttgagattg agctgcagtc acagctgagc | 1080 |

```
atgaaagctg ccttggaaga cacactggca gaaacggagg cgcgctttgg agcccagctg   1140
gcgcatatcc aggcgctgat cagcggtatt gaagcccagc tgggcgatgt gcgagctgat   1200
agtgagcggc agaatcagga gtaccagcgg ctcatggaca tcaagtcgcg gctggagcag   1260
gagattgcca cctaccgcag cctgctcgag ggacaggaag atcactacaa caatttgtct   1320
gcctccaagg tcctctgagg cagcaggctc tggggcttct gctgtccttt ggagggtgtc   1380
ttctgggtag agggatggga aggaagggac ccttaccccc ggctcttctc ctgacctgcc   1440

<210> SEQ ID NO 5
<211> LENGTH: 1817
<212> TYPE: DNA
<213> ORGANISM: Homo sapiens

<400> SEQUENCE: 5
caaccatcct gaagctacag gtgctccctc ctggaatctc caatggattt cagtcgcaga     60
agcttccaca gaagcctgag ctcctccttg caggcccctg tagtcagtac agtgggcatg    120
cagcgcctcg ggacgacacc cagcgtttat ggggtgctg gaggccgggg catccgcatc     180
tccaactcca gacacacggt gaactatggg agcgatctca caggcggcgg ggacctgttt    240
gttggcaatg agaaaatggc catgcagaac ctaaatgacc gtctagcgag ctacctagaa    300
aaggtgcgga ccctggagca gtccaactcc aaacttgaag tgcaaatcaa gcagtggtac    360
gaaaccaacg ccccgagggc tggtcgcgac tacagtgcat attacagaca aattgaagag    420
ctgcgaagtc agattaagga tgctcaactg caaaatgctc ggtgtgtcct gcaaattgat    480
aatgctaaac tggctgctga ggacttcaga ctgaagtatg agactgagag aggaatacgt    540
ctaacagtgg aagctgatct ccaaggcctg aataaggtct ttgatgacct aaccctacat    600
aaaacagatt tggagattca aattgaagaa ctgaataaag acctagctct cctcaaaaag    660
gagcatcagg aggaagtcga tggcctacac aagcatctgg gcaacactgt caatgtggag    720
gttgatgctg ctccaggcct gaaccttggc gtcatcatga atgaaatgag gcagaagtat    780
gaagtcatgg cccagaagaa ccttcaagag gccaaagaac agtttgagag acagactgca    840
gttctgcagc aacaggtcac agtgaatact gaagaattaa aaggaactga ggttcaacta    900
acggagctga cgcacctcc ccagagcctt gagatagaac tccagtccca tctcagcatg     960
aaagagtctt tggagcacac tctagaggag accaaggccc gttacagcag ccagttagcc   1020
aacctccagt cgctgttgag ctctctggag gcccaactga tgcagattcg gagtaacatg   1080
gaacgccaga caacgaata ccatatcctt cttgacataa agactcgact tgaacaggaa    1140
attgctactt accgccgcct tctggaagga gaagacgtaa aaactacaga atatcagtta   1200
agcaccctgg aagagagaga tataaagaaa accaggaaga ttaagacagt cgtgcaagaa   1260
gtagtggatg gcaaggtcgt gtcatctgaa gtcaaagagg tggaagaaaa tatctaaata   1320
gctaccagaa ggagatgctg ctgaggtttt gaaagaaatt tggctataat cttatctttg   1380
ctccctgcaa gaaatcagcc ataagaaagc actattaata ctctgcagtg attagaaggg   1440
gtggggtggc gggaatccta tttatcagac tctgtaattg aatataaatg ttttactcag   1500
aggagctgca aattgcctgc aaaaatgaaa tccagtgagc actagaatat ttaaaacatc   1560
attactgcca tctttatcat gaagcacatc aattacaagc tgtagaccac ctaatatcaa   1620
tttgtaggta atgttcctga aaattgcaat acatttcaat tatactaaac ctcacaaagt   1680
agaggaatcc atgtaaattg caaataaacc actttctaat ttttcctgt ttctgaaaaa    1740
```

<210> SEQ ID NO 6
<211> LENGTH: 1722
<212> TYPE: DNA
<213> ORGANISM: Homo sapiens

<400> SEQUENCE: 6

```
cgtagagttc ggccgaagga acctgaccca ggctctgtga ggaggcaagg ttttcagggg        60
acaggccaac ccagaggaca ggattccctg gaggccacag aggagcacca aggagaagat       120
ctgcctgtgg gtcttcattg cccagctcct gcccacactc ctgcctgctg ccctgacgag       180
agtcatcatg tctcttgagc agaggagtct gcactgcaag cctgaggaag cccttgaggc       240
ccaacaagag gccctgggcc tggtgtgtgt gcaggctgcc gcctcctcct cctctcctct       300
ggtcctgggc accctggagg aggtgcccac tgctgggtca acagatcctc cccagagtcc       360
tcagggagcc tccgcctttc ccactaccat caacttcact cgacagaggc aacccagtga       420
gggttccagc agccgtgaag aggaggggcc aagcacctct tgtatcctgg agtccttgtt       480
ccgagcagta atcactaaga aggtggctga tttggttggt tttctgctcc tcaaatatcg       540
agccagggag ccagtcacaa aggcagaaat gctggagagt gtcatcaaaa attacaagca       600
ctgttttcct gagatcttcg gcaaagcctc tgagtccttg cagctggtct ttggcattga       660
cgtgaaggaa gcagaccccca ccggccactc ctatgtcctt gtcacctgcc taggtctctc       720
ctatgatggc ctgctgggtg ataatcagat catgcccaag acaggcttcc tgataattgt       780
cctggtcatg attgcaatgg agggcggcca tgctcctgag gaggaaatct gggaggagct       840
gagtgtgatg gaggtgtatg atgggaggga gcacagtgcc tatgggagc ccaggaagct       900
gctcacccaa gatttggtgc aggaaaagta cctggagtac cggcaggtgc cggacagtga       960
tcccgcacgc tatgagttcc tgtggggtcc aagggccctt gctgaaacca gctatgtgaa      1020
agtccttgag tatgtgatca aggtcagtgc aagagttcgc tttttcttcc catccctgcg      1080
tgaagcagct ttgagagagg aggaagaggg agtctgagca tgagttgcag ccagggccag      1140
tgggaggggg actgggccag tgcaccttcc agggccgcgt ccagcagctt ccctgcctc      1200
gtgtgacatg aggcccattc ttcactctga agagagcggt cagtgttctc agtagtaggt      1260
ttctgttcta ttgggtgact tggagattta tctttgttct cttttggaat tgttcaaatg      1320
ttttttttta agggatggtt gaatgaactt cagcatccaa gttatgaat gacagcagtc      1380
acacagttct gtgtatatag tttaagggta agagtcttgt gttttattca gattgggaaa      1440
tccattctat tttgtgaatt gggataataa cagcagtgga ataagtactt agaaatgtga      1500
aaaatgagca gtaaaataga tgagataaag aactaaagaa attaagagat agtcaattct      1560
tgctttatac ctcagtctat tctgtaaaat ttttaaagat atatgcatac ctggatttcc      1620
ttggcttctt tgagaatgta agagaaatta aatctgaata aagaattctt cctgttaaaa      1680
aaaaaaaaaa aaaaaaaaaa aaaaaaaaaa aaaaaaaaaa aa                          1722
```

<210> SEQ ID NO 7
<211> LENGTH: 1753
<212> TYPE: DNA
<213> ORGANISM: Homo sapiens

<400> SEQUENCE: 7

```
gagattctcg ccctgagcaa cgagcgacgg cctgacgtcg gcggagggaa gccggcccag        60
```

-continued

```
gctcggtgag gaggcaaggt tctgagggga caggctgacc tggaggacca gaggcccccg      120
gaggagcact gaaggagaag atctgccagt gggtctccat tgcccagctc ctgcccacac      180
tcccgcctgt tgccctgacc agagtcatca tgcctcttga gcagaggagt cagcactgca      240
agcctgaaga aggccttgag gcccgaggag aggccctggg cctggtgggt gcgcaggctc      300
ctgctactga ggagcaggag gctgcctcct cctcttctac tctagttgaa gtcaccctgg      360
gggaggtgcc tgctgccgag tcaccagatc ctccccagag tcctcaggga gcctccagcc      420
tccccactac catgaactac cctctctgga gccaatccta tgaggactcc agcaaccaag      480
aagaggaggg gccaagcacc ttccctgacc tggagtccga gttccaagca gcactcagta      540
ggaaggtggc cgagttggtt catttttctgc tcctcaagta tcgagccagg agccggtca      600 caaaggcaga aatgctgggg agtgtcgtcg gaaattggca gtatttcttt cctgtgatct      660
tcagcaaagc ttccagttcc ttgcagctgg tctttggcat cgagctgatg gaagtggacc      720
ccatcggcca cttgtacatc tttgccacct gcctgggcct ctcctacgat ggcctgctgg      780
gtgacaatca gatcatgccc aaggcaggcc tcctgataat cgtcctggcc ataatcgcaa      840
gagagggcga ctgtgcccct gaggagaaaa tctggaggga gctgagtgtg ttagaggtgt      900
ttgaggggag ggaagacagt atcttgggg atcccaagaa gctgctcacc caacatttcg      960
tgcaggaaaa ctacctggag taccggcagg tccccggcag tgatcctgca tgttatgaat      1020
tcctgtgggg tccaagggcc ctcgttaaaa ccagctatgt gaaagtcctg caccatatgg      1080
taaagatcag tggaggacct cacatttcct acccacccct gcatgagtgg gttttgagag      1140
agggggaaga gtgagtctga gcacgagttg cagccagggc cagtgggagg gggtctgggc      1200
cagtgcacct tccggggccg catcccttag tttccactgc tcctgtgac gtgaggccca      1260 ttcttcactc tttgaagcga gcagtcagca ttcttagtag tgggtttctg ttctgttgga      1320
tgactttgag attattcttt gtttcctgtt ggagttgttc aaatgttcct tttaacggat      1380
ggttgaatga gcgtcagcat ccaggtttat gaatgacagt agtcacacat agtgctgttt      1440
atatagttta ggagtaagag tcttgttttt tactcaaatt gggaaatcca ttccattttg      1500
tgaattgtga cataataata gcagtggtaa aagtatttgc ttaaaattgt gagcgaatta      1560
gcaataacat acatgagata actcaagaaa tcaaaagata gttgattctt gccttgtacc      1620
tcaatctatt ctgtaaaatt aaacaaatat gcaaaccagg atttccttga cttctttgag      1680
aatgcaagcg aaattaaatc tgaataaata attcttcctc ttcaaaaaaa aaaaaaaaa      1740 aaaaaaaaaa aaa                                                        1753
```

<210> SEQ ID NO 8
<211> LENGTH: 1723
<212> TYPE: DNA
<213> ORGANISM: Homo sapiens

<400> SEQUENCE: 8

```
agcaacgagc gacggcctga cgtcggcgga gggaagccgg cccaggctcg gtgaggaggc       60
aaggttctga ggggacaggc tgacctggag gaccagaggc cccggagga gcactgaagg      120 agaagatctg ccagtgggtc tccattgccc agctcctgcc cacactcccg cctgttgccc      180
tgaccagagt catcatgcct cttgagcaga ggagtcagca ctgcaagcct gaagaaggcc      240
ttgaggcccg aggagaggcc ctgggcctgg tgggtgcgca ggctcctgct actgaggagc      300
aggaggctgc ctcctcctct tctactctag ttgaagtcac cctgggggag gtgcctgctg      360
```

-continued

| | | | | |
|---|---|---|---|---|
| ccgagtcacc | agatcctccc | cagagtcctc | agggagcctc | cagcctcccc actaccatga | 420 |
| actaccctct | ctggagccaa | tcctatgagg | actccagcaa | ccaagaagag gaggggccaa | 480 |
| gcacctcccc | tgacctggag | tctgagttcc | aagcagcact | cagtaggaag gtggccaagt | 540 |
| tggttcattt | tctgctcctc | aagtatcgag | ccagggagcc | ggtcacaaag gcagaaatgc | 600 |
| tggggagtgt | cgtcggaaat | tggcagtact | tctttcctgt | gatcttcagc aaagcttccg | 660 |
| attccttgca | gctggtcttt | ggcatcgagc | tgatggaagt | ggaccccatc ggccacgtgt | 720 |
| acatctttgc | cacctgcctg | gcctctcct | acgatggcct | gctgggtgac aatcagatca | 780 |
| tgcccaagac | aggcttcctg | ataatcatcc | tggccataat | cgcaaaagag ggcgactgtg | 840 |
| cccctgagga | gaaaatctgg | gaggagctga | gtgtgttaga | ggtgtttgag gggagggaag | 900 |
| acagtatctt | cggggatccc | aagaagctgc | tcacccaata | tttcgtgcag gaaaactacc | 960 |
| tggagtaccg | gcaggtcccc | ggcagtgatc | ctgcatgcta | tgagttcctg tggggtccaa | 1020 |
| gggccctcat | tgaaaccagc | tatgtgaaag | tcctgcacca | tatggtaaag atcagtggag | 1080 |
| gacctcgcat | ttcctaccca | ctcctgcatg | agtgggcttt | gagagagggg gaagagtgag | 1140 |
| tctgagcacg | agttgcagcc | agggccagtg | ggagggggtt | tgggccagtg caccttccgg | 1200 |
| ggccccatcc | cttagtttcc | actgcctcct | gtgacgtgag | gcccattctt cactctttga | 1260 |
| agcgagcagt | cagcattctt | agtagtgggt | ttctgttctg | ttggatgact ttgagattat | 1320 |
| tctttgtttc | ctgttggagt | tgttcaaatg | ttccttttaa | cggatggttg aatgagcgtc | 1380 |
| agcatccagg | tttatgaatg | acagtagtca | cacatagtgc | tgtttatata gtttaggagt | 1440 |
| aagagtcttg | tttttttattc | agattgggaa | atccattcca | ttttgtgaat tgtgacataa | 1500 |
| taatagcagt | ggtaaaagta | tttgcttaaa | attgtgagcg | aattagcaat aacatacatg | 1560 |
| agataactca | agaaatcaaa | agatagttga | ttcttgcctt | gtacctcaat ctattctgta | 1620 |
| aaattaaaca | aatatgcaaa | ccaggatttc | cttgacttct | ttgagaatgc aagcgaaatt | 1680 |
| aaatctgaat | aaataattaa | aaaaaaaaaa | aaaaaaaaaa | aaa | 1723 |

<210> SEQ ID NO 9
<211> LENGTH: 1524
<212> TYPE: DNA
<213> ORGANISM: Homo sapiens

<400> SEQUENCE: 9

| | | | | |
|---|---|---|---|---|
| agcagacaga | ggactctcat | taaggaaggt | gtcctgtgcc | ctgaccctac aagatgccaa | 60 |
| gagaagatgc | tcacttcatc | tatggttacc | ccaagaaggg | gcacgccac tcttacacca | 120 |
| cggctgaaga | ggccgctggg | atcggcatcc | tgacagtgat | cctgggagtc ttactgctca | 180 |
| tcggctgttg | gtattgtaga | agacgaaatg | gatacagagc | cttgatggat aaaagtcttc | 240 |
| atgttggcac | tcaatgtgcc | ttaacaagaa | gatgcccaca | agaagggttt gatcatcggg | 300 |
| acagcaaagt | gtctcttcaa | gagaaaaact | gtgaacctgt | ggttcccaat gctccacctg | 360 |
| cttatgagaa | actctctgca | gaacagtcac | caccaccttta | ttcacttaa gagccagcga | 420 |
| gacacctgag | acatgctgaa | attatttctc | tcacactttt | gcttgaattt aatacagaca | 480 |
| tctaatgttc | tcctttggaa | tggtgtagga | aaaatgcaag | ccatctctaa taataagtca | 540 |
| gtgttaaaat | tttagtaggt | ccgctagcag | tactaatcat | gtgaggaaat gatgagaaat | 600 |
| attaaattgg | gaaaactcca | tcaataaatg | ttgcaatgca | tgatactatc tgtgccagag | 660 |
| gtaatgttag | taaatccatg | gtgttatttt | ctgagagaca | gaattcaagt gggtattctg | 720 |
| gggccatcca | atttctcttt | acttgaaatt | tggctaataa | caaactagtc aggttttcga | 780 |

| | |
|---|---|
| accttgaccg acatgaactg tacacagaat tgttccagta ctatggagtg ctcacaaagg | 840 |
| atacttttac aggttaagac aaagggttga ctggcctatt tatctgatca agaacatgtc | 900 |
| agcaatgtct ctttgtgctc taaaattcta ttatactaca ataatatatt gtaaagatcc | 960 |
| tatagctctt ttttttttgag atggagtttc gcttttgttg cccaggctgg agtgcaatgg | 1020 |
| cgcgatcttg gctcaccata acctccgcct cccaggttca agcaattctc ctgccttagc | 1080 |
| ctcctgagta gctgggatta caggcgtgcg ccactatgcc tgactaattt tgtagtttta | 1140 |
| gtagagacgg ggtttctcca tgttggtcag gctggtctca aactcctgac ctcaggtgat | 1200 |
| ctgcccgcct cagcctccca agtgctgga attacaggcg tgagccacca cgcctggctg | 1260 |
| gatcctatat cttaggtaag acatataacg cagtctaatt acatttcact tcaaggctca | 1320 |
| atgctattct aactaatgac aagtattttc tactaaacca gaaattggta gaaggattta | 1380 |
| aataagtaaa agctactatg tactgcctta gtgctgatgc ctgtgtactg ccttaaatgt | 1440 |
| acctatggca atttagctct cttgggttcc caaatccctc tcacaagaat gtgcagaaga | 1500 |
| aatcataaag gatcagagat tctg | 1524 |

<210> SEQ ID NO 10
<211> LENGTH: 1881
<212> TYPE: DNA
<213> ORGANISM: Homo sapiens

<400> SEQUENCE: 10

| | |
|---|---|
| cctgcatctt tttggaagga ttctttttat aaatcagaaa gtgttcgagg ttcaaaggtt | 60 |
| tgcctcggag cgtgtgaaca ttcctccgct cggttttcaa ctcgcctcca acctgcgccg | 120 |
| cccggccagc atgtctcccc gcccgtgaag cggggctgcc gcctccctgc cgctccggct | 180 |
| gccactaacg acccgccctc gccgccacct ggccctcctg atcgacgaca cacgcacttg | 240 |
| aaacttgttc tcagggtgtg tggaatcaac tttccggaag caaccagccc accagaggag | 300 |
| gtcccgagcg cgagcggaga cgatgcagcg gagactggtt cagcagtgga gcgtcgcggt | 360 |
| gttcctgctg agctacgcgg tgccctcctg cgggcgctcg gtggagggtc tcagccgccg | 420 |
| cctcaaaaga gctgtgtctg aacatcagct cctccatgac aaggggaagt ccatccaaga | 480 |
| tttacggcga cgattcttcc ttcaccatct gatcgcagaa atccacacag ctgaaatcag | 540 |
| agctacctcg gaggtgtccc ctaactccaa gccctctccc aacacaaaga accacccgt | 600 |
| ccgatttggg tctgatgatg agggcagata cctaactcag gaaactaaca aggtggagac | 660 |
| gtacaaagag cagccgctca agacacctgg gaagaaaaag aaaggcaagc ccgggaaacg | 720 |
| caaggagcag gaaaagaaaa aacggcgaac tcgctctgcc tggttagact ctggagtgac | 780 |
| tgggagtggg ctagaagggg accacctgtc tgacacctcc acaacgtcgc tggagctcga | 840 |
| ttcacggtaa caggcttctc tggcccgtag cctcagcggg gtgctctcag ctgggttttg | 900 |
| gagcctccct tctgccttgg cttggacaaa cctagaattt ctcccttta tgtatctcta | 960 |
| tcgattgtgt agcaattgac agagaataac tcagaatatt gtctgcctta aagcagtacc | 1020 |
| ccctaccac acacacccct gtcctccagc accatagaga ggcgctagag cccattcctc | 1080 |
| tttctccacc gtcacccaac atcaatcctt taccactcta ccaaataatt tcatattcaa | 1140 |
| gcttcagaag ctagtgacca tcttcataat ttgctggaga agtgtgtttc ttccccttac | 1200 |
| tctcacacct gggcaaactt tcttcagtgt ttttcatttc ttacgttctt tcacttcaag | 1260 |
| ggagaatata gaagcatttg atattatcta caaacactgc agaacagcat catgtcataa | 1320 |

-continued

```
acgattctga gccattcaca cttttttattt aattaaatgt atttaattaa atctcaaatt    1380
tattttaatg taaagaactt aaattatgtt ttaaacacat gccttaaatt tgtttaatta    1440
aatttaactc tggttttctac cagctcatac aaaataaatg gtttctgaaa atgtttaagt   1500
attaacttac aaggatatag gttttttctca tgtatctttt tgttcattgg caagatgaaa   1560
taatttttct agggtaatgc cgtaggaaaa ataaaacttc acatttatgt ggcttgttta    1620
tccttagctc acagattgag gtaataatga cactcctaga ctttgggatc aaataactta   1680
gggccaagtc ttgggtctga atttatttaa gttcacaacc tagggcaagt tactctgcct   1740
ttctaagact cacttacatc ttctgtgaaa tataattgta ccaacctcat agagtttggt    1800
gtcaactaaa tgagattata tgtggactaa atatctgtca tatagtaaac actcaataaa   1860
ttgcaacata ttaaaaaaaa a                                               1881

<210> SEQ ID NO 11
<211> LENGTH: 3336
<212> TYPE: DNA
<213> ORGANISM: Homo sapiens

<400> SEQUENCE: 11
ttttcttaga cattaactgc agacggctgg caggatagaa gcagcggctc acttggactt      60
tttcaccagg gaaatcagag acaatgatgg ggctcttccc cagaactaca ggggctctgg    120
ccatcttcgt ggtggtcata ttggttcatg gagaattgcg aatagagact aaaggtcaat    180
atgatgaaga agagatgact atgcaacaag ctaaaagaag gcaaaaacgt gaatgggtga    240
aatttgccaa accctgcaga gaaggagaag ataactcaaa aagaaaccca attgccaaga    300
ttacttcaga ttaccaagca acccagaaaa tcacctaccg aatctctgga gtgggaatcg    360
atcagccgcc ttttggaatc tttgttgttg acaaaaacac tggagatatt aacataacag    420
ctatagtcga ccgggaggaa actccaagct tcctgatcac atgtcgggct ctaaatgccc    480
aaggactaga tgtagagaaa ccacttatac taacggttaa aattttggat attaatgata    540
atcctccagt attttcacaa caaatttttca tgggtgaaat tgaagaaaat agtgcctcaa    600
actcactggt gatgatacta atgccacaga tgcagatga accaaaccac ttgaattcta     660
aaattgcctt caaaattgtc tctcaggaac cagcaggcac acccatgttc ctcctaagca    720
gaaacactgg ggaagtccgt actttgacca attctcttga ccgagagcaa gctagcagct    780
atcgtctggt tgtgagtggt gcagacaaag atggagaagg actatcaact caatgtgaat    840
gtaatattaa agtgaaagat gtcaacgata acttcccaat gtttagagac tctcagtatt    900
cagcacgtat tgaagaaaat attttaagtt ctgaattact tcgatttcaa gtaacagatt    960
tggatgaaga gtacacagat aattggcttg cagtatattt ctttacctct gggaatgaag   1020
gaaattggtt tgaaatacaa actgatccta gaactaatga aggcatcctg aaagtggtga   1080
aggctctaga ttatgaacaa ctacaaagcg tgaaacttag tattgctgtc aaaaacaaag   1140
ctgaatttca ccaatcagtt atctctcgat accgagttca gtcaaccccca gtcacaattc   1200 aggtaataaa tgtaagagaa ggaattgcat tccgtcctgc ttccaagaca tttactgtgc   1260
aaaaaggcat aagtagcaaa aaattggtgg attatatcct gggaacatat caagccatcg   1320
atgaggacac taacaaagct gcctcaaatg tcaaatatgt catgggacgt aacgatggtg   1380
gatacctaat gattgattca aaaactgctg aaatcaaatt tgtcaaaaat atgaaccgag   1440
attctacttt catagttaac aaaacaatca cagctgaggt tctggccata gatgaataca   1500
cgggtaaaac ttctacaggc acggtatatg ttagagtacc cgatttcaat gacaattgtc   1560
```

```
caacagctgt cctcgaaaaa gatgcagttt gcagttcttc accttccgtg gttgtctccg    1620
ctagaacact gaataataga tacactggcc cctatacatt tgcactggaa gatcaacctg    1680
taaagttgcc tgccgtatgg agtatcacaa ccctcaatgc tacctcggcc ctcctcagag    1740
cccaggaaca gatacctcct ggagtatacc acatctccct ggtacttaca gacagtcaga    1800
acaatcggtg tgagatgcca cgcagcttga cactggaagt ctgtcagtgt gacaacaggg    1860
gcatctgtgg aacttcttac ccaaccacaa gccctgggac caggtatggc aggccgcact    1920
cagggaggct ggggcctgcc gccatcggcc tgctgctcct tggtctcctg ctgctgctgt    1980 tggccccccct tctgctgttg acctgtgact gtggggcagg ttctactggg ggagtgacag    2040
gtggttttat cccagttcct gatggctcag aaggaacaat tcatcagtgg ggaattgaag    2100
gagcccatcc tgaagacaag gaaatcacaa atatttgtgt gcctcctgta acagccaatg    2160
gagccgattt catggaaagt tctgaagttt gtacaaatac gtatgccaga ggcacagcgg    2220
tggaaggcac ttcaggaatg gaaatgacca ctaagcttgg agcagccact gaatctggag    2280
gtgctgcagg ctttgcaaca gggacagtgt caggagctgc ttcaggattc ggagcagcca    2340
ctggagttgg catctgttcc tcagggcagt ctggaaccat gagaacaagg cattccactg    2400
gaggaaccaa taaggactac gctgatgggg cgataagcat gaattttctg gactcctact    2460
tttctcagaa agcatttgcc tgtgcggagg aagacgatgg ccaggaagca aatgactgct    2520
tgttgatcta tgataatgaa ggcgcagatg ccactggttc cctgtgggc tccgtgggtt    2580 gttgcagttt tattgctgat gacctggatg acagcttctt ggactcactt ggacccaaat    2640
ttaaaaaact tgcagagata agccttggtg ttgatggtga aggcaaagaa gttcagccac    2700
cctctaaaga cagcggttat gggattgaat cctgtggcca tcccatagaa gtccagcaga    2760
caggatttgt taagtgccag actttgtcag gaagtcaagg agcttctgct ttgtccgcct    2820
ctgggtctgt ccagccagct gtttccatcc ctgaccctct gcagcatggt aactatttag    2880
taacggagac ttactcggct tctggttccc tcgtgcaacc ttccactgca ggctttgatc    2940
cacttctcac acaaaatgtg atagtgacag aaagggtgat ctgtcccatt ccagtgttc     3000 ctggcaacct agctggccca acgcagctac gagggtcaca tactatgctc tgtacagagg    3060
atccttgctc ccgtctaata tgaccagaat gagctgaat accacactga ccaaatctgg     3120
atctttggac taaagtattc aaaatagcat agcaaagctc actgtattgg gctaataatt    3180
tggcacttat tagcttctct cataaactga tcacgattat aaattaaatg tttgggttca    3240
taccccaaaa gcaatatgtt gtcactccta attctcaagt actattcaaa ttgtagtaaa    3300
tcttaaagtt tttcaaaacc ctaaaatcat attcgc                              3336
```

<210> SEQ ID NO 12
<211> LENGTH: 1694
<212> TYPE: DNA
<213> ORGANISM: Homo sapiens

<400> SEQUENCE: 12

```
ctctctgccc acctctgctt cctctaggaa cacaggagtt ccagatcaca tcgagttcac      60
catgaattca ctcagtgaag ccaacaccaa gttcatgttc gacctgttcc aacagttcag     120
aaaatcaaaa gagaacaaca tcttctattc ccctatcagc atcacatcag cattagggat     180
ggtcctctta ggagccaaag acaacactgc acaacagatt aagaaggttc ttcactttga     240
tcaagtcaca gagaacacca caggaaaagc tgcaacatat catgttgata ggtcaggaaa     300
```

```
tgttcatcac cagtttcaaa agcttctgac tgaattcaac aaatccactg atgcatatga    360
gctgaagatc gccaacaagc tcttcggaga aaaaacgtat ctattttac aggaatattt      420 agatgccatc aagaaatttt accagaccag tgtggaatct gttgattttg caaatgctcc    480
agaagaaagt cgaagaaga ttaactcctg ggtggaaagt caaacgaatg aaaaaattaa      540
aaacctaatt cctgaaggta atattggcag caataccaca ttggttcttg tgaacgcaat    600
ctatttcaaa gggcagtggg agaagaaatt taataaagaa gatactaaag aggaaaaatt    660
ttggccaaac aagaatacat acaagtccat acagatgatg aggcaataca catcttttca    720
ttttgcctcg ctggaggatg tacaggccaa ggtcctggaa ataccataca aaggcaaaga    780
tctaagcatg attgtgttgc tgccaaatga aatcgatggt ctccagaagc ttgaagagaa    840
actcactgct gagaaattga tggaatggac aagtttgcag aatatgagag agacacgtgt    900
cgatttacac ttacctcggt tcaaagtgga agagagctat gacctcaagg acacgttgag    960
aaccatggga atggtggata tcttcaatgg ggatgcagac ctctcaggca tgaccgggag    1020
ccgcggtctc gtgctatctg gagtcctaca caaggccttt gtggaggtta cagaggaggg    1080
agcagaagct gcagctgcca ccgctgtagt aggattcgga tcatcaccta cttcaactaa    1140
tgaagagttc cattgtaatc acccttcct attcttcata aggcaaaata agaccaacag    1200
catcctcttc tatggcagat tctcatcccc gtagatgcaa ttagtctgtc actccatttg    1260
gaaaatgttc acctgcagat gttctggtaa actgattgct ggcaacaaca gattctcttg    1320
gctcatattt cttttctttc tcatcttgat gatgatcgtc atcatcaaga atttaatgat    1380
taaaatagca tgcctttctc tctttctctt aataagccca catataaatg tacttttttct    1440 tccagaaaaa ttctccttga ggaaaaatgt ccaaaataag atgaatcact taataccgta    1500
tcttctaaat ttgaaatata attctgtttg tgacctgttt taaatgaacc aaaccaaatc    1560 atacttttc tttgaattta gcaacctaga aacacacatt tctttgaatt taggtgatac    1620
ctaaatcctt cttatgtttc taaattttgt gattctataa aacacatcat caataaaata    1680
gtgacataaa atca                                                       1694

<210> SEQ ID NO 13
<211> LENGTH: 1782
<212> TYPE: DNA
<213> ORGANISM: Homo sapiens

<400> SEQUENCE: 13
gggagacaca cacagcctct ctgcccacct ctgcttcctc taggaacaca ggagttccag     60
atcacatcga gttcaccatg aattcactca gtgaagccaa caccaagttc atgttcgatc    120
tgttccaaca gttcagaaaa tcaaaagaga acaacatctt ctattcccct atcagcatca    180
catcagcatt agggatggtc ctcttaggag ccaaagacaa cactgcacaa caaattagca    240
aggttcttca ctttgatcaa gtcacagaga acaccacaga aaaagctgca acatatcatg    300
ttgataggtc aggaaatgtt catcaccagt ttcaaaagct tctgactgaa ttcaacaaat    360
ccactgatgc atatgagctg aagatcgcca acaagctctt cggagaaaag acgtatcaat    420
ttttacagga atatttagat gccatcaaga attttaccaga gaccagtgtg aatctactg    480 attttgcaaa tgctccagaa gaaagtcgaa agaagattaa ctcctgggtg aaagtcaaa    540 cgaatgaaaa aattaaaaac ctatttcctg atgggactat tggcaatgat acgacactgg    600
ttcttgtgaa cgcaatctat ttcaaagggc agtgggagaa taaatttaaa aagaaaaca    660 ctaaagagga aaaattttgg ccaaacaaga atacatacaa atctgtacag atgatgaggc    720
```

| | |
|---|---|
| aatacaattc ctttaattttt gccttgctgg aggatgtaca ggccaaggtc ctggaaatac | 780 |
| catacaaagg caaagatcta agcatgattg tgctgctgcc aaatgaaatc gatggtctgc | 840 |
| agaagcttga agagaaactc actgctgaga aattgatgga atggacaagt ttgcagaata | 900 |
| tgagagagac atgtgtcgat ttacacttac ctcggttcaa aatggaagag agctatgacc | 960 |
| tcaaggacac gttgagaacc atgggaatgg tgaatatctt caatgggat gcagacctct | 1020 |
| caggcatgac ctggagccac ggtctctcag tatctaaagt cctacacaag gcctttgtgg | 1080 |
| aggtcactga ggagggagtg gaagctgcag ctgccaccgc tgtagtagta gtcgaattat | 1140 |
| catctccttc aactaatgaa gagttctgtt gtaatcaccc tttcctattc ttcataaggc | 1200 |
| aaaataagac caacagcatc ctcttctatg gcagattctc atccccatag atgcaattag | 1260 |
| tctgtcactc catttagaaa atgttcacct agaggtgttc tggtaaactg attgctggca | 1320 |
| acaacagatt ctcttggctc atatttcttt tctatctcat cttgatgatg atagtcatca | 1380 |
| tcaagaattt aatgattaaa atagcatgcc tttctctctt tctcttaata agcccacata | 1440 |
| taaatgtact tttccttcca gaaaaatttc ccttgaggaa aaatgtccaa gataagatga | 1500 |
| atcatttaat accgtgtctt ctaaatttga aatataattc tgtttctgac ctgtttttaaa | 1560 |
| tgaaccaaac caaatcatac tttctcttca aatttagcaa cctagaaaca cacatttctt | 1620 |
| tgaatttagg tgatacctaa atccttctta tgtttctaaa ttttgtgatt ctataaaaca | 1680 |
| catcatcaat aaaataatga ctaaaaaaaa aaaaaaaaaa aaaaaaaaaa aaaaaaaaaa | 1740 |
| aaaaaaaaaa aacccaaaaa aaaaaaaaaa aaaaaaaaaa aa | 1782 |

<210> SEQ ID NO 14
<211> LENGTH: 1528
<212> TYPE: DNA
<213> ORGANISM: Homo sapiens

<400> SEQUENCE: 14

| | |
|---|---|
| cggcgagcga gcaccttcga cgcggtccgg ggaccccctc gtcgctgtcc tcccgacgcg | 60 |
| gacccgcgtg ccccaggcct cgcgctgccc ggccggctcc tcgtgtccca ctcccggcgc | 120 |
| acgccctccc gcgagtcccg ggccctcccc gcgcccctct tctcggcgcg cgcgcagcat | 180 |
| ggcgcccccg caggtcctcg cgttcgggct tctgcttgcc gcggcgacgg cgacttttgc | 240 |
| cgcagctcag gaagaatgtg tctgtgaaaa ctacaagctg gccgtaaaact gctttgtgaa | 300 |
| taataatcgt caatgccagt gtacttcagt tggtgcacaa aatactgtca tttgctcaaa | 360 |
| gctggctgcc aaatgtttgg tgatgaaggc agaaatgaat ggctcaaaac ttgggagaag | 420 |
| agcaaaacct gaaggggccc tccagaacaa tgatgggctt tatgatcctg actgcgatga | 480 |
| gagcgggctc tttaaggcca agcagtgcaa cggcacctcc acgtgctggt gtgtgaacac | 540 |
| tgctggggtc agaagaacag acaaggacac tgaaataacc tgctctgagc gagtgagaac | 600 |
| ctactggatc atcattgaac taaaacacaa agcaagagaa aaaccttatg atagtaaaag | 660 |
| tttgcggact gcacttcaga aggagatcac aacgcgttat caactggatc caaaatttat | 720 |
| cacgagtatt ttgtatgaga ataatgttat cactattgat ctggttcaaa attcttctca | 780 |
| aaaaactcag aatgatgtgg acatagctga tgtggcttat tattttgaaa agatgttaa | 840 |
| aggtgaatcc ttgtttcatt ctaagaaaat ggacctgaca gtaaatgggg aacaactgga | 900 |
| tctggatcct ggtcaaactt taatttatta tgttgatgaa aaagcacctg aattctcaat | 960 |
| gcagggtcta aaagctggtg ttattgctgt tattgtggtt gtggtgatag cagttgttgc | 1020 |

```
tggaattgtt gtgctggtta tttccagaaa gaagagaatg gcaaagtatg agaaggctga   1080
gataaaggag atgggtgaga tgcataggga actcaatgca taactatata atttgaagat   1140
tatagaagaa gggaaatagc aaatggacac aaattacaaa tgtgtgtgcg tgggacgaag   1200
acatctttga aggtcatgag tttgttagtt aacatcata tatttgtaat agtgaaacct   1260
gtactcaaaa tataagcagc ttgaaactgg ctttaccaat cttgaaattt gaccacaagt   1320
gtcttatata tgcagatcta atgtaaaatc cagaacttgg actccatcgt taaaattatt   1380
tatgtgtaac attcaaatgt gtgcattaaa tatgcttcca cagtaaaatc tgaaaaactg   1440
atttgtgatt gaaagctgcc tttctattta cttgagtctt gtacatacat acttttttat   1500
gagctatgaa ataaaacatt ttaaactg                                     1528

<210> SEQ ID NO 15
<211> LENGTH: 2384
<212> TYPE: DNA
<213> ORGANISM: Homo sapiens

<400> SEQUENCE: 15
tattgagttc ttcaaacatt gtagcctctt tatggtctct gagaaataac taccttaaac     60
ccataatctt taatacttcc taaactttct taataagaga agctctattc ctgacactac    120
ctctcatttg caaggtcaaa tcatcattag tttttgtagtc tattaactgg gtttgcttag    180
gtcaggcatt attattacta accttattgt taatattcta accataagaa ttaaactatt    240
aatggtgaat agagttttc actttaacat aggcctatcc cactggtggg atacgagcca    300
attcgaaaga aaagtcagtc atgtgctttt cagaggatga aagcttaaga taaagactaa    360
aagtgtttga tgctggaggt gggagtggta ttatataggt ctcagccaag acatgtgata    420
atcactgtag tagtagctgg aaagagaaat ctgtgactcc aattagccag ttcctgcaga    480
ccttgtgagg actagaggaa gaatgctcct ggctgttttg tactgcctgc tgtggagttt    540
ccagacctcc gctggccatt tccctagagc ctgtgtctcc tctaagaacc tgatggagaa    600
ggaatgctgt ccaccgtgga gcggggacag gagtccctgt ggccagcttt caggcagagg    660
ttcctgtcag aatatccttc tgtccaatgc accacttggg cctcaatttc ccttcacagg    720
ggtggatgac cggagtcgt ggccttccgt ctttttataat aggacctgcc agtgctctgg    780
caacttcatg ggattcaact gtggaaactg caagtttggc ttttgggac caaactgcac    840 agagagacga ctcttggtga agaaacat cttcgatttg agtgccccag agaaggacaa    900
attttttgcc tacctcactt tagcaaagca taccatcagc tcagactatg tcatccccat    960
agggacctat ggccaaatga aaatggatc aacacccatg tttaacgaca tcaatattta   1020
tgacctcttt gtctggatgc attattatgt gtcaatggat gcactgcttg ggggatctga   1080
aatctggaga gacattgatt ttgcccatga agcaccagct tttctgcctt ggcatagact   1140
cttcttgttg cggtgggaac aagaaatcca gaagctgaca ggagatgaaa acttcactat   1200
tccatattgg gactggcggg atgcagaaaa gtgtgacatt tgcacagatg agtacatggg   1260
aggtcagcac cccacaaatc ctaacttact cagcccagca tcattcttct cctcttggca   1320
gattgtctgt agccgattgg aggagtacaa cagccatcag tctttatgca atggaacgcc   1380
gattgtctgt agccgattgg aggagtacaa cagccatcag tctttatgca atggaacgcc   1380
cgagggacct ttacggcgta atcctggaaa ccatgacaaa tccagaaccc caaggctccc   1440
ctcttcagct gatgtagaat tttgcctgag tttgacccaa tatgaatctg gttccatgga   1500
taaagctgcc aatttcagct ttagaaatac actggaagga tttgctagtc cacttactgg   1560
gatagcggat gcctctcaaa gcagcatgca caatgccttg cacatctata tgaatggaac   1620
```

| | |
|---|---|
| aatgtcccag gtacagggat ctgccaacga tcctatcttc cttcttcacc atgcatttgt | 1680 |
| tgacagtatt tttgagcagt ggctccgaag gcaccgtcct cttcaagaag tttatccaga | 1740 |
| agccaatgca cccattggac ataaccggga atcctacatg gttccttta taccactgta | 1800 |
| cagaaatggt gatttctta tttcatccaa agatctgggc tatgactata gctatctaca | 1860 |
| agattcagac ccagactctt ttcaagacta cattaagtcc tatttggaac aagcgagtcg | 1920 |
| gatctggtca tggctccttg gggcggcgat ggtaggggcc gtcctcactg ccctgctggc | 1980 |
| agggcttgtg agcttgctgt gtcgtcacaa gagaaagcag cttcctgaag aaaagcagcc | 2040 |
| actcctcatg gagaaagagg attaccacag cttgtatcag agccatttat aaaaggctta | 2100 |
| ggcaatagag tagggccaaa aagcctgacc tcactctaac tcaaagtaat gtccaggttc | 2160 |
| ccagagaata tctgctggta ttttctgta aagaccattt gcaaaattgt aacctaatac | 2220 |
| aaagtgtagc cttcttccaa ctcaggtaga acacacctgt ctttgtcttg ctgttttcac | 2280 |
| tcagcccttt taacattttc ccctaagccc atatgtctaa ggaaaggatg ctatttggta | 2340 |
| atgaggaact gttatttgta tgtgaattaa agtgctctta tttt | 2384 |

<210> SEQ ID NO 16
<211> LENGTH: 2702
<212> TYPE: DNA
<213> ORGANISM: Homo sapiens

<400> SEQUENCE: 16

| | |
|---|---|
| cattctcccc caggctcact caccatgacc aagctgagcg cccaagtcaa aggctctctc | 60 |
| aacatcacca ccccgggggct gcagatatgg aggatcgagg ccatgcagat ggtgcctgtt | 120 |
| ccttccagca cctttggaag cttcttcgat ggtgactgct acatcatcct ggctatccac | 180 |
| aagacagcca gcagcctgtc ctatgacatc cactactgga ttggccagga ctcatccctg | 240 |
| gatgagcagg gggcagctgc catctacacc acacagatgg atgacttcct gaagggccgg | 300 |
| gctgtgcagc accgcgaggt ccagggcaac gagagcgagg ccttccgagg ctacttcaag | 360 |
| caaggccttg tgatccggaa aggggggcgtg gcttctggca tgaagcacgt ggagaccaac | 420 |
| tcctatgacg tccagaggct gctgcatgtc aagggcaaga ggaacgtggt agctggagag | 480 |
| gtagagatgt cctggaagag tttcaaccga ggggatgttt cctcctgga ccttgggaag | 540 |
| cttatcatcc agtggaatgg accggaaagc acccgtatgg agagactcag gggcatgact | 600 |
| ctggccaagg agatccgaga ccaggagcgg ggagggcgca cctatgtagg cgtggtggac | 660 |
| ggagagaatg aattggcatc cccgaagctg atggaggtga tgaaccacgt gctgggcaag | 720 |
| cgcagggagc tgaaggcggc cgtgcccgac acggtggtgg agccggcact caaggctgca | 780 |
| ctcaaactgt accatgtgtc tgactccgag gggaatctgg tggtgaggga agtcgccaca | 840 |
| cggccactga cacaggacct gctcagtcac gaggactgtt acatcctgga ccaggggggc | 900 |
| ctgaagatct acgtgtggaa agggaagaaa gccaatgagc aggagaagaa gggagccatg | 960 |
| agccatgcgc tgaacttcat caaagccaag cagtacccac caagcacaca ggtggaggtg | 1020 |
| cagaatgatg gggctgagtc ggccgtcttt cagcagctct tccagaagtg acagcgtcc | 1080 |
| aaccggacct caggcctagg caaaacccac actgtgggct ccgtggccaa agtggaacag | 1140 |
| gtgaagttcg atgccacatc catgcatgtc aagcctcagg tggctgccca gcagaagatg | 1200 |
| gtagatgatg ggagtgggga agtgcaggtg tggcgcattg agaacctaga gctggtacct | 1260 |
| gtggattcca gtggctagg ccacttctat gggggcgact gctacctgct gctctacacc | 1320 |

-continued

```
tacctcatcg gcgagaagca gcattacctg ctctacgttt ggcagggcag ccaggccagc    1380
caagatgaaa ttacagcatc agcttatcaa gccgtcatcc tggaccagaa gtacaatggt    1440
gaaccagtcc agatccgggt cccaatgggc aaggagccac ctcatcttat gtccatcttc    1500
aagggacgca tggtggtcta ccagggaggc acctcccgaa ctaacaactt ggagaccggg    1560
ccctccacac ggctgttcca ggtcagggga actggcgcca acaacaccaa ggcctttgag    1620
gtcccagcgc gggccaattt cctcaattcc aatgatgtct ttgtcctcaa gacccagtct    1680
tgctgctatc tatggtgtgg gaagggttgt agcgggacg agcgggagat ggccaagatg    1740
gttgctgaca ccatctcccg gacggagaag caagtggtgg tggaagggca ggagccagcc    1800
aacttctgga tggccctggg tgggaaggcc ccctatgcca acaccaagag actacaggaa    1860
gaaaacctgg tcatcacccc ccggctcttt gagtgttcca acaagactgg gcgcttcctg    1920
gccacagaga tccctgactt caatcaggat gacttggaag aggatgatgt gttcctacta    1980
gatgtctggg accaggtctt cttctggatt gggaaacatg ccaacgagga ggagaagaag    2040
gccgcagcaa ccactgcaca ggaataccte aagacccatc ccagcgggcg tgaccctgag    2100
accccccatca ttgtggtgaa gcagggacac gagcccccca ccttcacagg ctggttcctg    2160
gcttgggatc ccttcaagtg gagtaacacc aaatcctatg aggacctgaa ggcggagtct    2220
ggcaacctta gggactggag ccagatcact gctgaggtca aagcccccaa agtgacgtg     2280
ttcaatgcta acagcaacct cagttctggg cctctgccca tcttcccct ggagcagcta    2340
gtgaacaagc ctgtagagga gctccccgag ggtgtggacc ccagcaggaa ggaggaacac    2400
ctgtccattg aagatttcac tcaggccttt gggatgactc cagctgcctt ctctgctctg    2460
cctcgatgga agcaacaaaa cctcaagaaa gaaaaaggac tatttttgaga agagtagctg   2520
tggttgtaaa gcagtaccct accctgattg tagggtctca ttttctcacc gatattagtc    2580
ctacaccaat tgaagtgaaa ttttgcagat gtgcctatga gcacaaactt ctgtggcaaa    2640
tgccagtttt gtttaataat gtacctattc cttcagaaag atgatacccc aaaaaaaaaa    2700
aa                                                                    2702
```

<210> SEQ ID NO 17
<211> LENGTH: 24
<212> TYPE: DNA
<213> ORGANISM: Homo sapiens

<400> SEQUENCE: 17
gattgtgatg taacggctgt aatg                                            24

<210> SEQ ID NO 18
<211> LENGTH: 20
<212> TYPE: DNA
<213> ORGANISM: Homo sapiens

<400> SEQUENCE: 18
atccttgtcc tccacgggtt                                                 20

<210> SEQ ID NO 19
<211> LENGTH: 17
<212> TYPE: DNA
<213> ORGANISM: Homo sapiens

<400> SEQUENCE: 19
agatcgacaa cgcccgt                                                    17

```
<210> SEQ ID NO 20
<211> LENGTH: 20
<212> TYPE: DNA
<213> ORGANISM: Homo sapiens

<400> SEQUENCE: 20
agagcctgtt ccgtctcaaa                                               20

<210> SEQ ID NO 21
<211> LENGTH: 21
<212> TYPE: DNA
<213> ORGANISM: Homo sapiens

<400> SEQUENCE: 21
gggccttggt ctcctctaga g                                             21

<210> SEQ ID NO 22
<211> LENGTH: 19
<212> TYPE: DNA
<213> ORGANISM: Homo sapiens

<400> SEQUENCE: 22
ccagggagcg actgttgtc                                                19

<210> SEQ ID NO 23
<211> LENGTH: 21
<212> TYPE: DNA
<213> ORGANISM: Homo sapiens

<400> SEQUENCE: 23
gtgaggaggc aaggttytsa g                                             21

<210> SEQ ID NO 24
<211> LENGTH: 22
<212> TYPE: DNA
<213> ORGANISM: Homo sapiens

<400> SEQUENCE: 24
agacccacwg gcagatcttc tc                                            22

<210> SEQ ID NO 25
<211> LENGTH: 19
<212> TYPE: DNA
<213> ORGANISM: Homo sapiens

<400> SEQUENCE: 25
actgtcagga tgccgatcc                                                19

<210> SEQ ID NO 26
<211> LENGTH: 23
<212> TYPE: DNA
<213> ORGANISM: Homo sapiens

<400> SEQUENCE: 26
agcggcctct tcagccgtgg tgt                                           23

<210> SEQ ID NO 27
<211> LENGTH: 23
<212> TYPE: DNA
<213> ORGANISM: Homo sapiens

<400> SEQUENCE: 27
tcatggagga gctgatgttc aga                                           23
```

```
<210> SEQ ID NO 28
<211> LENGTH: 19
<212> TYPE: DNA
<213> ORGANISM: Homo sapiens

<400> SEQUENCE: 28
caaaaggcgg ctgatcgat                                                19

<210> SEQ ID NO 29
<211> LENGTH: 21
<212> TYPE: DNA
<213> ORGANISM: Homo sapiens

<400> SEQUENCE: 29
ggcgatcttc agctcatatg c                                             21

<210> SEQ ID NO 30
<211> LENGTH: 23
<212> TYPE: DNA
<213> ORGANISM: Homo sapiens

<400> SEQUENCE: 30
ggttttgctc ttctcccaag ttt                                           23

<210> SEQ ID NO 31
<211> LENGTH: 23
<212> TYPE: DNA
<213> ORGANISM: Homo sapiens

<400> SEQUENCE: 31
actgatggct gttgtactcc tcc                                           23

<210> SEQ ID NO 32
<211> LENGTH: 18
<212> TYPE: DNA
<213> ORGANISM: Homo sapiens

<400> SEQUENCE: 32
ttgccagact ccgccttc                                                 18

<210> SEQ ID NO 33
<211> LENGTH: 16
<212> TYPE: DNA
<213> ORGANISM: Homo sapiens

<400> SEQUENCE: 33
gtgaaggcca cagcat                                                   16

<210> SEQ ID NO 34
<211> LENGTH: 17
<212> TYPE: DNA
<213> ORGANISM: Homo sapiens

<400> SEQUENCE: 34
aactggctgc tgtaacg                                                  17

<210> SEQ ID NO 35
<211> LENGTH: 19
<212> TYPE: DNA
<213> ORGANISM: Homo sapiens

<400> SEQUENCE: 35
gccgatgagc agtaagact                                                19
```

```
<210> SEQ ID NO 36
<211> LENGTH: 20
<212> TYPE: DNA
<213> ORGANISM: Homo sapiens

<400> SEQUENCE: 36
tgtcaacaac aaagattcca                                               20

<210> SEQ ID NO 37
<211> LENGTH: 18
<212> TYPE: DNA
<213> ORGANISM: Homo sapiens

<400> SEQUENCE: 37
tctccgaaga gcttgttg                                                 18

<210> SEQ ID NO 38
<211> LENGTH: 17
<212> TYPE: DNA
<213> ORGANISM: Homo sapiens

<400> SEQUENCE: 38
agcccatcat tgttctg                                                  17

<210> SEQ ID NO 39
<211> LENGTH: 17
<212> TYPE: DNA
<213> ORGANISM: Homo sapiens

<400> SEQUENCE: 39
cgttccattg cataaag                                                  17

<210> SEQ ID NO 40
<211> LENGTH: 16
<212> TYPE: DNA
<213> ORGANISM: Homo sapiens

<400> SEQUENCE: 40
gctccagtcc ctaagg                                                   16
```